(12) United States Patent
Singh et al.

(10) Patent No.: US 9,150,649 B2
(45) Date of Patent: Oct. 6, 2015

(54) POTENT CONJUGATES AND HYDROPHILIC LINKERS

(75) Inventors: Rajeeva Singh, Framingham, MA (US); Yelena Kovtun, Stow, MA (US); Sharon D. Wilhelm, Brookline, MA (US); Ravi V. J. Chari, Newton, MA (US)

(73) Assignee: ImmunoGen, Inc., Waltham, MA (US)

( * ) Notice: Subject to any disclaimer, the term of this patent is extended or adjusted under 35 U.S.C. 154(b) by 644 days.

(21) Appl. No.: 12/574,466

(22) Filed: Oct. 6, 2009

(65) Prior Publication Data
US 2010/0129314 A1 May 27, 2010

Related U.S. Application Data

(63) Continuation-in-part of application No. 12/433,668, filed on Apr. 30, 2009, now abandoned.

(60) Provisional application No. 61/049,289, filed on Apr. 30, 2008.

(51) Int. Cl.
| | |
|---|---|
| *A61K 47/48* | (2006.01) |
| *C07K 16/28* | (2006.01) |
| *A61K 39/00* | (2006.01) |
| *A61P 35/00* | (2006.01) |
| *C07D 498/18* | (2006.01) |
| *C07K 16/30* | (2006.01) |

(52) U.S. Cl.
CPC ....... *C07K 16/2803* (2013.01); *A61K 47/48215* (2013.01); *A61K 47/48384* (2013.01); *A61K 47/48569* (2013.01); *A61K 47/48715* (2013.01); *C07D 498/18* (2013.01); *C07K 16/30* (2013.01); *A61K 47/48615* (2013.01); *A61K 47/48723* (2013.01); *C07K 2317/24* (2013.01)

(58) Field of Classification Search
CPC .................. A61K 47/48215; A61K 47/48569; A61K 47/48384; A61K 47/48723; C07K 16/2803; C07K 16/30; C07K 2317/24
See application file for complete search history.

(56) References Cited

U.S. PATENT DOCUMENTS

| | | | |
|---|---|---|---|
| 6,441,163 B1 | 8/2002 | Chari et al. | |
| 6,596,757 B1 | 7/2003 | Chari et al. | |
| 6,716,821 B2* | 4/2004 | Zhao et al. ........................ | 514/34 |
| 7,276,497 B2* | 10/2007 | Chari et al. ................. | 514/229.5 |
| 7,368,565 B2 | 5/2008 | Chari et al. | |
| 7,521,541 B2 | 4/2009 | Eigenbrot et al. | |
| 7,989,598 B2* | 8/2011 | Steeves et al. ............. | 530/391.7 |
| 8,163,888 B2 | 4/2012 | Steeves et al. | |
| 2003/0220245 A1 | 11/2003 | Hubbell et al. | |
| 2004/0001838 A1 | 1/2004 | Zhao et al. | |
| 2005/0169933 A1 | 8/2005 | Steeves et al. | |
| 2005/0276812 A1 | 12/2005 | Ebens, Jr. et al. | |
| 2006/0121042 A1* | 6/2006 | Dall'Acqua et al. ........ | 424/155.1 |
| 2006/0127352 A1 | 6/2006 | Hubbell et al. | |
| 2006/0182750 A1* | 8/2006 | Chari et al. ................. | 424/155.1 |
| 2007/0269447 A1* | 11/2007 | Chari et al. ................. | 424/179.1 |
| 2007/0270585 A1 | 11/2007 | Chari et al. | |
| 2008/0171865 A1 | 7/2008 | Steeves et al. | |
| 2008/0311040 A1* | 12/2008 | Berry et al. .................... | 424/9.1 |

FOREIGN PATENT DOCUMENTS

| | | |
|---|---|---|
| WO | 02/083030 A2 | 10/2002 |
| WO | 02/087497 A2 | 11/2002 |
| WO | 03/068144 A2 | 8/2003 |
| WO | 2004/103272 A2 | 12/2004 |
| WO | 2005/012484 A2 | 2/2005 |
| WO | 2005/037992 A2 | 4/2005 |
| WO | 2005/117986 A2 | 12/2005 |
| WO | 2006/034488 A2 | 3/2006 |
| WO | 2007/140371 A2 | 6/2007 |
| WO | 2007/100385 A2 | 9/2007 |
| WO | 2007/112193 A2 | 10/2007 |
| WO | 2009/012256 A1 | 1/2009 |
| WO | 2009/134976 A1 | 11/2009 |

OTHER PUBLICATIONS

Rudikoff et al, Proc. Natl. Acad. Sci. USA vol. 79: 1979, 1982.*
Yu et al, Investigative Ophthalmology & Visual Science 49(2): 522-527, Feb. 2008.*
Witte et al, Cancer and Metastasis Reviews 17: 155-161, 1998.*
Kellogg et al, Bioconjugate Chem 22: 717-726, Mar. 22, 2011.*
Stancovski et al, Proceedings of the National Academy of Science USA 88: 8691-8695, 1991.*
Bieniarz et al, Bioconjugate Chem 7: 88-95, 1996.*
Kumar et al., Expert Opin. Drug Discov 7(11): 1093-1106, 2012.*
International Search Report dated Jun. 9, 2009 which issued in International Application No. PCT/US09/42259.
Office Action issued in corresponding Chinese Patent Application No. 200980125295.2 on Oct. 24, 2012.
Cheng et al.; "Poly(ethylene Glycol) modification of [beta]-glucuronidase-antibody conjugates for solid-tumor therapy by targeted activation of glucuronide prodrugs;" Cancer Immunology—Immunotherapy; 44(6):305-315 (Aug. 14, 1997).

* cited by examiner

*Primary Examiner* — Phuong Huynh
(74) *Attorney, Agent, or Firm* — McCarter & English, LLP; Yu Lu; Xin Zhang

(57) ABSTRACT

Linkers for binding drugs to cell binding agents are modified to hydrophilic linkers by incorporating a polyethylene glycol spacer. The potency or the efficacy of the cell-binding agent-drug conjugates is surprisingly enhanced several folds in a variety of cancer cell types, including those expressing a low number of antigens on the cell surface or cancer cells that are resistant to treatment. A method for preparing maytansinoids bearing a thioether moiety and a reactive group which allows the maytansinoid to be linked to a cell-binding agent in essentially a single step is also provided.

20 Claims, 52 Drawing Sheets

DM1: R=H, q=1
DM4: R=CH₃, q=2

DM1: R=H, q=1
DM4: R=CH₃, q=2

DM1: R=H, n=1
DM4: R= CH₃, n=2

DM1: R=H, q=1
DM4: R=CH₃, q=2

Time (min)

FIGURE 38
FIGURE 38A
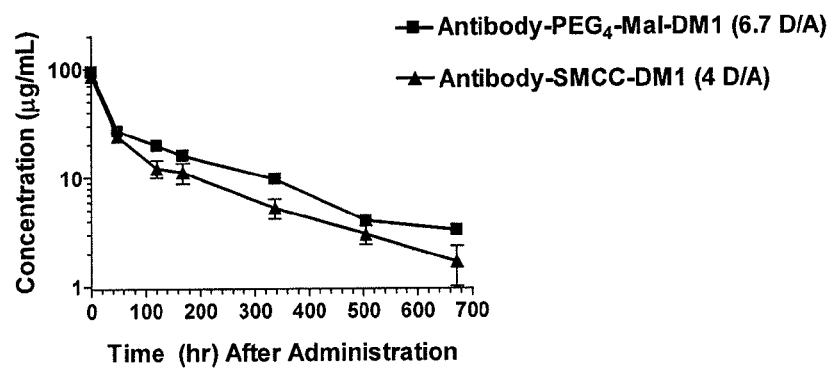
FIGURE 38B
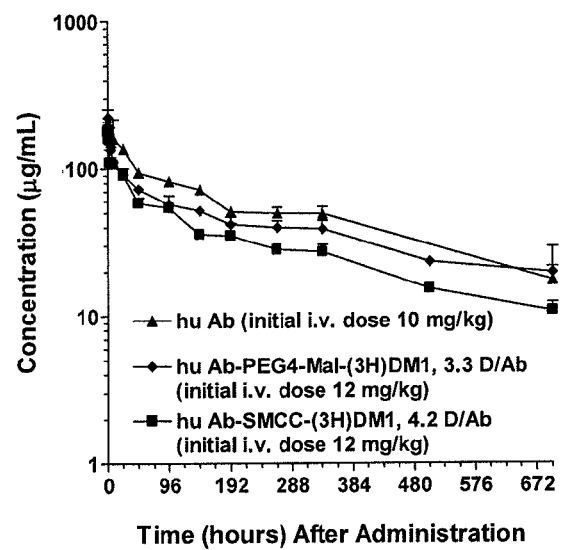

DM1: R=H, q=1
DM4: R=CH₃, q=2

DM1: R=H, n=1
DM4: R=CH₃, n=2

DM1-SMCC: R=H, q=1
DM4-SMCC: R=CH₃, q=2

DM1: R=H, q=1
DM4: R=CH₃, q=2

DM1: R=H, q=1
DM4: R= CH₃, q=2

DM1-SMCC: R=H, q=1
DM4-SMCC: R= CH₃, q=2

DM1: R=H, q=1
DM4: R= CH₃, q=2

AMAS: z=1
BMPS: z=2
GMBS: z=3
DMPS: z=4
EMCS: z=5

DM1-AMAS: R=H, q=1, z=1
DM1-BMPS: R=H, q=1, z=2
DM1-GMBS: R=H, q=1, z=3
DM1-DMPS: R=H, q=1, z=4
DM1-EMCS: R=H, q=1, z=5

DM4-AMAS: R= CH₃, q=2, z=1
DM4-BMPS: R= CH₃, q=2, z=2
DM4-GMBS: R= CH₃, q=2, z=3
DM4-DMPS: R= CH₃, q=2, z=4
DM4-EMCS: R= CH₃, q=2, z=5

DM1: R=H, q=1
DM4: R= CH₃, q=2

X = I or Br

DM1-SBA: R=H, q=1
DM4-SBA: R= CH₃, q=2

DM1: R=H, q=1
DM4: R=CH₃, q=2

X = I or Br

DM1-SBA: R=H, q=1
DM4-SBA: R=CH₃, q=2

DM1: R1=R2=H, q=1
DM4: R1=R2=CH₃, q=2

DM1-Mal-(CH₂)₆-Mal: R1=R2=H, q=1, n=5
DM4-Mal-(CH₂)6-Mal: R1=R2=CH₃, q=2, n=5

DM1: R1=R2=H, q=1
DM4: R1=R2=CH₃, q=2

DM1-Mal-(CH₂)₆-Mal: R1=R2=H, q=1, n=5
DM4-Mal-(CH₂)6-Mal: R1=R2= CH₃, q=2,n=5

POTENT CONJUGATES AND HYDROPHILIC LINKERS

This is a continuation-in-part of U.S. Non-Provisional application Ser. No. 12/433,668, filed Apr. 30, 2009 (abandoned), which claims priority to U.S. Provisional Application No. 61/049,289, filed Apr. 30, 2008. The entire disclosures of the prior applications, application Ser. Nos. 12/433,668 and 61/049,289 are considered part of the disclosure of the accompanying continuing application and are hereby incorporated by reference.

FIELD OF THE INVENTION

The present invention relates to new linkers to link drugs (e.g. cytotoxic agents) to cell-binding agents (e.g., antibodies) in such a way that the linker contributes in increasing the activity of the drug. In particular, the present invention relates to the use of novel hydrophilic linkers, wherein such linkers enhance the potency or the efficacy of the cell-binding agent-drug conjugates by several fold in a variety of cancer cell types, including those expressing a low number of antigens on the cell surface or cancers that are resistant to treatment. The present invention also relates to a method for preparing maytansinoids bearing a thioether moiety and a reactive group which allows the maytansinoid to be linked to a cell-binding agent.

BACKGROUND OF THE INVENTION

Antibody conjugates of cytotoxic drugs are being developed as target-specific therapeutic agents. Antibodies against various cancer cell-surface antigens have been conjugated with different cytotoxic agents that inhibit various essential cellular targets such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; 7,276,497), DNA (calicheamicin, doxorubicin, CC-1065 analogs; U.S. Pat. Nos. 5,475,092; 5,585,499; 5,846,545; 6,534,660; 6,756,397; 6,630,579). Antibody conjugates with some of these cytotoxic drugs are actively being investigated in the clinic for cancer therapy (Richart, A. D., and Tolcher, A. W., 2007, *Nature Clinical Practice*, 4, 245-255).

The antibody-cytotoxic agent conjugates typically are prepared by the initial modification of reactive moieties on antibodies, such as lysine amino groups, or cysteine groups (generated by reduction of native disulfide bonds or by engineering of additional non-native cysteine residues on to antibodies using molecular biology methods). Thus antibodies are first modified with a heterobifunctional linker reagent, such as those previously described, exemplified by SPDB, SMCC and SIAB (U.S. Pat. No. 6,913,758 and U.S. Patent Publication No. 20050169933) to incorporate a linker with a reactive group such as mixed pyridyldisulfide, maleimide or haloacetamide. The incorporated reactive linker group in the antibody is subsequently conjugated with a cytotoxic agent containing a reactive moiety such as a thiol group. Another conjugation route is by reaction of a cytotoxic agent derivative containing a thiol-reactive group (such as haloacetamide, or maleimide) with thiol groups on the cell-binding agent. Thiol groups are incorporated on cell-binding agents such as an antibody by reduction of native disulfide residues (R. Singh et al., *Anal. Biochem.*, 2002, 304, 147-156), or reduction of incorporated disulfide moieties (via SPDP, succinimidyl 3-(2-pyridyldithio)propionate, followed by reduction with dithiothreitol, D. G. Gilliland et al., *Proc. Natl. Acad. Sci. USA.*, 1980, 77, 4539-4543), or by incorporation of additional non-native cysteine residues (J. B. Stimmel et al., *J. Biol. Chem.*, 2000, 275, 30445-30450), or incorporation of thiol groups by reaction with 2-iminothiolane (R. Jue et al., *Biochemistry*, 1978, 17, 5399-5406), or methyl 3-mercaptopropionimidate ester (T. P. King et al., *Biochemistry*, 1978, 17, 1499-1506).

The antibody-cytotoxic agent conjugates with disulfide or thioether linkages are cleaved intracellularly, presumably in lysosomes, to deliver the active cytotoxic agent inside the cancer cell (H. K. Erickson et al., 2006, *Cancer Research*, 66, 4626-4433). In addition to the killing of target cells, antibody-cytotoxic agent conjugates with reducible disulfide linkage also kill proximate antigen-negative cells in mixed populations of antigen-negative and antigen-positive cells in vitro and in vivo in xenograft models, suggesting the role of target-cell released cytotoxic agent in improving potency against neighboring non-antigen-expressing cells in tumors with heterogeneous antigen expression (Y. V. Kovtun et al., *Cancer Research*, 2006, 66, 3214-3221).

Although, antibody-cytotoxic drug conjugates show cell killing activity in vitro and anti-tumor activity in vivo, their potency is diminished in many cases, especially when the antigen expression on the target cancer cell is low, or when the target cells are resistant to the treatment. This is often the case in the clinical setting, resulting in low to modest anti-tumor activity in patients. A potential approach to try to circumvent resistance is to synthesize new drugs that bear hydrophilic or lipophobic functionalities (see G. Szokacs et al., *Nature Reviews*, 5; 219-235, 2006). However, this process is cumbersome and several analogs have to be synthesized, and often modification in the structure of the drug results in loss of biological activity. Thus, there is a need for a different approach.

The method described in the art for preparing a cytotoxic conjugate of a cell binding agent and a drug via non-cleavable linker requires two reaction steps (U.S. Pat. No. 5,208,020 & US Publication No. 2005/0169933). First, the cell binding agent, such as an antibody, is modified with a bifunctional crosslinker that undergoes reaction with the reactive groups of the cell binding agent, such as the amine group on lysine residues or the sulfhydryl group on cysteine residues, to form covalent chemical bonds. Following modification of the cell binding agent, the product is purified to separate the desired modified cell binding agent from unreacted crosslinker. In a second step, known as a conjugation step, a reactive drug derivative, such as a thiol-containing maytansinoid, is added to the modified cell-binding agent for reaction with the modified cell-binding agent. Following this reaction, an additional purification is required to remove any unreacted drug species and other byproducts from the final conjugate. These multiple reaction and purification steps result in low yield of the final conjugate and can be expensive and cumbersome when one considers implementing these steps on a large scale. An additional drawback to these methods is the conjugate heterogeneity that is introduced when unreacted crosslinker remains linked to the cell-binding agent without attached drug. The unreacted crosslinker can then undergo additional side reactions such as hydrolysis and intramolecular or intermolecular reactions. There is therefore a need for functionalized, reactive drug derivatives, such as maytansinoids, that can be covalently linked via a non-cleavable bond to a cell binding agent, such as an antibody in essentially one reaction step.

SUMMARY OF THE INVENTION

The present invention addresses the problem of resistance by designing new linkers to link drugs to cell-binding agents in such a way that the linker contributes in increasing the activity of the drug. Thus, the present invention improves the manner in which drugs are linked to a cell-binding agent such that the linker design provides conjugates that are active across a broad spectrum of tumors, particularly in low antigen expressing or drug resistant tumors.

The present invention is based on the novel finding that when traditional linkers (e.g. SMCC, SIAB etc, described in U.S. Patent Publication No. 20050169933) are modified to hydrophilic linkers by incorporating a polyethylene glycol [$PEG_n$, $(\text{—}CH_2CH_2O\text{—})_n)$] spacer, the potency or the efficacy of the cell-binding agent-drug conjugates is surprisingly enhanced several fold in a variety of cancer cell types, including those expressing a low number of antigens on the cell surface.

Also, these PEG-containing conjugates unexpectedly are more potent than the previously described conjugates toward cell lines that are resistant to treatment.

In addition, in the case of antibody conjugates, incorporation of hydrophilic linkers allowed the conjugation of up to 15 molecules of a drug per antibody molecule with high yield and no aggregation or precipitation. These conjugates with hydrophilic linkers with up to 15 molecules of a drug linked per antibody molecule bound with high affinity to target antigen (similar to that of unmodified antibody).

This invention also discloses novel maytansinoids that are reactive towards amine groups or thiol groups of cell binding agents such that thioether-linked maytansinoid conjugates with cell binding agents may be prepared in essentially one reaction step, without prior chemical modification of the cell binding agent.

The present invention discloses processes for the synthesis of novel maytansinoid derivatives bearing a thioether-moiety and a reactive group. These novel maytansinoids are useful in the preparation of thioether-linked conjugates with cell binding agents in essentially one reaction step. Processes for the preparation of cell binding agent conjugates employing these novel reactive maytansinoids are also disclosed.

Accordingly, the present invention provides a compound of formula (1) or a specific compound of formula (1'):

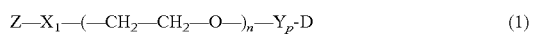  (1)

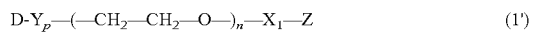  (1')

wherein:
Z represents a reactive functionality that can form an amide or a thioether bond with a cell-binding agent;
D represents a drug;
X represents an aliphatic, an aromatic or a heterocyclic group attached to the cell-binding agent via a thioether bond, an amide bond, a carbamate bond, or an ether bond;
Y represents an aliphatic, an aromatic or a heterocyclic group attached to the drug via a covalent bond selected from the group consisting of a thioether bond, an amide bond, a carbamate bond, an ether bond, an amine bond, a carbon-carbon bond and a hydrazone bond;
l is 0 or 1;
p is 0 or 1; and
n is an integer from 1 to 2000.

Another aspect of the present invention is a cell-binding agent drug conjugate of formula (2) or a specific compound of formula (2'):

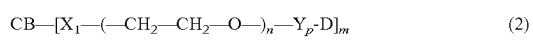  (2)

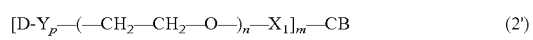  (2')

wherein, CB represents a cell-binding agent;
D represents a drug;
X represents an aliphatic, an aromatic or a heterocyclic group attached to the cell-binding agent via a thioether bond, an amide bond, a carbamate bond, or an ether bond;
Y represents an aliphatic, an aromatic or a heterocyclic group attached to the drug via a covalent bond selected from the group consisting of a thioether bond, an amide bond, a carbamate bond, an ether bond, an amine bond, a carbon-carbon bond and a hydrazone bond;
l is 0 or 1;
p is 0 or 1;
m is an integer from 2 to 15; and
n is an integer from 1 to 2000.

Another aspect of the present invention is a compound of formula (3) or a specific compound of formula (3'):

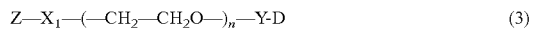  (3)

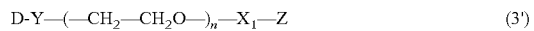  (3')

wherein:
Z represents a reactive functionality that can form an amide or a thioether bond with a cell-binding agent;
D represents a drug;
X represents an aliphatic, an aromatic or a heterocyclic group attached to the cell-binding agent via a thioether bond, an amide bond, a carbamate bond, or an ether bond;
Y represents an aliphatic, non-aromatic heterocyclic or aromatic heterocyclic group attached to the drug via a disulfide bond;
l is 0 or 1; and
n is an integer from 1 to 14.

Another aspect of the present invention is a cell-binding agent drug conjugate of formula (4) or a specific compound of formula (4'):

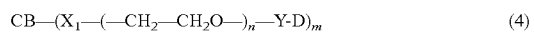  (4)

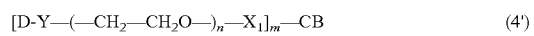  (4')

wherein, CB represents a cell-binding agent;
D represents a drug;
X represents an aliphatic, an aromatic or a heterocyclic group attached to the cell-binding agent via a thioether bond, an amide bond, a carbamate bond, or an ether bond;
Y represents an aliphatic, an aromatic or a heterocyclic group attached to the drug via a disulfide bond;
l is 0 or 1; and
m is an integer from 3 to 8; and
n is an integer from 1 to 14.

An even further aspect of the present invention is a method for treating cancer sensitive to treatment with said method, said method comprising parenterally administering to a patient in need thereof an effective dose of a composition comprising the conjugate of formula (2) or (4).

In still another aspect of the present invention, there is provided novel maytansinoids having a thioether moiety that bears a reactive group and that are represented by the formula (5):

  (5)

wherein:
D' represents a sulfhydryl-bearing maytansinoid, such as $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl) maytansine (DM4);
Y' represents a thioether bond
V is an optional linear, branched or cyclic alkyl, alkenyl or alkynyl group having from 1 to 10 carbon atoms;

Q represents an optional aromatic or a heterocyclic moiety;
W is an optional linear, branched or cyclic alkyl, alkenyl or alkynyl group having from 1 to 10 carbon atoms; and
Z' represents an amine or sulfhydryl reactive group.

The reactive maytansinoid derivative bearing a thioether moiety is prepared from a sulfhydryl-bearing maytansinoid (such as DM1 and DM4) and a heterobifunctional crosslinker. The reaction is represented by the following chemical equation:

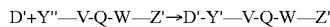
$$D'+Y''\text{—}V\text{-}Q\text{-}W\text{—}Z' \rightarrow D'\text{-}Y'\text{—}V\text{-}Q\text{-}W\text{—}Z'$$

wherein:
D' represents a sulfhydryl-bearing maytansinoid such as $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl) maytansine (DM4);
V is an optional linear, branched or cyclic alkyl, alkenyl or alkynyl group having from 1 to 10 carbon atoms;
Q represents an optional aromatic or a heterocyclic moiety;
W is an optional linear, branched or cyclic alkyl, alkenyl or alkynyl group having from 1 to 10 carbon atoms;
Z' is an amine or sulfhydryl reactive group;
Y" represents a sulfhydryl-reactive moiety; and
Y' represents a thioether bond between the sulfhydryl-bearing maytansinoid and the crosslinker.

The present invention also discloses a process for the preparation of cytotoxic conjugates of maytansinoids and cell binding agents linked via a non-cleavable bond (formula 10), said process comprising reacting a cell binding agent with a compound of formula Z'—W-Q-V—Y'-D' to provide a cell binding agent conjugate of formula CB—(Z"—W-Q-V—Y'-D')$_m$
wherein,
Z' represents an amine or sulfhydryl reactive group;
W is an optional linear, branched or cyclic alkyl, alkenyl or alkynyl group having from 1 to 10 carbon atoms;
Q represents an optional aromatic or a heterocyclic moiety;
V is an optional linear, branched or cyclic alkyl, alkenyl or alkynyl group having from 1 to 10 carbon atoms;
Y' represents a thioether bond;
D' represents a sulfhydryl bearing maytansinoid, such as $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl) maytansine (DM4);
CB represents a cell-binding agent;
Z" represents an amide bond; and
m is an integer from 2 to 8.

The cell-binding agent maytansinoid conjugate may be further purified.

BRIEF DESCRIPTION OF THE DRAWINGS

FIG. 38 shows plasma pharmacokinetics of Antibody-PEG4-Mal-DM1 in CD-1 mice: 38A Antibody-PEG4-Mal-DM1 conjugate with 6.7 D/A compared to Antibody-SMCC-DM1 conjugate with 4 D/A (initial i.v. dose 5 mg/kg); 38B Antibody-PEG4-Mal-(3H-labeled)DM1 conjugate with 3.3 D/A compared with unmodified antibody and Antibody-SMCC-(3H-labeled)DM1 conjugate with 4.2 D/A (initial i.v. dose 10-12 mg/kg).

DETAILED DESCRIPTION OF THE INVENTION

Figure 1:
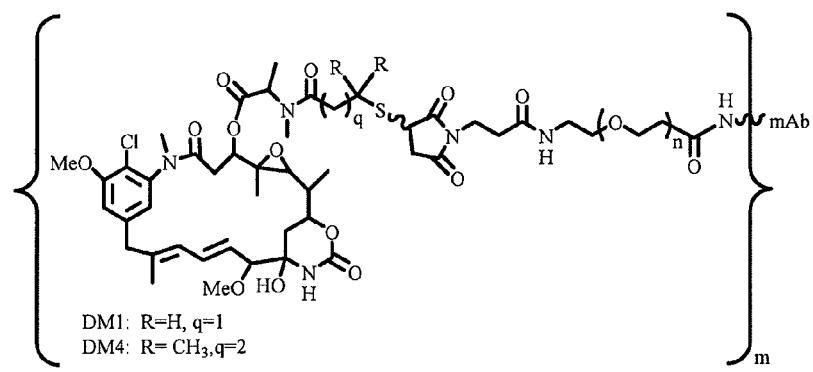
FIG. 1 shows a structural representation of representative PEG-containing thiosuccinimidyl-linked conjugates of the present invention (mAb=monoclonal antibody; n=1-2000; m=2-15).

This invention discloses the novel findings that conjugates of cell-binding agents, such as an antibody, linked to drugs, for example, cytotoxic agents, by polyethylene glycol or polyethylene oxide linkers ($(—CH_2CH_2O)_n$) exhibit several fold greater cytotoxicity toward target cancer cells than expected based on comparison with traditional cell-binding agent drug conjugates with typical aliphatic linkers and similar drug loads. Importantly, the conjugates described in this invention are highly potent or efficacious toward cancer cells that are multidrug resistant (mdr), which have poor sensitivity to treatment with cytotoxic drugs. Cancer therapy poses the hurdle of overcoming mechanisms of drug resistance often encountered after multiple rounds of treatment with different chemotherapeutic agents. One such mechanism observed in cancer cells called multidrug resistance is caused by enhanced export of drugs by ATP-binding cassette (ABC) transporters (C. Drumond, B. I. Sikic, *J. Clin. Oncology*, 1999, 17, 1061-1070, G, Szokacs et al., *Nature Reviews*, 5; 219-234, 2006). Therapies that overcome these mechanisms of drug resistance, such as interfering with or overcoming this efflux of drugs by cancer cells would be highly useful. The cytotoxicity of the PEG-linked conjugates of cell-binding agents and cytotoxic drugs were evaluated against multidrug resistant cancer cells to test if the PEG-linkers confer any advantage against these resistant cells. In these assays against mdr cells, the PEG linked conjugates of cell-binding agents and cytotoxic drugs showed unexpectedly potent cell killing of the mdr cells in comparison to the much less potent conjugates derived from conventional linkers. In addition, the conjugates of the present invention also display markedly higher anti-tumor activity in animal models established with multidrug resistant tumor cells.

The use of hydrophilic polyethylene glycol or polyethylene oxide linkers (PEG or PEO; $(—CH_2CH_2O)_n$) also allows the incorporation of a relatively large number of drugs per cell-binding agent molecule with the high protein monomer level of greater than 90% at concentrations of greater than 1 mg/ml that are desired for therapeutic uses. Furthermore, the polyethylene glycol (PEG)-linked conjugates of cell-binding agents having a range of cytotoxic drug load (from a small value of 2 to a large number such as 15 drugs linked per cell-binding agent) showed greatly enhanced cytotoxicities toward target cancer cells than expected from the stoichiometric increase in drug delivery based on increased drug load of the conjugates. Conjugates of cell-binding agent and drug having PEG spacers are described in this invention, which exhibited the super-stoichiometric increase in cytotoxicity toward target cancer cells by as much as a 260-650 fold enhancement in potency (see, for example, FIG. 29) as compared to traditionally prepared conjugates with similar drug loads.

Therefore, in one aspect of the invention, drugs with linkers having a polyethylene glycol spacer ($-CH_2CH_2O-$)$_n$ and a reactive group capable of reacting with a cell-binding agent are described.

Specifically contemplated in this aspect is a modified compound of formula (1) or a specific compound of formula (1'):

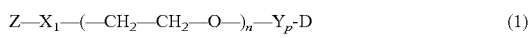

$$Z-X_l-(-CH_2-CH_2-O-)_n-Y_p-D \qquad (1)$$

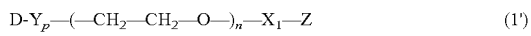

$$D-Y_p-(-CH_2-CH_2-O-)_n-X_l-Z \qquad (1')$$

wherein:
Z represents a reactive functionality that can form an amide or a thioether bond with a cell-binding agent;
D represents a drug;
X represents an aliphatic, an aromatic or a heterocyclic group attached to the cell-binding agent via a thioether bond, an amide bond, a carbamate bond, or an ether bond;
Y represents an aliphatic, an aromatic or a heterocyclic group attached to the drug via a covalent bond selected from the group consisting of a thioether bond, an amide bond, a carbamate bond, an ether bond, an amine bond, a carbon-carbon bond and a hydrazone bond;
l is 0 or 1;
p is 0 or 1; and
n is an integer from 1 to 2000.

Preferably, the covalent bond that attaches Y to the drug is a thioether bond or an amide bond.

Preferably n is an integer from 1 to 100. Even more preferably, n is an integer from 1 to 14. In the most preferable aspect n is an integer from 1 to 4.

In a second aspect of the invention, novel conjugates of cell-binding agents and drugs with polyethylene glycol linkers ($-CH_2CH_2O-$)$_n$ are described. These conjugates are more potent toward cancer cells than conjugates with traditional linkers and equivalent drug loads.

Specifically contemplated in a preferred aspect is a conjugate of a cell-binding agent and a drug of formula (2) or a specific compound of formula (2'):

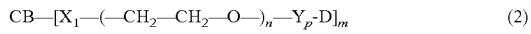

$$CB-[X_l-(-CH_2-CH_2-O-)_n-Y_p-D]_m \qquad (2)$$

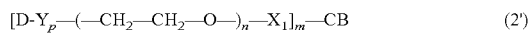

$$[D-Y_p-(-CH_2-CH_2-O-)_n-X_l]_m-CB \qquad (2')$$

wherein:
CB represents a cell-binding agent;
D represents a drug;
X represents an aliphatic, an aromatic or a heterocyclic group attached to the cell-binding agent via a thioether bond, an amide bond, a carbamate bond, or an ether bond;
Y represents an aliphatic, an aromatic or a heterocyclic group attached to the drug via a covalent bond selected from the group consisting of a thioether bond, an amide bond, a carbamate bond, an ether bond, an amine bond, a carbon-carbon bond and a hydrazone bond;
l is 0 or 1;
p is 0 or 1; and
m is an integer from 2 to 15; and
n is an integer from 1 to 2000.

Preferably, the covalent bond is a thioether bond or an amide bond.

Preferably, m is an integer from 3 to 8.

Preferably n is an integer from 1 to 100. Even more preferably, n is an integer from 1 to 14. In the most preferable aspect, n is an integer from 1 to 4.

The present invention is also based on the novel finding that in the case of antibody conjugates, wherein the antibody is linked to cytotoxic drugs via disulfide bonds, there is a critical correlation between the number of drugs linked and the length of the polyethylene glycol spacer in enhancing the potency or the efficacy of the immunoconjugate. The additional benefit of this linker design is the desired high monomer ratio and the minimal aggregation of the antibody-drug conjugate. Thus, in one aspect, the present invention is based on the critical finding that when the polyethylene glycol spacer for a disulfide-linked conjugate consists of between 2 and 8 ethyleneoxy groups and the number of drugs linked ranges from 3 to 8, it gives antibody-drug conjugates the highest biological potency or efficacy and also gives the desired high monomer content.

In a preferred aspect, cytotoxic drugs linked via disulfide group ($-S-S-$) having short polyethylene glycol spacers (($CH_2CH_2O$)$_{n=1-14}$) with a functional group capable of reaction with a cell-binding agent are described.

Specifically contemplated in this aspect is a modified cytotoxic compound of formula (3) or a specific compound of formula (3'):

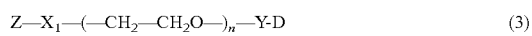

$$Z-X_l-(-CH_2-CH_2O-)_n-Y-D \qquad (3)$$

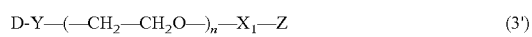

$$D-Y-(-CH_2-CH_2O-)_n-X_l-Z \qquad (3')$$

wherein;
Z represents a reactive functionality that can form an amide or a thioether bond with a cell-binding agent;
D represents a drug;
X represents an aliphatic, an aromatic or a heterocyclic group attached to the cell-binding agent via a thioether bond, an amide bond, a carbamate bond, or an ether bond;
Y represents an aliphatic, non-aromatic heterocyclic or aromatic heterocyclic group attached to the drug via a disulfide bond;
l is 0 or 1; and
n is an integer from 1 to 14.

Preferably, n is an integer from 2 to 8.

In another preferred aspect, conjugates of cell-binding agents and drugs linked via disulfide group ($-S-S-$) having polyethylene glycol spacers (($CH_2CH_2O$)$_{n=1-14}$) with a narrow range of drug load of 3-8 are described that show relatively high potent biological activity toward cancer cells and have the desired biochemical properties of high conjugation yield and high monomer ratio with minimal protein aggregation.

Specifically contemplated in this aspect is a cell-binding agent drug conjugate of formula (4) or a specific compound of formula (4'):

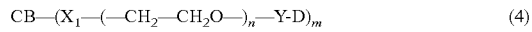

$$CB-(X_l-(-CH_2-CH_2O-)_n-Y-D)_m \qquad (4)$$

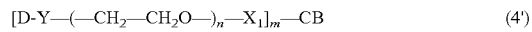

$$[D-Y-(-CH_2-CH_2O-)_n-X_l]_m-CB \qquad (4')$$

wherein:

CB represents a cell-binding agent;

D represents a drug;

X represents an aliphatic, an aromatic or a heterocyclic group attached to the cell-binding agent via a thioether bond, an amide bond, a carbamate bond, or an ether bond;

Y represents an aliphatic, an aromatic or a heterocyclic group attached to the drug via a disulfide bond;

l is 0 or 1;

m is an integer from 3 to 8; and n is an integer from 1 to 14.

Preferably, m is an integer from 3 to 6.

Also, preferably, n is an integer from 2 to 8.

In this invention, drugs are lipophilic molecules, which when conjugated to cell-binding agents such as antibodies often result in loss of yield due to protein aggregation or precipitation. Increasing the number of drugs per cell-binding agent typically results in worse protein aggregation and precipitation, and subsequent poor monomer percentage and low yields. In contrast to the typical conjugate behavior with conventional linkers, the PEG linkers result in a desirable improvement in monomer percentage (>90% monomer) and yield (>70%) of the conjugates of cell-binding agents with drugs at high concentrations of 1 mg/ml or greater that are useful for therapeutic applications. In addition, these conjugates are stable upon prolonged storage at 4° C.

In the present invention, novel maytansinoids having a thioether moiety that bears a reactive group are disclosed such that those compounds are represented by the formula (5):

D'-Y'—V-Q-W—Z'    (5)

wherein:

V is an optional linear, branched or cyclic alkyl, alkenyl or alkynyl group preferably having from 1 to 10 carbon atoms; more preferably a linear alkyl having 1-5 carbon atoms, and still more preferably V is a one carbon alkyl group ($CH_2$);

W is an optional linear, branched or cyclic alkyl, alkenyl or alkynyl group having from 1 to 10 carbon atoms; more preferably having 2-8 carbon atoms, still more preferably W is a cyclohexyl group;

D' represents a sulfhydryl-bearing maytansinoid, and more preferably it is selected from DM1, DM3 and DM4;

Y' represents a thioether bond

Q represents an optional aromatic or a heterocyclic moiety, and preferably Q is absent Z' represents an amine reactive group or a thiol reactive group selected from, but not limited to, a N-hydroxy succinimide ester, N-hydroxysulfosuccinimide ester, para or ortho-nitro phenyl ester, dinitrophenyl ester, pentafluorophenyl ester and sulfo-tetrafluorophenyl ester; a maleimide or a haloacetamide, more preferably Z is a N-hydroxysuccinimide, N-hydroxysulfosuccinimide ester or a maleimide.

In another embodiment, reactive maytansinoid derivatives bearing a thioether moiety are prepared from a sulfhydryl-bearing maytansinoid (such as DM1 and DM4) and a heterobifunctional crosslinker. The reaction sequence is represented by formula (6):

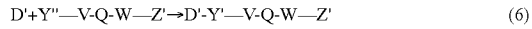

D'+Y"—V-Q-W—Z'→D'-Y'—V-Q-W—Z'    (6)

wherein:

V is an optional linear, branched or cyclic alkyl, alkenyl or alkynyl group preferably having from 1 to 10 carbon atoms; more preferably a linear alkyl having 1-5 carbon atoms, and still more preferably V is a one carbon alkyl group ($CH_2$);

W is an optional linear, branched or cyclic alkyl, alkenyl or alkynyl group having from 1 to 10 carbon atoms; more preferably having 2-8 carbon atoms, still more preferably W is a cyclohexyl group;

Y" represents a thiol-reactive groups elected from maleimide or haloacetamide, preferably a maleimide;

D' represents a sulfhydryl-bearing maytansinoid, and more preferably it is selected from DM1, DM3 and DM4;

Y' represents a thioether bond

Q represents an optional aromatic or a heterocyclic moiety, and preferably Q is absent Z' represents an amine reactive group or a thiol reactive group selected from, but not limited to, a N-hydroxy succinimide ester, N-hydroxysulfosuccinimide ester, para or ortho-nitro phenyl ester, dinitrophenyl ester, pentafluorophenyl ester and sulfo-tetrafluorophenyl ester; a maleimide or a haloacetamide, more preferably Z is a N-hydroxysuccinimide, N-hydroxysulfosuccinimide ester or a maleimide.

Y' represents a thioether bond.

The invention also provides a process for the preparation of cytotoxic conjugates of maytansinoids and cell binding agents linked via a non-cleavable bond said process comprising reacting a cell binding agent with a compound of formula Z'—W-Q-V—Y'-D' to provide a cell binding agent conjugate of formula CB—(Z"—W-Q-V—Y'-D')$_m$.

wherein:

W is an optional linear, branched or cyclic alkyl, alkenyl or alkynyl group having from 1 to 10 carbon atoms; more preferably having 2-8 carbon atoms, still more preferably W is a cyclohexyl group;

Q represents an optional aromatic or a heterocyclic moiety, and preferably Q is absent;

V is an optional linear, branched or cyclic alkyl, alkenyl or alkynyl group preferably having from 1 to 10 carbon atoms; more preferably a linear alkyl group having 1-5 carbon atoms, and still more preferably V is a one carbon alkyl group ($CH_2$);

Y' represents a thioether bond;

D' represents a sulfhydryl-bearing maytansinoid, and more preferably it is selected from DM1, DM3 and DM4;

CB represents a cell binding agent selected from an antibody, a single chain antibody, an antibody fragment, a peptide, growth factor, hormone, vitamin, or ankyrin repeat proteins (DARPins), preferably the cell binding agent is an antibody or an antibody fragment or a Darpin;

Z' represents an amine reactive group or a thiol reactive group selected from, but not limited to, a N-hydroxy succinimide ester, N-hydroxysulfosuccinimide ester, para or ortho-nitro phenyl ester, dinitrophenyl ester, pentafluorophenyl ester and sulfo-tetrafluorophenyl ester; a maleimide or a haloacetamide, more preferably Z is a N-hydroxysuccinimide, N-hydroxysulfosuccinimide ester or a maleimide;

Z" represents a thioether bond or an amide bond;

The process can be conducted by mixing a solution of the cell binding agent, such as an antibody, in aqueous buffer, optionally containing up to 20% organic solvent. with the compound of formula Z'—W-Q-V—Y'-D' in organic solvent or a mixture of organic solvent and aqueous buffer or water, and allowing the reaction to proceed for between 5 min to 72 hours.

the conjugate can be further purified by chromatography, dialysis, tangential flow filtration or a combination of these In all aspects, an "aliphatic group" is defined as alkyl, alkenyl or alkynyl group. An alkyl group is an aliphatic hydrocarbon group which may be straight or branched, preferably having 1 to 20 carbon atoms in the chain or cyclic, preferably having 3 to 10 carbon atoms. More preferred alkyl groups have 1 to 12 carbon atoms in the chain. "Branched"

means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl and cyclohexyl.

An alkenyl group is an aliphatic hydrocarbon group containing a carbon-carbon double bond and which may be straight or branched, preferably having 2 to 15 carbon atoms in the chain. More preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

An alkynyl group is an aliphatic hydrocarbon group containing a carbon-carbon triple bond and which may be straight or branched, preferably having 2 to 15 carbon atoms in the chain. More preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

As used herein, the term "aromatic group" means a substituted or unsubstituted aryl group consisting of an aromatic monocyclic or multicyclic hydrocarbon ring system of 6 to 14 carbon atoms, preferably of 6 to 10 carbon atoms. Exemplary aryl groups include phenyl and naphthyl. Substituents include, but are not limited to, alkyl groups, halogens, nitro, amino, hydroxyl and alkoxy groups.

Halogens include fluorine, chlorine, bromine and iodine atoms. Fluorine and chlorine atoms are preferred.

As used herein, the term "heterocyclic group" refers to a saturated, partially unsaturated or unsaturated, non-aromatic stable 3 to 14, preferably 5 to 10 membered mono, bi or multicyclic rings wherein at least one member of the ring is a hetero atom, or an aromatic, preferably 5 to 10 membered mono-, bi- or multicyclic ring having at least one hetero atom. Typically, hetero atoms include, but are not limited to, oxygen, nitrogen, sulfur, selenium, and phosphorus atoms. Preferable hetero atoms are oxygen, nitrogen and sulfur.

Preferred heterocyclic groups include, but are not limited to, pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydro-pyranyl, tetrahydropyranyl, dihydropyranyl, tetrahydro-pyridyl, dihydropyridyl, tetrahydropyrimidinyl, dihydrothiopyranyl, azepanyl, pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, and isoxazolyl, pyridyl-N-oxide, as well as fused systems resulting from the condensation with a phenyl group.

The aliphatic, aromatic and heterocyclic groups represented by X and Y can also possess a charged substituent. The charged substituent can be negatively charged selected from, but not limited to carboxylate, sulfonate and phosphates, or positively charged selected from a tertiary or quaternary amino group.

As used herein, the expression "linked to a cell-binding agent" refers to the conjugate molecule comprising at least one drug derivative bound to a cell-binding agent via a suitable linking group, or a precursor thereof. Preferred linking groups are thiol or disulfide bonds, or precursors thereof.

As used herein, "precursor" of a given group refers to any group which may lead to that group by any deprotection, chemical modification, or coupling reaction. For example a precursor could be an appropriately protected functionality exemplified by a thioester or thioether as a thiol precursor.

As used herein, the term "reactive functionality" refers to an amine-, a thiol- or a hydroxyl-reactive functionality. In other words, the reactive functionality can react with amine, sulfhydryl(thiol), or hydroxyl group present on cell-binding agent. For example, for amine-reactive functionality, the functionality could be a reactive carboxylic ester (including N-succinimidyl, N-sulfosuccinimidyl, N-phthalimidyl, N-sulfophthalimidyl, 2-nitrophenyl, 4-nitrophenyl, 2,4-dinitrophenyl, 3-sulfo-4-nitrophenyl, 3-carboxy-4-nitrophenyl, tetrafluorophenyl esters), a reactive sulfonic acid derivative, or a reactive thioester to give an amide bond; for thiol-reactive functionality, the functionality could be a maleimide, a haloacetamide, or a vinyl sulfone to give a thioether bond; and, for hydroxyl-reactive functionality, the functionality could be a reactive carboxylic ester to give an ester bond.

A. Modified Drugs and Modified Cell Binding Agents Having Hydrophilic Linkers

Figure 2:
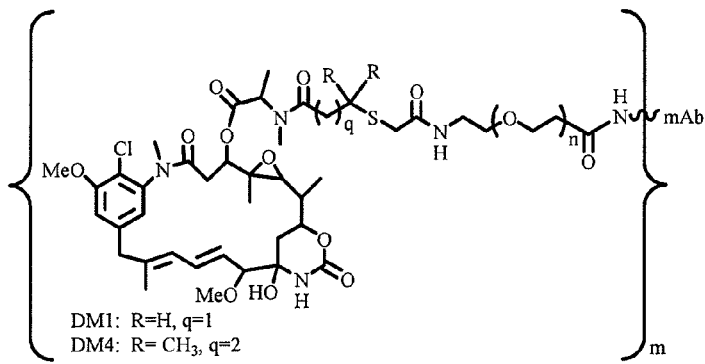
FIG. 2 shows a structural representation of representative PEG-containing thioacetamidyl-linked conjugates of the present invention (n=1-2000; m=2-15).
Figure 3:
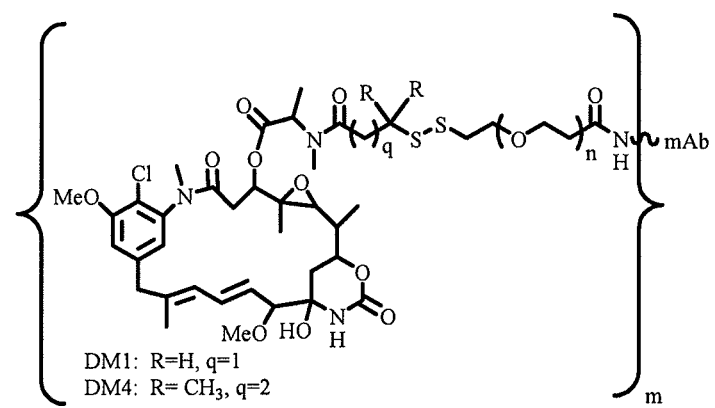
FIG. 3 shows a structural representation of representative PEG-containing disulfide linked compounds of the present invention (n=1-14; m=3-8).

A linker is any chemical moiety that is capable of linking a drug, such as a maytansinoid, to a cell-binding agent in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the drug or the cell-binding agent remains active. FIGS. 1, 2 and 3 exemplarily provide structural representations of conjugates of the present invention.

Figure 13:
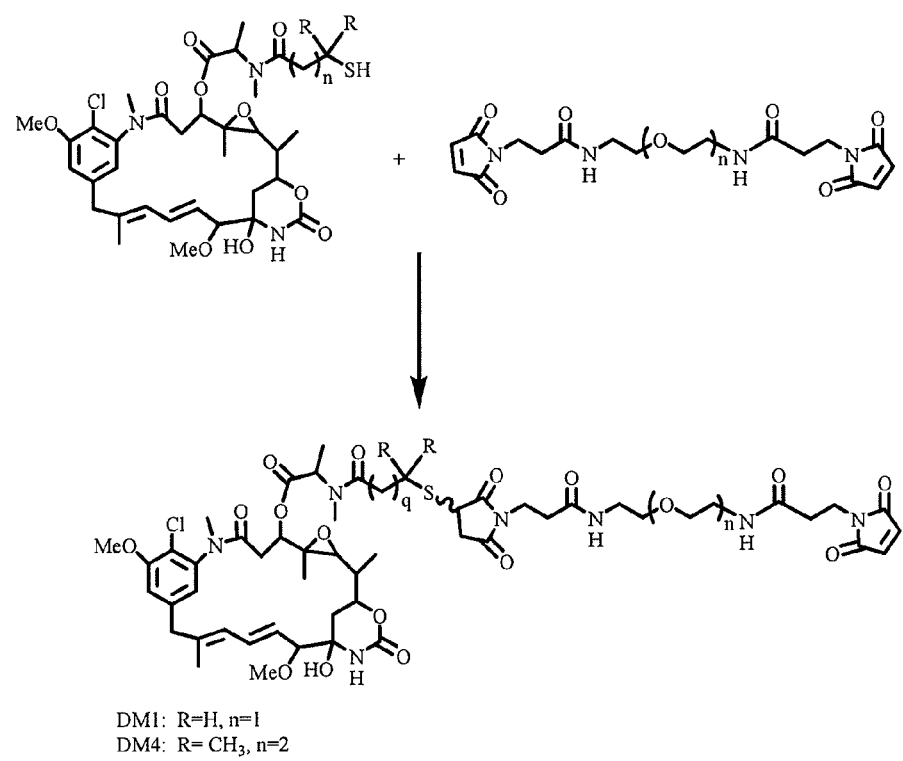
FIG. 13 shows a synthetic scheme for PEG-containing, sulfhydryl-reactive, thiosuccinimidyl-linked compounds of the present invention (n=1-2000).
Figure 14:
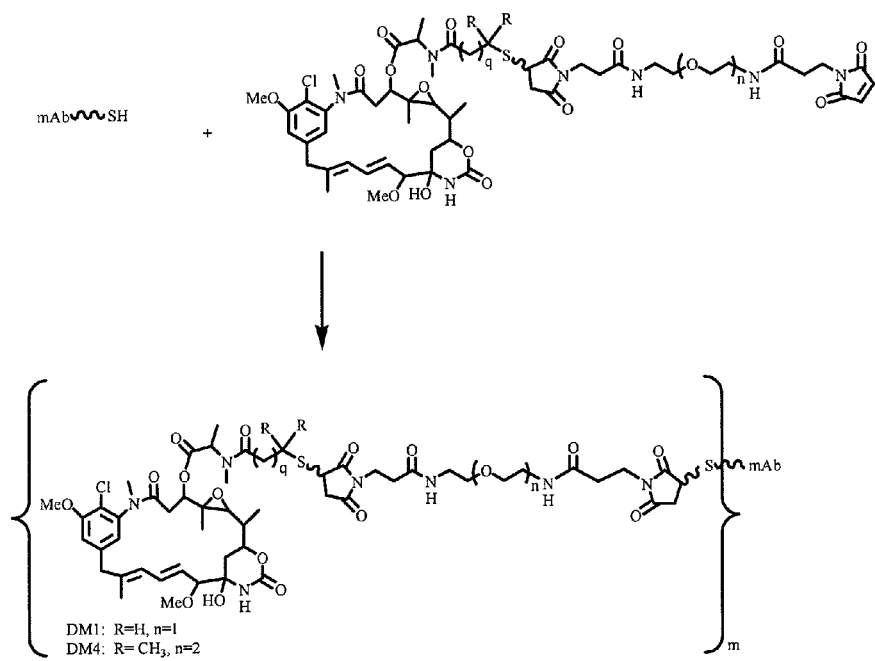
FIG. 14 shows a conjugation procedure for PEG-containing thiosuccinimidyl-linked conjugate of the present invention (1-step conjugation; n=1-2000; m=2-15).

Suitable crosslinking reagents comprising hydrophilic PEG chains that form linkers between a drug and the cell-binding agent are well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of formula (1), Z—$X_1$—(—$CH_2$—$CH_2$—O—)$_n$—$Y_p$-D, by methods described herein. For example, a thiol-containing maytansinoid drug can be reacted with a bis-maleimido crosslinking agent having a PEG spacer to give a maytansinoid drug linked via a thioether bond to the PEG spacer (see for example FIG. 13). This modified maytansinoid having a PEG spacer and a terminal maleimido group can then be reacted with a cell binding agent as shown for example in FIG. 14, to provide a cell binding agent-drug conjugate of formula (2) of the present invention.

Figure 15:
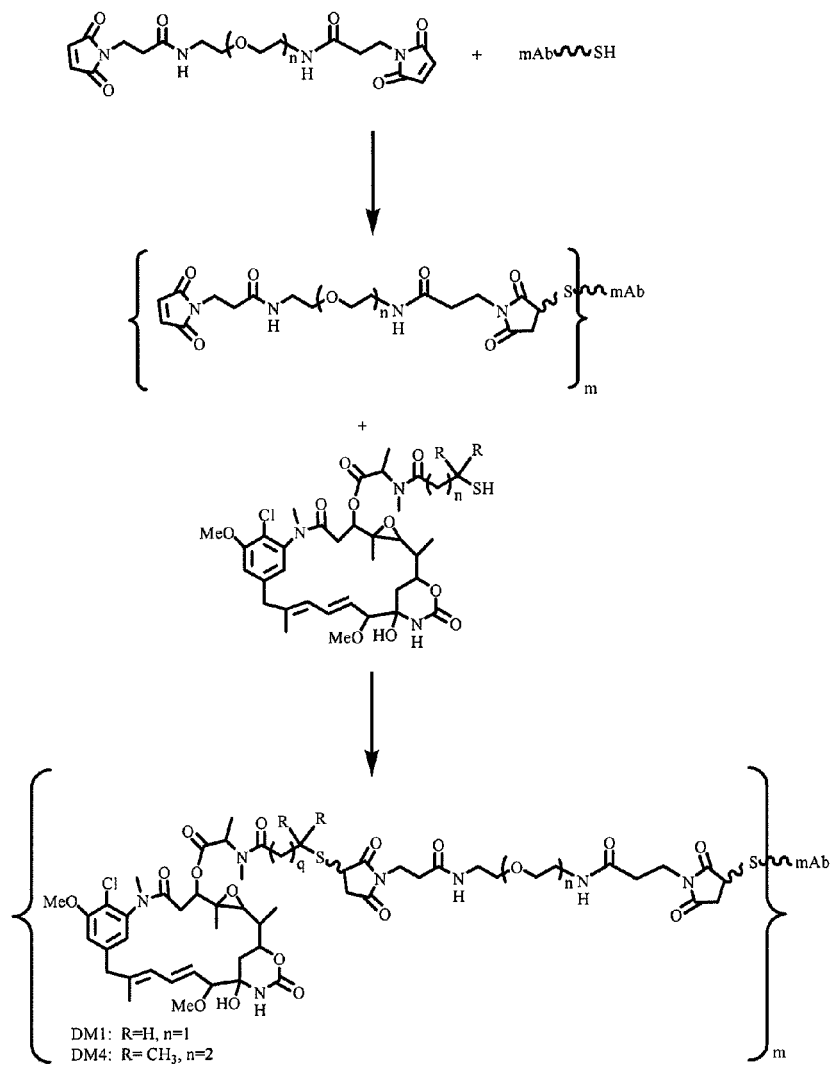
FIG. 15 shows a conjugation procedure for PEG-containing, thiosuccinimidyl-linked conjugate of the present invention (2-step conjugation; n=1-2000; m=2-15).

Alternatively, the cell binding agent can be first reacted at one end of the bifunctional PEG containing cross linker bearing an amine reactive group, such as a N-hydroxysuccinimide ester, to give a modified cell binding agent covalently bonded to the linker through an amide bond (see for example FIG. 15). In the next step the maytansinoid reacts with the maleimido substituent on the other end of the PEG spacer to give a cell-binding agent-drug conjugate of the present invention.

Figure 16A:
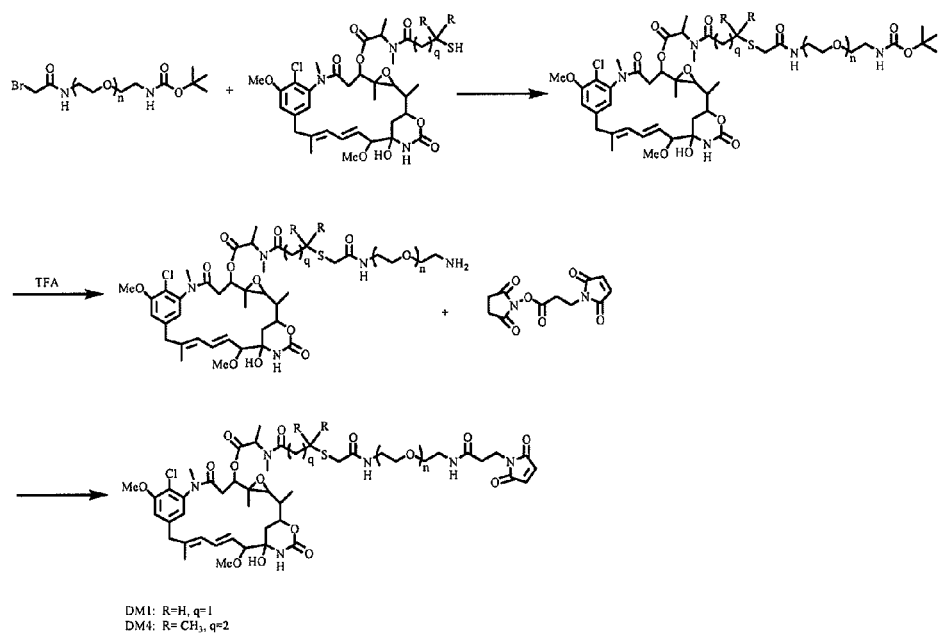
FIG. 16 shows synthetic schemes for PEG-containing, sulfhydryl-reactive, thioacetamidyl-linked compounds of the present invention (n=1-2000); 16A) Synthesis of the PEG-containing, sulfhydryl-reactive, thioacetamide linked compound for 1-step conjugation; and 16B) Synthesis of the heterobifunctional PEG-containing, sulfhydryl-reactive crosslinking compound for 2-step conjugation.
Figure 16B:
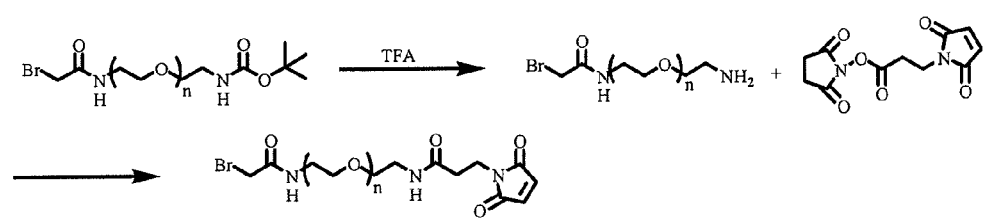
Figure 17:
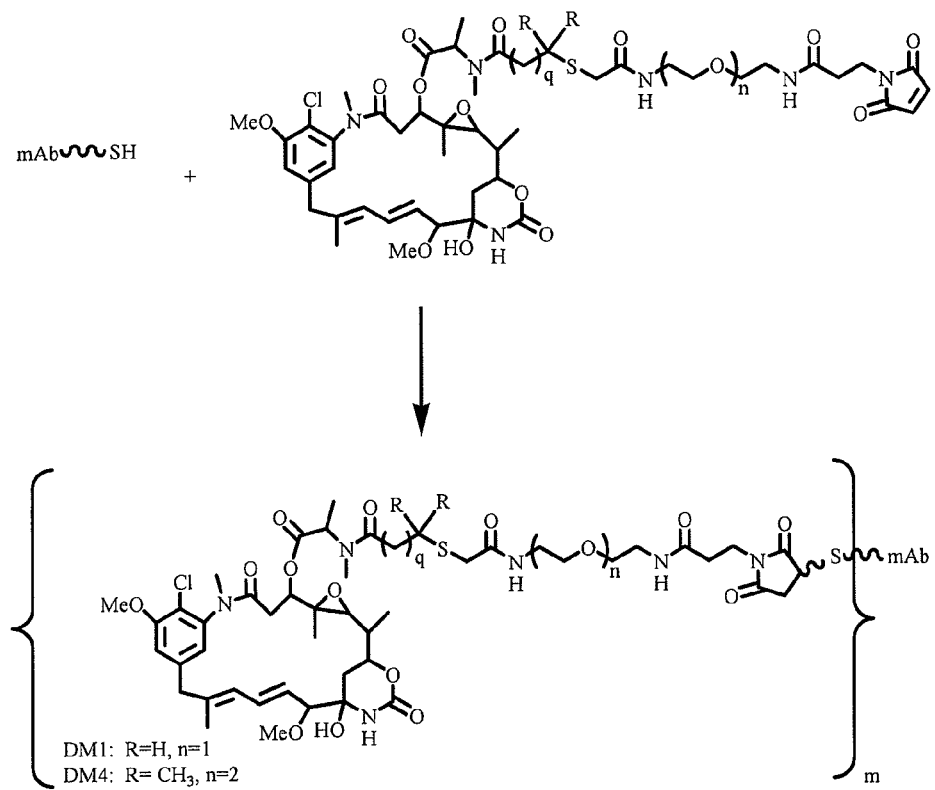
FIG. 17 shows a conjugation procedure for PEG-containing thioacetamidyl-linked conjugates of the present invention (1-step conjugation; n=1-2000; m=2-15)).
Figure 18:
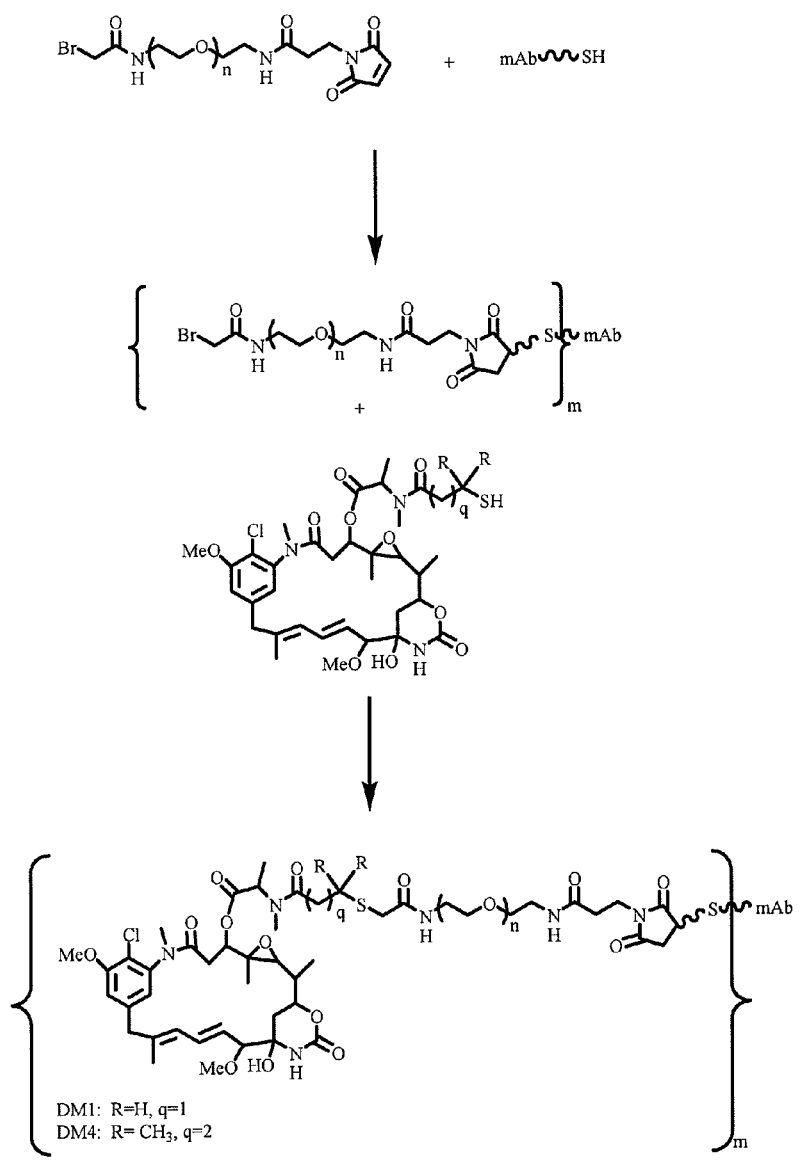
FIG. 18 shows a conjugation procedure for PEG-containing thioacetamidyl-linked conjugates of the present invention (2-step conjugation; n=1-2000; m=2-15).
Figure 19A:
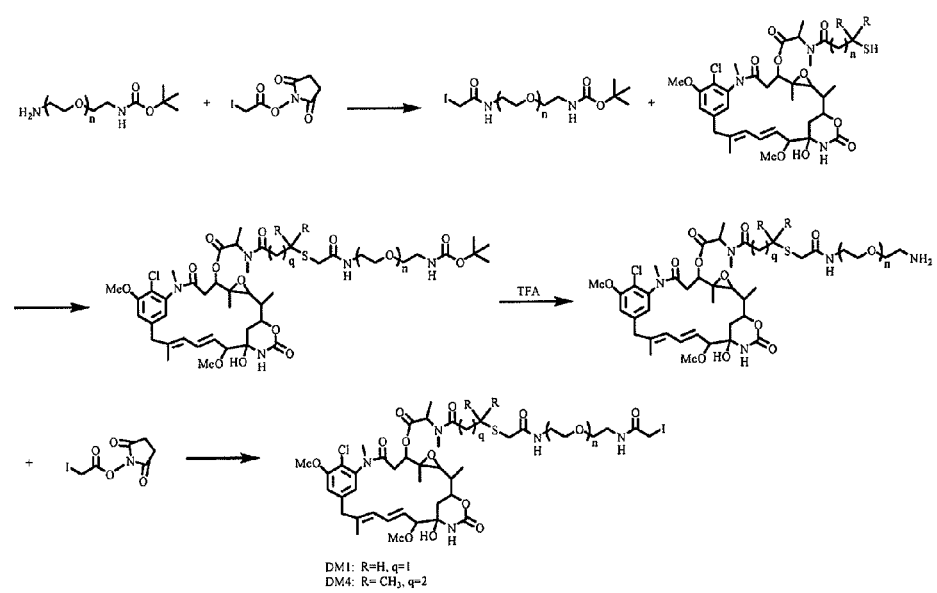
FIG. 19 shows a synthetic scheme for the PEG-containing, sulfhydryl-reactive, thioether-linked compounds of the present invention (n=1-2000): 19A) Synthesis of the PEG-containing, sulfhydryl-reactive, thioacetamidyl-linked compound for 1-step conjugation; and 19B) Synthesis of the homobifunctional PEG-containing, sulfhydryl-reactive crosslinking compound for 2-step conjugation.
Figure 19B:
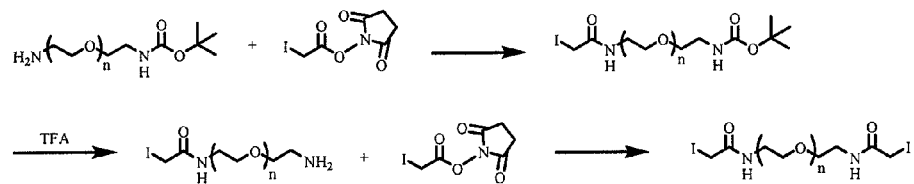
Figure 20:
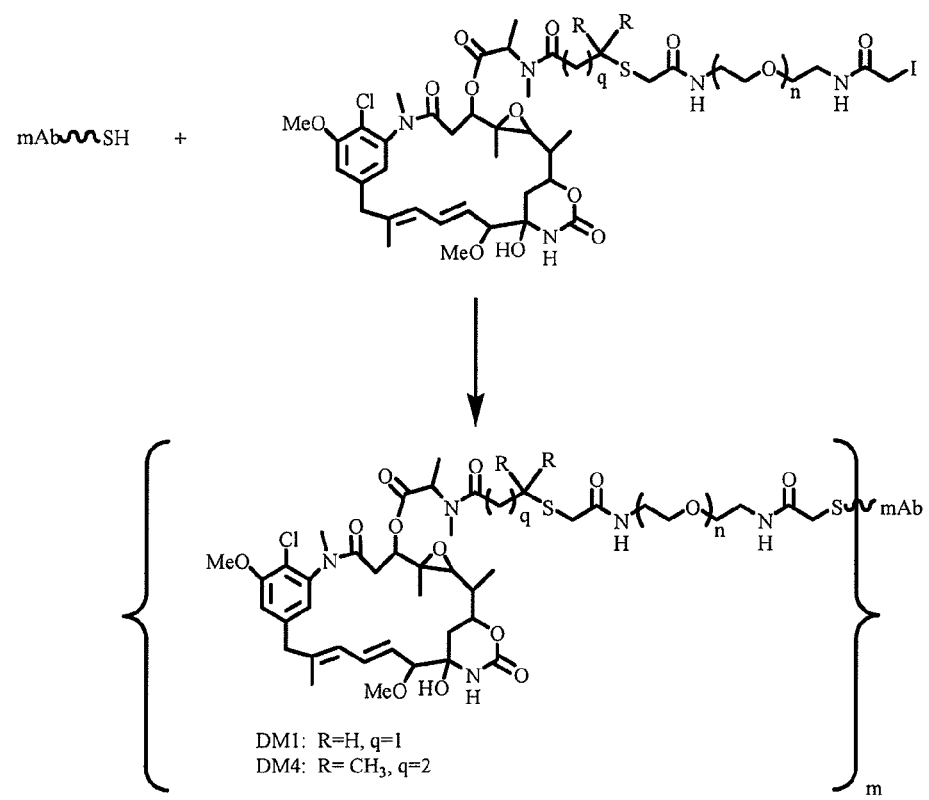
FIG. 20 shows a conjugation procedure for PEG-containing thioacetamidyl-linked conjugate of the present invention (1-step conjugation; n=1-2000; m=2-15).
Figure 21:
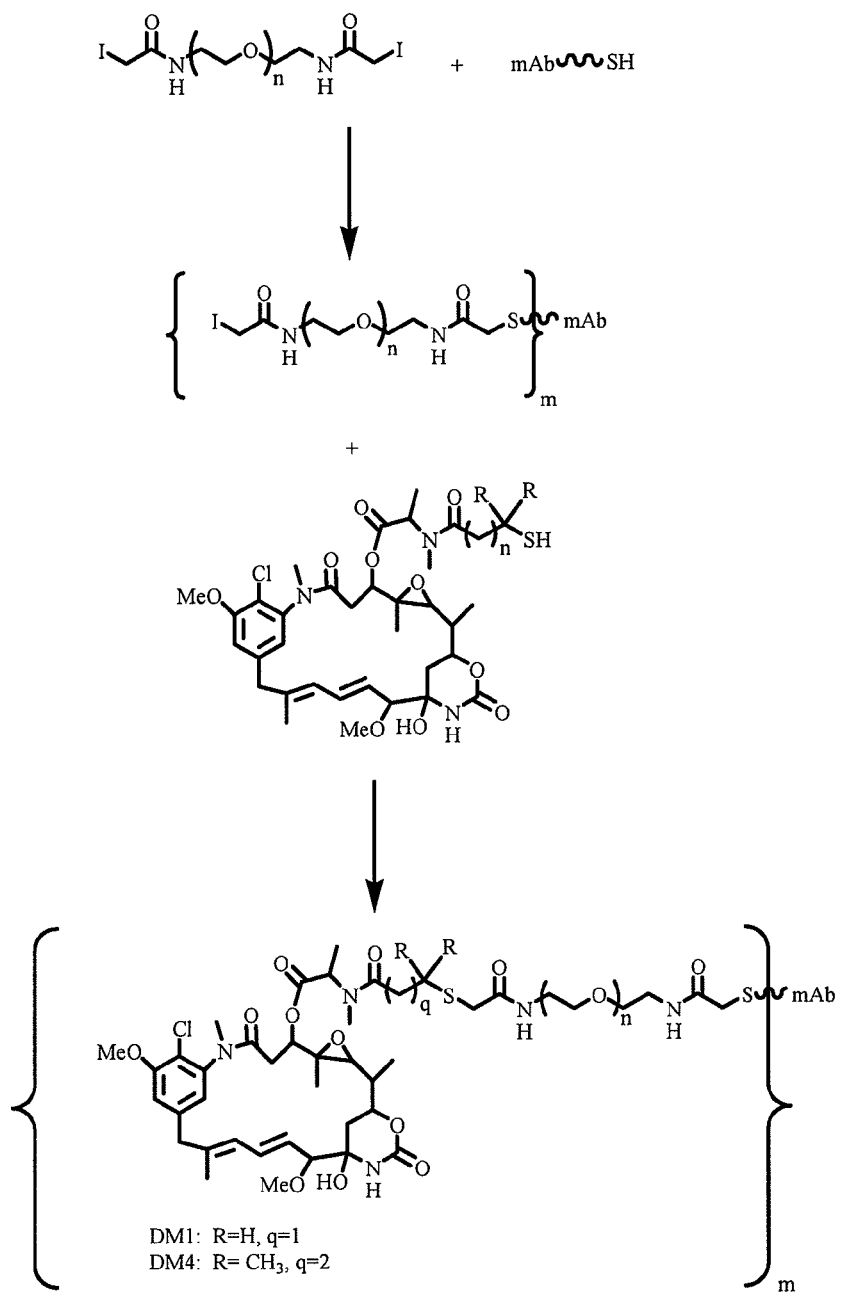
FIG. 21 shows a conjugation procedure for PEG-containing thioacetamidyl-linked conjugate of the present invention (2-step conjugation; n=1-2000; m=2-15).

FIGS. 16 and 17 shows by means of exemplification the synthesis of a PEG cross linking agent and its reaction with maytansinoid through a thioacetamido link. A maleimido substituent is then incorporated into the PEG to enable reaction with a cell binding agent via a thioether bond. Alternatively, as shown for example in FIG. 18, the cell binding agent is first linked to the PEG crosslinker through a thioether bond. The modified cell binding agent is then reacted with a maytansinoid drug to give a conjugate. The synthesis of a homobifunctional PEG crosslinker, wherein both ends of the PEG spacer contain an iodoacetamido moiety that enable linkage of both the cytotoxic drug and the cell binding agent via thioether bonds to give a conjugate containing a hydrophilic PEG spacer is shown for example in FIG. 19. The conjugation procedure to provide conjugates of the present invention is shown for example in FIGS. 20 and 21.

Figure 5:
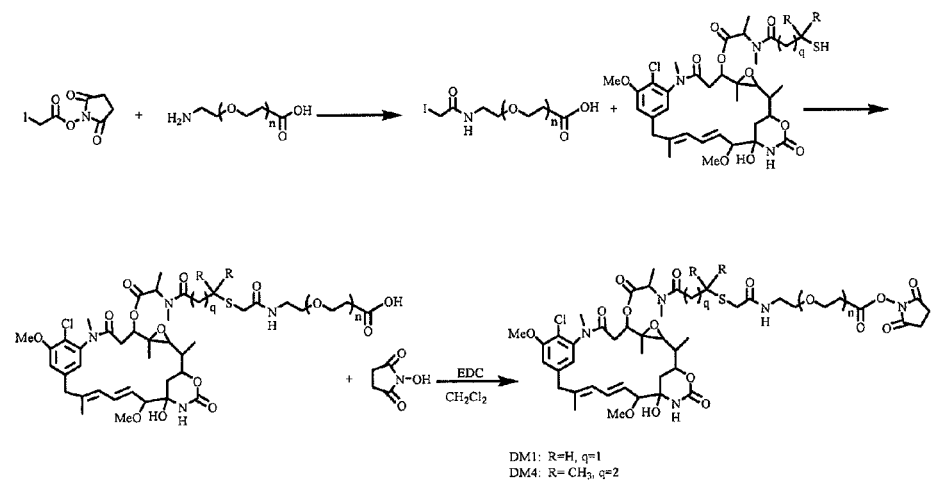
FIG. 5 shows a synthetic scheme for PEG-containing conjugates (non-cleavable thioacetamidyl-linked) of the present invention (n=1-2000).

One skilled in the art will realize that other PEG-containing crosslinkers bearing various reactive groups can be readily synthesized by methods described herein. For example, a drug bearing a hydroxyl group, such as 19-demethylmaytansinoids (U.S. Pat. No. 4,361,650) can be reacted with the iodo-acetyl-PEG linker (FIG. 5) in the presence of a base, such as potassium carbonate, to link the maytansinoid via an ether bond. Similarly, an amine-containing maytansinoid (synthesized as described in U.S. Pat. No. 7,301,019) can be reacted with an iodoacetyl PEG (shown in FIG. 5), in the presence of a base, such as pyridine or triethylamine, to provide a maytansinoid linked to the PEG via a amine link. For linkage of a drug to the PEG via an amide bond, the carboxy-PEG (shown in FIG. 5) can be reacted with an amine-containing maytansinoid in the presence of a condensing agent, such as dicyclcohexylcarbodiimide, to provide an amide bonded PEG-maytansinoid. In order to link the drug to the PEG spacer via a carbamate link, the PEG is first reacted with diphosgene to provide a PEG chloroformate, which can then be reacted with an amine-containing maytansinoid, in the presence of a base such as triethylamine, to give a carbamate linked PEG-maytansinoid.

Examples of suitable linkers include linkers having an N-succinimidyl ester or N-sulfosuccinimidyl ester moiety for reaction with the cell-binding agent, as well as a maleimido- or haloacetyl-based moiety for reaction with the drug. A PEG spacer can be incorporated into any crosslinker known in the art by the methods described herein. Crosslinking reagents comprising a maleimido-based moiety that can be incorporated with a PEG spacer include, but is not limited to, N-succinimidyl-4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Other crosslinking reagents lacking a sulfur atom can also be used in the inventive method. Such linkers can be derived from dicarboxylic acid based moieties. Suitable dicarboxylic acid based moieties include, but are not limited to, α,ω-dicarboxylic acids of the general formula shown below:

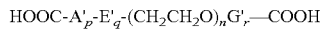

HOOC-A'$_p$-E'$_q$-(CH$_2$CH$_2$O)$_n$G'$_r$—COOH wherein A' is an optional linear or branched alkyl, alkenyl, or alkynyl group having 2 to 20 carbon atoms, E' is an optional cycloalkyl or cycloalkenyl group having 3 to 10 carbon atoms, G' is an optional substituted or unsubstituted aromatic group bearing 6 to 10 carbon atoms, or a substituted or unsubstituted heterocyclic group wherein the hetero atom is selected from N, O or S, and wherein p, q and r are each 0 or 1, provided that p, q, and r are all not zero at the same time, n is an integer from 1 to 2000.

Many of the linkers disclosed herein are described in detail in U.S. Patent Publication No. 20050169933.

In another aspect of the invention, the cell-binding agent is modified by reacting a bifunctional crosslinking reagent with the cell-binding agent, thereby resulting in the covalent attachment of a linker molecule to the cell-binding agent. As used herein, a "bifunctional crosslinking reagent" is any chemical moiety that covalently links a cell-binding agent to a drug, such as the drugs described herein. In a preferred aspect of the invention, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

In another aspect of the invention, the drug is linked to a cell-binding agent through a disulfide bond. The linker molecule comprises a reactive chemical group that can react with the cell-binding agent. Preferred reactive chemical groups for reaction with the cell-binding agent are N-succinimidyl esters and N-sulfosuccinimidyl esters. Additionally the linker molecule comprises a reactive chemical group, preferably a dithiopyridyl group that can react with the drug to form a disulfide bond. Particularly preferred linker molecules include, for example, N-succinimidyl 3-(2-pyridyldithio) propionate (SPDP) (see, e.g., Carlsson et al., *Biochem. J,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), and other reactive cross-linkers, such as those described in U.S. Pat. No. 6,913,748, which is incorporated herein in its entirety by reference.

Alternatively, as disclosed in U.S. Pat. No. 6,441,163 B1, the drug can be first modified to introduce a reactive ester suitable to react with a cell-binding agent. Reaction of these drugs containing an activated linker moiety with a cell-binding agent provides another method of producing a cell-binding agent drug conjugate. For linkage of siRNA's, siRNAs can be linked to the crosslinkers of the present invention by methods commonly used for the modification of oligonucleotides (see, for example, US Patent Publications 20050107325 and 20070213292). Thus the siRNA in its 3' or 5'-phosphoromidite form is reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine.

B. Cell-Binding Agents

The cell-binding agents used in this invention are proteins (e.g., immunoglobulin and non-immunoglobulin proteins) that bind specifically to target antigens on cancer cells. These cell-binding agents include the following:

antibodies including:
  resurfaced antibodies (U.S. Pat. No. 5,639,641);
  humanized or fully human antibodies (Humanized or fully human antibodies are selected from, but not limited to, huMy9-6, huB4, huC242, huN901, DS6, CD38, IGF-IR, CNTO 95, B-B4, trastuzumab, bivatuzumab, sibrotuzumab, pertuzumab and rituximab (see, e.g., U.S. Pat. Nos. 5,639,641, 5,665,357, and 7,342,110; U.S. Provisional Patent Application No. 60/424,332, International Patent Application WO 02/16,401, U.S. Patent Publication Number 20060045877, U.S. Patent Publication Number 20060127407, U.S. Patent Publication No. 20050118183, Pedersen et al., (1994) *J. Mol. Biol.* 235, 959-973, Roguska et al., (1994) *Proceedings of the National Academy of Sciences*, Vol 91, 969-973, Colomer et al., *Cancer Invest.,* 19: 49-56 (2001), Heider et al., *Eur. J. Cancer,* 31A: 2385-2391 (1995), Welt et al., *J. Clin. Oncol.,* 12: 1193-1203 (1994), and Maloney et al., *Blood,* 90: 2188-2195 (1997).); and epitope binding fragments of antibodies such as sFv, Fab, Fab', and F(ab')$_2$ (Parham, *J. Immunol.* 131: 2895-2902 (1983); Spring et al, *J. Immunol.* 113:470-478 (1974); Nisonoff et al, *Arch. Biochem. Biophys.* 89:230-244 (1960)).

Additional cell-binding agents include other cell-binding proteins and polypeptides exemplified by, but not limited to:

Ankyrin repeat proteins (DARPins; Zahnd et al., *J. Biol. Chem.,* 281, 46, 35167-35175, (2006); Binz, H. K., Amstutz, P. & Pluckthun, A. (2005) *Nature Biotechnology,* 23, 1257-1268) or ankyrin-like repeats proteins or synthetic peptides described, for example, in U.S. Patent Publication No. 20070238667; U.S. Pat. No. 7,101,675; WO/2007/147213; and WO/2007/062466);

interferons (e.g. α, β, γ);

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens; and growth factors and colony-stimulating factors such as EGF, TGF-α, IGF-1, G-CSF, M-CSF and GM-CSF (Burgess, *Immunology Today* 5:155-158 (1984)).

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-13; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD23, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CD152; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; and fragments of any of the above-listed polypeptides, antibody mimics Adnectins (US appl 20070082365), or an antibody which binds to one or more tumor-associated antigens or cell-surface receptors disclosed in US Publication No. 20080171040 or US Publication No. 20080305044 and are incorporated in their entirety by reference.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

Preferred antigens for antibodies encompassed by the present invention include CD proteins such as CD2, CD3, CD4, CD5, CD6, CD8, CD11, CD14, CD18, CD19, CD20, CD 21, CD22, CD 25, CD26, CD27, CD28, CD30, CD33, CD36, CD37, CD38, CD40, CD44, CD52, CD55, CD56, CD70, CD79, CD80, CD81, CD103, CD105, CD134, CD137, CD138, and CD152; members of the ErbB receptor family such as the EGF receptor, HER2, HER3 or HER4 receptor; cell adhesion molecules such as LFA-1, Macl, p150.95, VLA-4, ICAM-1, VCAM, EpCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc. The most preferred targets herein are IGF-IR, CanAg, EphA2, MUC1, MUC16, VEGF, TF, CD19, CD20, CD22, CD27, CD33, CD37, CD38, CD40, CD44, CD56, CD138, CA6, Her2/neu, EpCAM, CRIPTO (a protein produced at elevated levels in a majority of human breast cancer cells), darpins, alpha$_v$/beta$_3$ integrin, alpha$_v$/beta$_5$ integrin, alpha$_v$/beta$_6$ integrin, TGF-β, CD11a, CD18, Apo2 and C242 or an antibody which binds to one or more tumor-associated antigens or cell-surface receptors disclosed in US Publication No. 20080171040 or US Publication No. 20080305044 and are incorporated in their entirety by reference.

Preferred antigens for antibodies encompassed by the present invention also include CD proteins such as CD3, CD4, CD8, CD19, CD20, CD27, CD34, CD37, CD38, CD46, CD56, CD70 and CD138; members of the ErbB receptor family such as the EGF receptor, HER2, HER3 or HER4 receptor; cell adhesion molecules such as LFA-1, Mac1, p150.95, VLA-4, ICAM-1, VCAM, EpCAM, alpha4/beta7 integrin, and alpha v/beta3 integrin including either alpha or beta subunits thereof (e.g. anti-CD11a, anti-CD 18 or anti-CD11b antibodies); growth factors such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C, etc. The most preferred targets herein are IGF-IR, CanAg, EGF-R, EGF-RvIII, EphA2, MUC1, MUC16, VEGF, TF, CD19, CD20, CD22, CD27, CD33, CD37, CD38, CD40, CD44, CD56, CD70, CD138, CA6, Her2/neu, CRIPTO (a protein produced at elevated levels in a majority of human breast cancer cells), alpha$_v$/beta$_3$ integrin, alpha$_v$/beta$_5$ integrin, TGF-β, CD11a, CD18, Apo2, EpCAM and C242.

Monoclonal antibody techniques allow for the production of specific cell-binding agents in the form of monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793; McCafferty et al, WO 92/01047; Liming et al, WO 99/06587.)

Selection of the appropriate cell-binding agent is a matter of choice that depends upon the particular cell population that is to be targeted, but in general monoclonal antibodies and epitope binding fragments thereof are preferred, if an appropriate one is available.

For example, the monoclonal antibody My9 is a murine IgG$_{2a}$ antibody that is specific for the CD33 antigen found on Acute Myeloid Leukemia (AML) cells (Roy et al. *Blood* 77:2404-2412 (1991)) and can be used to treat AML patients. Similarly, the monoclonal antibody anti-B4 is a murine IgG$_1$ that binds to the CD19 antigen on B cells (Nadler et al, *J. Immunol.* 131:244-250 (1983)) and can be used if the target cells are B cells or diseased cells that express this antigen such as in non-Hodgkin's lymphoma or chronic lymphoblastic leukemia. The antibody N901 is a murine monoclonal IgG$_1$ antibody that binds to CD56 found on small cell lung carcinoma cells and on cells of other tumors of neuroendocrine origin (Roy et al. *J. Nat. Cancer Inst.* 88:1136-1145 (1996)); huC242 is an antibody that binds to the CanAg antigen; Trastuzumab is an antibody that binds to HER2/neu; and anti-EGF receptor antibody binds to EGF receptor.

C. Drugs

The drugs used in this invention are cytotoxic drugs capable of being linked to a cell-binding agent. Examples of suitable drugs include maytansinoids, DNA-binding drugs such as CC-1065 and its analogs, calicheamicins, doxorubicin and its analogs, vinca alkaloids, cryptophycins, dolastatin, auristatin and analogs thereof, tubulysin, epothilones, taxoids and siRNA.

Preferred maytansinoids are those described in U.S. Pat. Nos. 5,208,020; 5,416,064; 6,333.410; 6,441,163; 6,716,821; RE39,151 and 7,276,497. Preferred CC-1065 analogs are those described in U.S. Pat. Nos. 5,475,092; 5,595,499; 5,846,545; 6,534,660; 6,586,618; 6,756,397 and 7,049,316. Preferred doxorubicins and it analogs are those described in U.S. Pat. No. 6,630,579. Preferred taxoids are those described in U.S. Pat. Nos. 6,340,701; 6,372,738; 6,436,931; 6,596,757; 6,706,708; 7,008,942; 7,217,819 and 7,276,499. Calicheamaicins are described in U.S. Pat. Nos. 5,714,586 and 5,739,116.

Vinca alkaloid compounds, dolastatin compounds, and cryptophycin compounds are describe in detail in WO01/24763. Auristatin include auristatin E, auristatin EB (AEB), auristatin EFP (AEFP), monomethyl auristatin E (MMAE) and are described in U.S. Pat. No. 5,635,483, *Int. J. Oncol.* 15:367-72 (1999); Molecular Cancer Therapeutics, vol. 3, No. 8, pp. 921-932 (2004); U.S. application Ser. No. 11/134,826. U.S. Patent Publication Nos. 20060074008, 2006022925. Tubulysin compounds are described in U.S. Patent Publication Nos. 20050249740. Cryptophycin compounds are described in U.S. Pat. Nos. 6,680,311 and 6,747,021. Epothilones are described in U.S. Pat. Nos. 6,956,036 and 6,989,450.

siRNA is described in detail in U.S. Patent Publication Numbers: 20070275465, 20070213292, 20070185050, 20070161595, 20070054279, 20060287260, 20060035254, 20060008822, 20050288244, 20050176667.

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

The cell-binding agent can be conjugated to the cytotoxic drugs by methods previously described (U.S. Pat. Nos. 6,013,748; 6,441,1631, and 6,716,821; U.S. Patent Publication No. 20050169933; and WO2006/034488 A2).

D. Therapeutic Use

The cell-binding agent drug conjugates (e.g., immunoconjugates) of this invention can also be used in combination with chemotherapeutic agents. Such chemotherapeutic agents are described in U.S. Pat. No. 7,303,749.

The cell-binding agent drug conjugates (e.g., immunoconjugates) of the present invention can be administered in vitro, in vivo and/or ex vivo to treat patients and/or to modulate the growth of selected cell populations including, for example, cancer of the lung, blood, plasma, breast, colon, prostate, kidney, pancreas, brain, bones, ovary, testes, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like. Preferably, the immunoconjugates and chemotherapeutic agents of the invention are administered in vitro, in vivo and/or ex vivo to treat cancer in a patient and/or to modulate the growth of cancer cells, including, for example, cancer of the blood, plasma, lung, breast, colon, prostate, kidney, pancreas, brain, bones, ovary, testes, and lymphatic organs; more preferably lung, colon prostrate, plasma, blood or colon cancer. In a most preferred aspect, the cancer is multiple myeloma.

"Modulating the growth of selected cell populations" includes inhibiting the proliferation of selected cell populations (e.g., multiple myeloma cell populations, such as MOLP-8 cells, OPM2 cells, H929 cells, and the like) from dividing to produce more cells; reducing the rate of increase in cell division as compared, for example, to untreated cells; killing selected cell populations; and/or preventing selected cell populations (such as cancer cells) from metastasizing. The growth of selected cell populations can be modulated in vitro, in vivo or ex vivo.

In the methods of the present invention, the cell-binding agent drug conjugates (e.g., immunoconjugates) can be administered in vitro, in vivo, or ex vivo. The cell-binding agent drug conjugates (e.g., immunoconjugates) can be used with suitable pharmaceutically acceptable carriers, diluents, and/or excipients, which are well known, and can be determined, by one of skill in the art as the clinical situation warrants. Examples of suitable carriers, diluents and/or excipients include: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The compounds and compositions described herein may be administered in appropriate form, preferably parenterally, more preferably intravenously. For parenteral administration, the compounds or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

The compositions can also be in the form of sterile solid compositions that can be dissolved or dispersed in sterile water or any other injectable sterile medium.

The "therapeutically effective amount" of the cell-binding agent drug conjugates (e.g., immunoconjugates) described herein refers to the dosage regimen for modulating the growth of selected cell populations and/or treating a patient's disease, and is selected in accordance with a variety of factors, including the age, weight, sex, diet and medical condition of the patient, the severity of the disease, the route of administration, and pharmacological considerations, such as the activity, efficacy, pharmacokinetic and toxicology profiles of the particular compound used. The "therapeutically effective amount" can also be determined by reference to standard medical texts, such as the Physicians Desk Reference 2004. The patient is preferably an animal, more preferably a mammal, most preferably a human. The patient can be male or female, and can be an infant, child or adult.

Examples of suitable protocols of cell-binding agent drug conjugates (e.g., immunoconjugate) administration are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period. Dosages will be about 10 pg to about 1000 mg/kg per person, i.v. (range of about 100 ng to about 100 mg/kg).

About one to about four weeks after treatment, the patient can receive a second course of treatment. Specific clinical protocols with regard to route of administration, excipients, diluents, dosages, and times can be determined by the skilled artisan as the clinical situation warrants.

The compounds and conjugates (e.g., immunoconjugates) can also be used for the manufacture of a medicament useful for treating or lessening the severity of disorders, such as, characterized by abnormal growth of cells (e.g., cancer).

The present invention also provides pharmaceutical kits comprising one or more containers filled with one or more of the ingredients of the pharmaceutical compounds and/or compositions of the present invention, including, one or more immunoconjugates and one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. For example, the 2006 edition of the Physician's Desk Reference discloses that Taxotere (see p. 2947) is an inhibitor of tubulin depolymerization; Doxorubicin (see p 786), Doxil (see p 3302) and oxaliplatin (see p 2908) are DNA interacting agents, Irinotecal (see p. 2602) is a Topoisomerase I inhibitor, Erbitux (see p 937) and Tarceva (see p 2470) interact with the epidermal growth factor receptor. The contents of the PDR are expressly incorporated herein in their entirety by reference. One of skill in the art can review the PDR, using one or more of the following parameters, to determine dosing regimen and dosages of the chemotherapeutic agents and conjugates that can be used in accordance with the teachings of this invention. These parameters include:

1. Comprehensive index
a) by Manufacturer
b) Products (by company's or trademarked drug name)
c) Category index (for example, "antihistamines", "DNA alkylating agents," taxanes etc.)
d) Generic/chemical index (non-trademark common drug names)
2. Color images of medications
3. Product information, consistent with FDA labeling
a) Chemical information
b) Function/action
c) Indications & Contraindications
d) Trial research, side effects, warnings The entire contents of each of the foregoing references, patent applications, and patents are expressly incorporated by reference in their entirety including, without limitation, the specification, claims, and abstract, as well as any figures, tables, or drawings thereof.

E. Synthesis of Maytansinoids Having a Thioether Moiety that Bears a Reactive Group Novel maytansinoids having a non-cleavable thioether moiety that bears a reactive group are compounds of formula (5), D'-Y'—V-Q-W—Z'. Chemical groups Z' for reaction with the cell-binding agent include but are not limited to N-succinimidyl esters, N-sulfosuccinimidyl esters, pentafluorophenyl ester, tetrafluorosulfophenyl, and nitrophenyl ester. The method of preparation of these compounds are described herein. Sulfhydryl-bearing maytansinoids are covalently linked via a non-cleavable thioether bond to a heterobifuntional crosslinker that bears a reactive group and isolated prior to conjugation with a cell binding agent.

A non-cleavable linker is any chemical moiety that is capable of linking a cytotoxic drug to a cell-binding agent in a stable, covalent manner. Non-cleavable linkers are substantially resistant to acid-induced cleavage, light-induced cleavage, peptidase-induced cleavage, esterase-induced cleavage, and disulfide bond cleavage. Examples of non-cleavable linkers include linkers having an N-succinimidyl ester, or an N-sulfosuccinimidyl ester moiety and maleimido- or haloacetyl-based moiety for reaction with the maytansinoid. Crosslinking reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Maytansinoids that can be used in the present invention to produce the reactive maytansinoid derivatives bearing a thioether moiety that can be covalently linked to a cell binding agent are well known in the art and can be isolated from natural sources according to known methods or prepared synthetically according to known methods.

The synthesis of maytansinoids having a thioether moiety that bears a reactive group can be described by reference to FIGS. 1-4, where thioether-bearing maytansinoids bearing a reactive group are prepared.

Representative compounds of the invention were prepared from the thiol-containing maytansinoids: DM1, termed $N^{2'}$-deacetyl-$N^{2'}$-(3-mercapto-1-oxopropyl)-maytansine, represented by structural formula (1): and DM4, termed $N^{2'}$-deacetyl-$N^{2'}$-(4-mercapto-4-methyl-1-oxopentyl) maytansine represented by structural formula (2) are shown below:

a.)

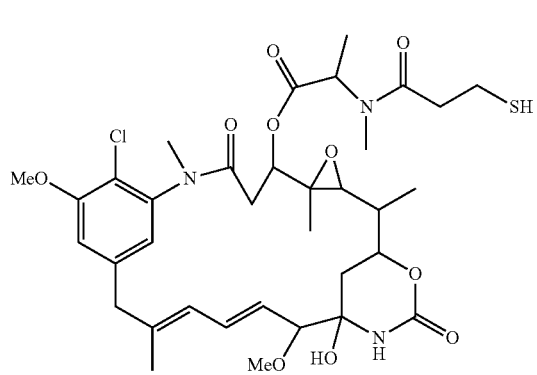

(1)

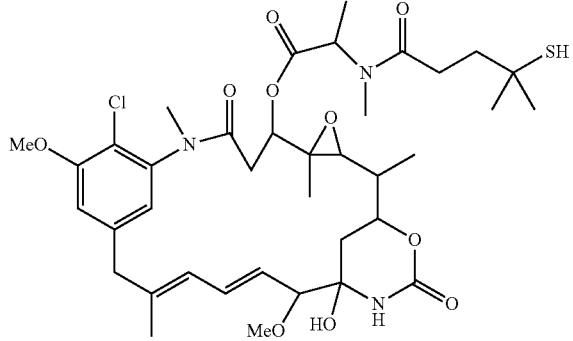

(2)

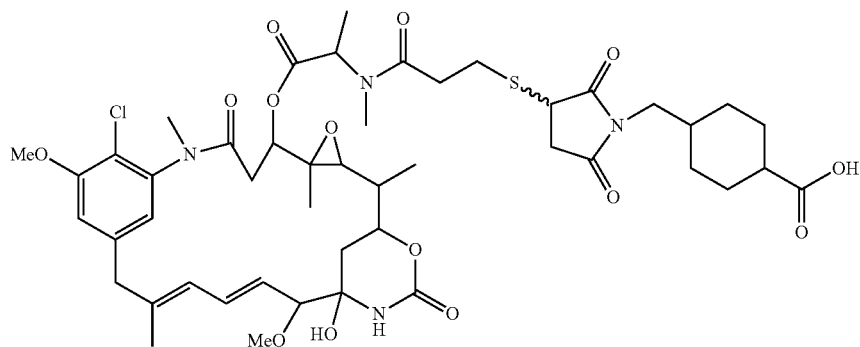

(3)

(4)
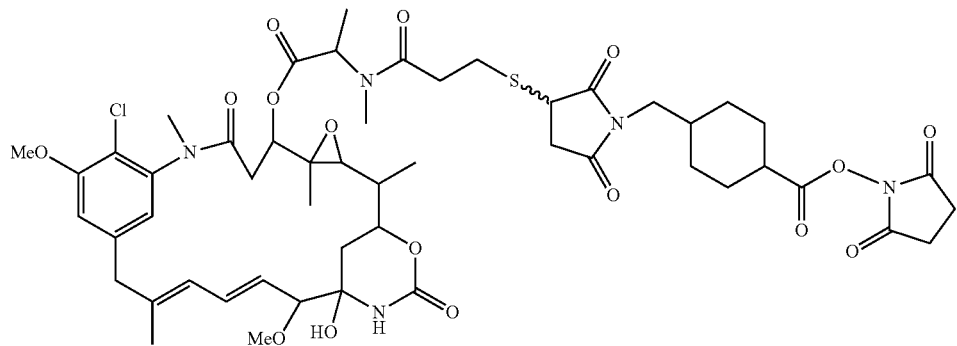
(5)
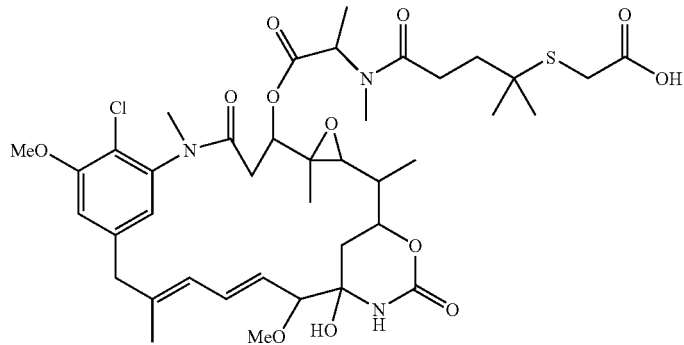
(6)
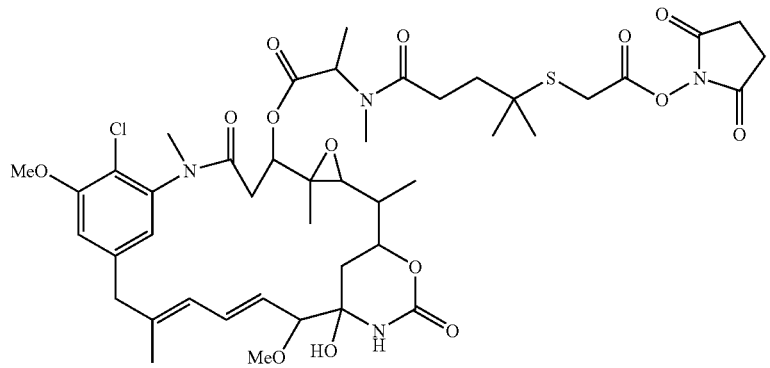
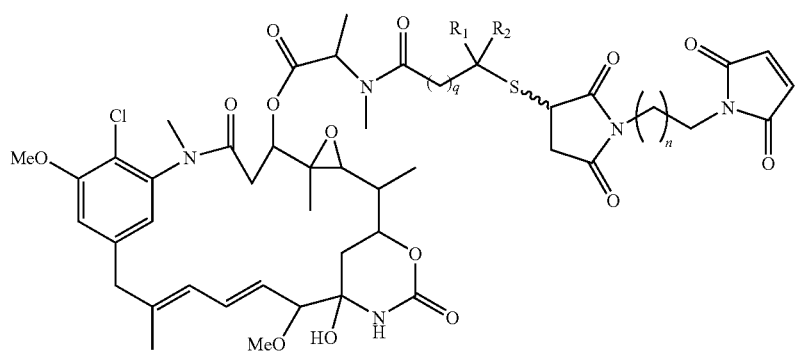
7a: q = 1, n = 5; R₁, R₂ = H
7b: q = 2, n = 5; R₁, R₂ = CH₃

Novel maytansinoids having a thioether moiety that bears a reactive group are prepared by the following newly described methods.

Synthesis of novel maytansinoids having a thiol moiety that bears a reactive group, of the formula (5): D'-Y'—V-Q-W—Z' (5)

are described comprising of the following steps:

a.) Covalently linking a heterobifunctional linker of the formula Y"—V-Q-W—Z' to a thiol bearing maytansinoid, D'; wherein Y" is a thiol-reactive group such as a maleimide or haloacetamide; V is an optional linear, branched or cyclic alkyl, alkenyl or alkynyl group preferably having from 1 to 10 carbon atoms; more preferably having 1-5 carbon atoms. W is an optional linear, branched or cyclic alkyl, alkenyl or alkynyl group preferably having from 1 to 10 carbon atoms; more preferably containing 1-5 atoms. Q represents an optional aromatic or a heterocyclic moiety; and Z' is an amine-reactive group such as but not limited to N-succinimidyl esters, N-sulfosuccinimidyl esters, pentafluorophenyl ester, tetrafluorosulfophenyl, or nitrophenyl ester. The reaction comprises of the sequence (6):

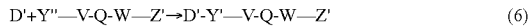

D'+Y"—V-Q-W—Z'→D'-Y'—V-Q-W—Z' (6)

b.) Stoichiometric or excess equivalents of the heterobifunctional crosslinker, Y"—V-Q-W—Z', over the thiol-bearing maytansinoid, D', such as DM1 and DM4, may be used. The reaction proceeds to completion and can be monitored by analytical methods such as HPLC and TLC. The reaction may also be performed with an excess of the thiol-bearing maytansinoid, D', over the heterobifunctional linker, Y"—V-Q-W—Z'.

c.) The reaction may be performed in a suitable organic solvent or a mixture of aqueous buffer and organic solvent such that the thiol-bearing maytansinoid, D', and the heterobifunctional linker, Y"—V-Q-W—Z', are fully soluble. Examples of suitable organic solvents include tetrahydrofuran (THF), 1,2-dimethoxyethane, N,N-dimethylformamide (DMF), N,N-dimethylacetamide (DMA), methanol and ethanol. When performing the reaction in a mixture of organic solvent and aqueous buffer the pH must be controlled to promote reaction of the sulfhydryl-bearing maytansinoid with the maleimide or haloacetamide, Y", while minimizing the potential of hydrolysis of the amine reactive group, Z. Suitable pH range for this reaction is pH 3-10 a preferred pH is 5-9 and a most preferred pH is pH 6-8.

d.) Thioether formation between the thiol-bearing maytansinoid, D', and the thiol-reactive group, Y", may also be prepared using a suitable organic base and neat organic solvent, such as those described above. Organic bases such as N,N-diisopropylethylamine (DIPEA), 1,8-Diazabicyclo[5.4.0]undec-7-ene (DBU), triethylamine and 4-methylmorpholine may be used to form the desired thioether-containing maytansinoids bearing a reactive group of the formula (5) D'-Y'—V-Q-W—Z'.

e.) A compound of the formula (5) D'-Y'—V-Q-W—Z' may be isolated following completion of the reaction. Suitable techniques for the purification of a maytansinoid having a thioether moiety that bears an amine reactive group Z' (e.g. N-succinimidyl ester) include silica gel chromatography, normal or reverse-phase preparative high performance liquid chromatography (HPLC), preparative thin layer chromatography (TLC) and crystallization.

f.) The purity and identity of the isolated product of the formula (5) D'-Y'—V-Q-W—Z' may be established by analytical methods including HPLC, mass spectroscopy (MS), LC/MS, $^1$H NMR and $^{13}$C NMR.

F. Production of Maytansinoid Derivatives Having a Thioether Moiety

Novel maytansinoid derivatives containing a thioether moiety that are useful in the preparation of maytansinoids containing a non-cleavable, thioether moiety that bears a reactive group are described herein. The preparation of these derivatives from DM1 (1) and DM4 (2) are disclosed and are represented by the formula (10):

D'-Y'—V-Q-W—COOH (10)

wherein,

V is an optional linear, branched or cyclic alkyl, alkenyl or alkynyl group preferably having from 1 to 10 carbon atoms; more preferably having 1-5 carbon atoms.

W is an optional linear, branched or cyclic alkyl, alkenyl or alkynyl group having from 1 to 10 carbon atoms; more preferably having 1-5 carbon atoms.

D' represents a sulfhydryl-bearing maytansinoid, DM1 or DM4;

Y' represents a thioether bond; and

Q represents an optional aromatic or a heterocyclic moiety.

Synthesis of novel maytansinoids derivatives having a thioether moiety that bears a carboxylic acid, of the formula (10) are described comprising of the following steps:

a.) Covalently linking a carboxylic acid linker of the formula Y"—V-Q-W—COOH to a thiol bearing maytansinoid, D'; wherein Y" is a thiol-reactive group such as a maleimide or haloacetamide; Q represents an optional an aromatic or a heterocyclic moiety. The reaction sequence is represented by the formula (11):

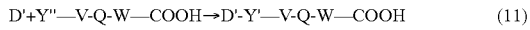

D'+Y"—V-Q-W—COOH→D'-Y'—V-Q-W—COOH (11)

Wherein:

V and W are as defined above

D' is as defined above;

Y" is as defined above;

Y' is a thioether bond between the sulfhydryl bearing maytansinoid and the carboxylic acid, COOH; and Q represents an optional aromatic or a heterocyclic moiety.

b.) Stoichiometric or excess equivalents of the carboxylic acid linker of the formula Y"—V-Q-W—COOH, over the thiol-bearing maytansinoid, D', such as DM1 and DM4, may be used. The reaction proceeds to completion and can be monitored by analytical methods such as HPLC and TLC. The reaction may also be performed with an excess of the thiol-bearing maytansinoid, D', over the carboxylic acid linker of the formula Y"—V-Q-W—COOH.

c.) The reaction may be performed in a suitable organic solvent or a mixture of aqueous buffer and organic solvent such that the thiol-bearing maytansinoid, D', and the carboxylic acid linker of the formula Y"—V-Q-W—COOH, are fully soluble. Examples of suitable organic solvents include tetrahydrofuran (THF), 1,2-dimethoxyethane, N,N-dimethylformamide (DMF), N,N-dimethylacetamide (DMA), methanol or ethanol. When performing the reaction in a mixture of organic solvent and aqueous buffer the pH must be controlled to promote reaction of the sulfhydryl with the maleimide or haloacetamide, Y". A suitable pH range for this reaction is pH 3-10 a preferred pH is 5-9 and a most preferred pH is pH 6-8.

d.) Thioether formation between the thiol-bearing maytansinoid, D', and the thiol-reactive group, Y", will also occur when using a suitable organic base and neat organic solvent, such as those described above. Organic bases such as N,N-diisopropylethylamine (DIPEA), 1,8-Diazabicyclo[5.4.0]undec-7-ene (DBU), triethylamine and 4-methylmorpholine may be used to form the desired thioether-containing maytansinoids bearing a carboxylic acid.

e.) A compound of the formula (10) D'-Y'—V-Q-W—COOH may be isolated following completion of the reaction. Suitable techniques for the purification of a maytansinoid having a thioether moiety that bears a carboxylic acid include silica gel chromatography, normal or reverse-phase preparative high performance liquid chromatography (HPLC), preparative thin layer chromatography (TLC) or crystallization.

f.) The purity and identity of the isolated product of the formula (10) D'-Y'V-Q-W—COOH may be established by analytical methods including HPLC, mass spectroscopy (MS), LC/MS, $^1$H NMR and $^{13}$C NMR.

The novel maytansinoid derivatives containing a thioether moiety bearing a terminal carboxylic acid of the formula (11) D'-Y'—V-Q-W—COOH are useful in the preparation of compounds of formula (5) D'-Y'—V-Q-W—Z'. Maytansinoid derivatives of the formula (11) D'-Y'—V-Q-W—COOH may be further derivatized to give an amine reactive group, Z. The preferred amine reactive group, Z', is an active ester such as but not limited to N-succinimidyl esters, N-sulfosuccinimidyl esters, pentafluorophenyl ester, tetrafluorosulfophenyl, or nitrophenyl ester. The process for the preparation of compounds of formula (5) from compounds of the formula (11) follows the reaction sequence:

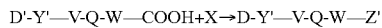

where X is N-hydroxysuccinimide to give an activated ester, Z', that is amine reactive.

A maytansinoid of the formula (5) D'-Y'—V-Q-W—Z' may be prepared from the novel maytansinoid derivative of formula (11) D'-Y'—V-Q-W—COOH by known methods described herein.

a.) Maytansinoids of formula (11) D'-Y'—V-Q-W—COOH may be reacted with a slight excess of N-hydroxysuccinimide (X) in a dry organic solvent (such as methylene chloride, dimethylformamide, tetrahydrofuran, dioxane, diethylether) in the presence of 1-(3-dimethylaminopropyl)-3-ethyl-carbodiimide hydrochloride (EDC.HCl). Condensing agents other than EDC.HCl can be employed for the reaction.

b.) Completion of reaction may be monitored using standard chemical techniques such as TLC or HPLC.

c.) Following the completion of the reaction, the maytansinoid derivative that bears a reactive N-hydroxysuccinimidyl ester may be purified by silica gel chromatography, or by HPLC, or by crystallization.

d.) The purity and identity of the isolated product of the formula (5) D'-Y'—V-Q-W—Z' may be established by analytical methods including HPLC, mass spectroscopy (MS), LC/MS, $^1$H NMR and $^{13}$C NMR.

G. Preparation of Antibody Conjugates with Maytansinoids Having a Thioether Moiety that Bears a Reactive Group A process for the preparation of a non-cleavable, thioether linked maytansinoid conjugate with a cell binding agent using an isolated, reactive maytansinoid derivative having a thioether moiety that bears a reactive group of the formula (8) CB—(Z"—W-Q-V—Y'-D')$_m$, (FIGS. 39 and 40) is described and comprises of the following steps:

a.) Covalently linking the purified amine-reactive maytansinoid bearing a thioether moiety of the formula (5) D'-Y'—W-Q-V—Z' of this invention, to a cell binding agent, CB (antibody), via covalent amide bond formation between lysine residues of the cell binding agent and the amine-reactive group linked to the maytansinoid having a thioether bond.

b.) The conjugation reaction may be performed at a concentration of 0.5-10 mg/mL antibody depending on the nature of the antibody.

b.) A stock solution of the amine-reactive non-cleavable maytansinoid bearing a thioether moiety may be prepared in neat organic solvent prior to conjugation with the antibody. Suitable organic solvents for stock solution preparation include methanol, ethanol, N,N-dimethylacetamide (DMA), N,N-dimethylformamide (DMF) and dimethyl sulfoxide (DMSO)

c.) Due to the hydrophobic nature of maytansinoids it may be necessary to carry out the conjugation to antibody in a mixture of aqueous buffer and organic solvent to ensure that the maytansinoid remains in solution during conjugation. The preferred amount of organic solvent in the aqueous buffer ranges from 0-30% (v/v) depending on the solubility of the reagent and the behavior of the antibody under these conditions. The conjugation may be carried out at pH 3-10 a preferred pH is 5-9 and a most preferred pH is pH 6-8. The buffers used for the conjugation reaction are buffers with pK$_a$ values around this pH range, such as phosphate and HEPES buffer.

c.) A 5-50 fold excess of the amine-reactive maytansinoid bearing a thioether moiety over antibody may be used in the conjugation reaction to yield a conjugate with the desired number of maytansinoid molecules linked per molecule of antibody. Preferably a range of 2-8 maytansinoids linked per antibody is desired for the final conjugate. Conditions such as antibody concentration, solubility of the reagent and pH may effect the fold excess of the maytansinoid reagent required as well as the number of maytansinoid molecules linked per mole of antibody in the final conjugate.

d.) Purification of the non-cleavable conjugate of the formula (8) CB—(Z"—V-Q-W—V-D')$_m$ by tangential flow filtration, dialysis, or chromatography (gel filtration, in-exchange chromatography, hydrophobic interaction chromatography) or a combination thereof.

EXAMPLES

Without being bound by any particular aspect, methods are described for the synthesis of polyethylene glycol (($CH_2CH_2O)_n$)-linked drugs with different reactive linkers for conjugation with cell-binding agents. These conjugation methods include a one-step conjugation of antibody with drugs such as maytansinoids linked via polyethylene glycol (($CH_2CH_2O)_n$) linker by reaction at N-hydroxysuccinimide (NHS) reactive group.

Also, described are methods of synthesizing disulfide-group containing polyethylene glycol (($CH_2CH_2O)_n$)-linked drugs with different reactive linkers for conjugation with antibody. These conjugation methods include a one-step conjugation of antibody with drugs such as maytansinoid linked with disulfide-group having polyethylene glycol (($CH_2CH_2O)_n$) linker via reaction at a N-hydroxysuccinimide (NHS) reactive group.

The following examples, which are illustrative only, are not intended to limit the present invention.

Example I

Conjugation of Antibody with Several Maytansinoid Molecules Linked Per Antibody Molecule by Disulfide Linkers Containing Traditional Aliphatic Carbon Spacers In a two-step process to conjugate an antibody with several molecules of the maytansinoid DM4 or DM1, a humanized antibody was first modified with a commercially available heterobifunctional linker (SPDB) containing both an amine-reactive N-hydroxysuccinimide group (NHS group) and a thiol-reactive 2-pyridyldithio group (—SSPy group) to incorporate several molecules of the linker in the antibody molecule (as described in W. C. Widdison et al., *J. Med. Chem.*, 2006, 49, 4392-4408). Following the incorporation of the reactive linkers in the antibody molecule, in a second reaction step the maytansinoid DM4 or DM1 with a reactive thiol group was added to the linker-modified antibody to conjugate the maytansinoid to antibody by disulfide bonds. In a specific example, a humanized antibody at a concentration of 5-10 mg/ml was modified using 10-15 fold molar excess of the commercially available heterobifunctional linker with —(CH$_2$)—$_n$ alkyl groups (such as SPDB, SPP, SPDP) in aqueous buffer at pH 6.5-8 for 0.25-3 h at ambient temperature and then purified by gel filtration (using, for example, Sephadex G25 chromatography) to obtain antibody modified with an average 8-12 linker groups per antibody molecule in high yields (typically 80-90% yields). The linked groups were estimated by measuring the release of 2-thiopyridone based on its absorbance at 343 nm ($\epsilon_{343\ nm}$=8080 M$^{-1}$ cm$^{-1}$) upon addition of excess 1,4-dithiothreitol (DTT) reagent to a small aliquot of the linker-modified antibody sample. After measuring the linked reactive groups on the antibody, the linker-modified antibody at a concentration of 2.5 mg/ml was conjugated with excess maytansinoid DM4 (1.7 fold-molar excess DM4 thiol over reactive linker) at pH 6.5. However, precipitation was observed during the antibody-maytansinoid conjugation reaction and poor yields of the antibody-maytansinoid conjugates (~38-60% yields) were obtained upon purification of the antibody-maytansinoid conjugates by gel filtration. The number of linked maytansinoids per antibody molecule was determined from absorbance measurements at 252 nm and 280 nm and using the extinction coefficients for maytansinoid and antibody at 252 nm and 280 nm. In addition to the precipitation and poor yields of the antibody-maytansinoid conjugates at ~1-1.5 mg/ml, the numbers of incorporated maytansinoid per antibody molecule were much lower (~5.2-5.5 average maytansinoid molecules per antibody molecule) than expected based on the much greater average number of initial reactive linker groups incorporated per antibody molecule (~8-12 reactive linker groups per antibody molecule) suggesting precipitation of the higher maytansinoid-bearing antibody conjugates. In another example, a humanized antibody was first modified with the SPDB heterobifunctional linker to incorporate 11 pyridyldithio groups per antibody molecule, which upon a second reaction with 1.7 fold molar excess of DM4 maytansinoid thiol showed significant precipitation in the reaction mixture resulting in a very poor recovery of <30% antibody-maytansinoid conjugate. Using commercially available heterobifunctional linkers such as SPDB or SPDP with aliphatic spacers it is typically difficult to incorporate greater than 4 or 5 maytansinoid molecules per antibody at high conjugation yields for antibody-maytansinoid conjugate concentrations of 1 mg/ml or higher concentrations. This observed precipitation and low yield of antibody-maytansinoid conjugates having SPDB- or SPDP-derived linkers was not seen upon the initial SPDB- or SPDP-linker modification of antibodies (before conjugation with maytansinoids) suggesting that the aggregation and precipitation of the antibody-maytansinoid conjugates was presumably caused by the attachment of hydrophobic molecules.

Example II

Conjugation of Antibody with Several Maytansinoid Molecules Linked Per Antibody Molecule by Disulfide Linkers Containing Hydrophilic Polyethylene Oxide Spacers (PEG$_n$, or (—CH$_2$—CH$_2$—O)$_{n=1-14}$)

To explore if hydrophilic spacers such as polyethylene oxide (PEG$_n$, or (—CH$_2$—CH$_2$—O)$_{n=1-14}$) could perhaps prevent the aggregation and precipitation of antibody-maytansinoid conjugates with a high number of maytansinoid molecules (>4 average per antibody molecule), several new heterobifunctional and monofunctional maytansinoid derivatives were prepared which could be conjugated to antibody by direct modification or a two-step reaction involving the initial derivatization of antibody at lysine residues followed by the reaction of maytansinoids (see, for examples, FIGS. 3, 6, 11, and 12).

Synthesis of 15-(2-pyridyldithio)-4,7,10,13-tetraoxapentadecanoic acid

A solution of aldrithiol-2 (1.17 g, 5.31 mmol) was prepared in 5.0 mL of 1,2-dimethoxyethane in a 10 mL round bottom flask. To the reaction flask was added a solution of 3-(2-thiotetraethyleneglycol) propionic acid (QuantaBiodesign, 490 mg, 1.73 mmol) dissolved in 1.0 mL of 1,2-dimethoxyethane. The reaction proceeded for 3.5 hours with stirring and the product was purified by silica chromatography eluting with 5% methanol in methylene chloride. The solvent was removed in vacuo to yield 432 mg (64% yield) of the desired product.

Synthesis of PySS-PEG$_4$-NHS[15-(2-pyridyldithio)-4,7,10,13-tetraoxapentadecanoic acid-N-hydroxysuccinimide ester]

A 10 mL round bottom flask was charged with 15-(2-pyridyldithio)-4,7,10,13-tetraoxapentadecanoic acid (431 mg, 1.10 mmol), 5.0 mL of methylene chloride and a stir bar. N-hydroxy succinimide (3.6 mg, 0.31 mmol) and 1-[3-(Dimethylamino)propyl]-3-ethylcarbodiimide hydrochloride (6.8 mg, 0.036 mmol) were added to the reaction vessel and the reaction proceeded for 2 hours at room temperature with stirring. The product was purified by silica chromatography eluting with 7% 1,2-dimethoxyethane in methylene chloride. The solvent was removed in vacuo to give 206 mg (38% yield) of the desired product. MS: m/z. found: 511.1 (M+Na)$^+$, calculated: 511.2.

Synthesis of 15-(DM4-dithio)-4,7,10,13-tetraoxapentadecanoic acid

Figure 6A:
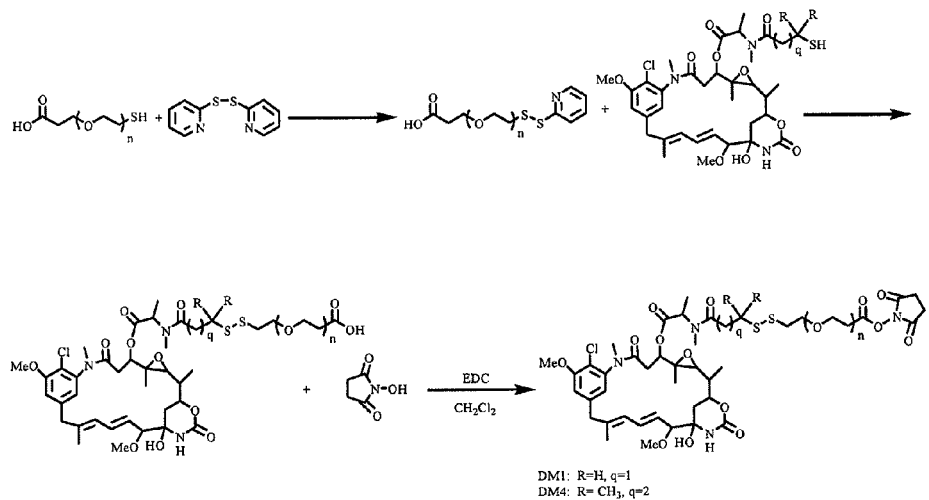
FIG. 6 shows synthetic schemes for PEG-containing disulfide linked compounds of the present invention (n=1-14) 6A) Synthesis of the PEG-containing disulfide linked compound for 1-step conjugation to cell-binding agent; and 6B) Synthesis of the heterobifunctional PEG-containing disulfide linked crosslinking compound.
Figure 6B:
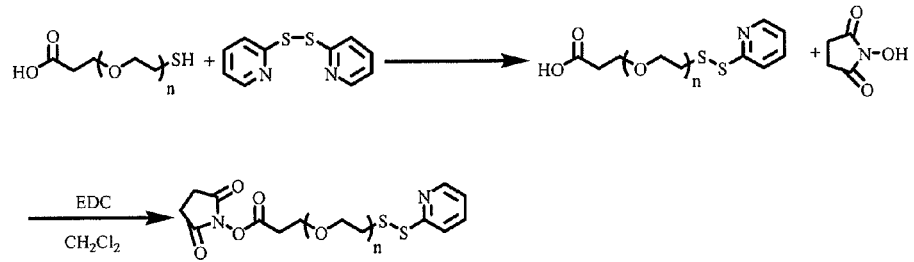

A solution of N$^{2'}$-deacetyl-N$^{2'}$-(4-mercapto-4-methyl-1-oxopentyl)maytansine (DM4, 18.6 mg, 0.0239 mmol) and 15-(2-pyridyldithio)-4,7,10,13-tetraoxapentadecanoic acid (14.0 mg, 0.0358 mmol) was prepared in 0.75 mL of 1,2-dimethoxyethane. 4-methylmorpholine (6.0 mg, 0.0597 mmol) was added to the reaction vessel and the reaction proceeded for 24 hours at room temperature with stirring. Upon reaction completion the crude reaction mixture was dried in vacuo and used without further purification (FIG. 6).

Synthesis of 15-(DM4-dithio)-4,7,10,13-tetraoxapentadecanoic acid-N-hydroxy succinimide ester (DM4-SPEG$_4$-NHS)

The crude 15-(DM4-dithio)-4,7,10,13-tetraoxapentadecanoic acid was dissolved in 2.0 mL of methylene chloride and combined with N-hydroxy succinimide (3.6 mg, 0.31 mmol) and 1-[3-(Dimethylamino)propyl]-3-ethylcarbodiimide hydrochloride (6.8 mg, 0.036 mmol). The solution was stirred for 2.5 hours and the product was purified by silica chromatography eluting with 4% methanol in methylene chloride. The solvent was removed under vacuum to give 15.0 mg (54% yield) of the desired product. MS: m/z. found: 1179.3 (M+Na)$^+$, calculated: 1179.4 (FIG. 6).

Figure 12:
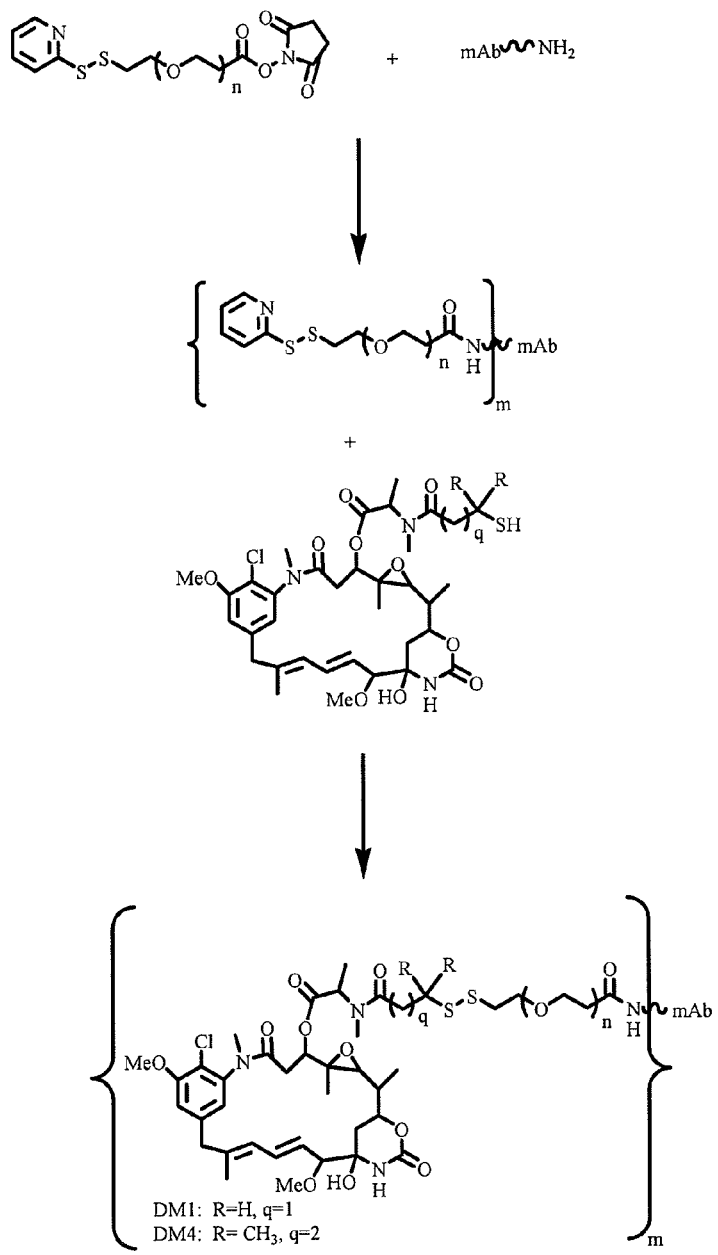
FIG. 12 shows a conjugation procedure for PEG-containing disulfide linked conjugate of the present invention (2-step conjugation; n=1-14; m=3-8).

Two-Step Conjugation of Antibody to Link a High Number of Maytansinoid Molecules Per Antibody Molecule Using Disulfide Linkers Containing Hydrophilic Polyethylene Oxide Spacers (PEG$_n$, or (—CH$_2$—CH$_2$—O)$_{n=1-14}$):

A novel observation was made when new heterobifunctional reagents with hydrophilic spacers such as polyethylene oxide (PEG$_n$, or (—CH$_2$—CH$_2$—O)$_{n=1-14}$) were used to modify antibody followed by conjugation with DM4 thiol. The conjugation mixtures of the antibody-maytansinoid conjugates with hydrophilic PEG$_n$ spacers did not show any precipitate and consistently gave a high conjugate yield (>70%) with very high monomer fraction (>90%). As an example, a humanized antibody at a concentration of 8 mg/ml was modified with the PySS-PEG$_4$-NHS reagent at several fold molar excess over antibody concentration in pH 8 buffer for 1 h at 30° C. and then purified by gel filtration. The linked dithiopyridyl groups per antibody molecule were estimated to be ~4-16 by 2-thiopyridone release assay of aliquots using excess dithiothereitol, based upon which a 1.4-fold molar excess of DM4 maytansinoid thiol was added to each dithiopyridyl-PEG$_n$-linker modified antibody solution for the conjugation step at pH 6.5, overnight at 25° C., and then the conjugate was purified by gel filtration (FIG. 12). The final incorporated maytansinoid per antibody values for the different conjugation mixtures with different initial linker incorporations ranged from 3 to 9 average maytansinoid per antibody molecule, with no observed precipitation, >70% yields and very high monomer (>90% monomer based on size-exclusion TSK-GEL G3000 HPLC using 20% isopropanol or 0.4 M sodium perchlorate). The unconjugated drug in the final conjugates was determined to be less than 0.6% by HiSep Mixed-Mode chromatography (HiSep column, Supelco) indicating that maytansinoids were covalently linked to antibody. In another example, a humanized antibody at a concentration of 8 mg/ml was modified with PySS-PEG$_4$-NHS reagent at several fold molar excess over antibody concentration in pH 6.5 buffer for 1.5 h at 25° C. and then purified by gel filtration. The dithiopyridyl-PEG$_n$-bearing linker groups on antibody samples were estimated as 6-18 per antibody molecule, which were then reacted with 1.3-1.7-fold molar excess of DM4 maytansinoid thiol at pH 6.5, 25° C. overnight, and then purified by gel filtration. No precipitation was observed and the final antibody-maytansinoid conjugate samples at ~1-2 mg/ml showed high monomer fraction (>90%), indicating lack of aggregation, and high numbers of ~3.1 to 7.1 covalently attached maytansinoid molecules per antibody with very low unconjugated maytansinoid (<1.7% unconjugated maytansinoid estimated by HiSep chromatography). The conjugates with high drug load per antibody were stable upon storage at 4° C. even up to the longest time analyzed (1.5 months).

Figure 11:
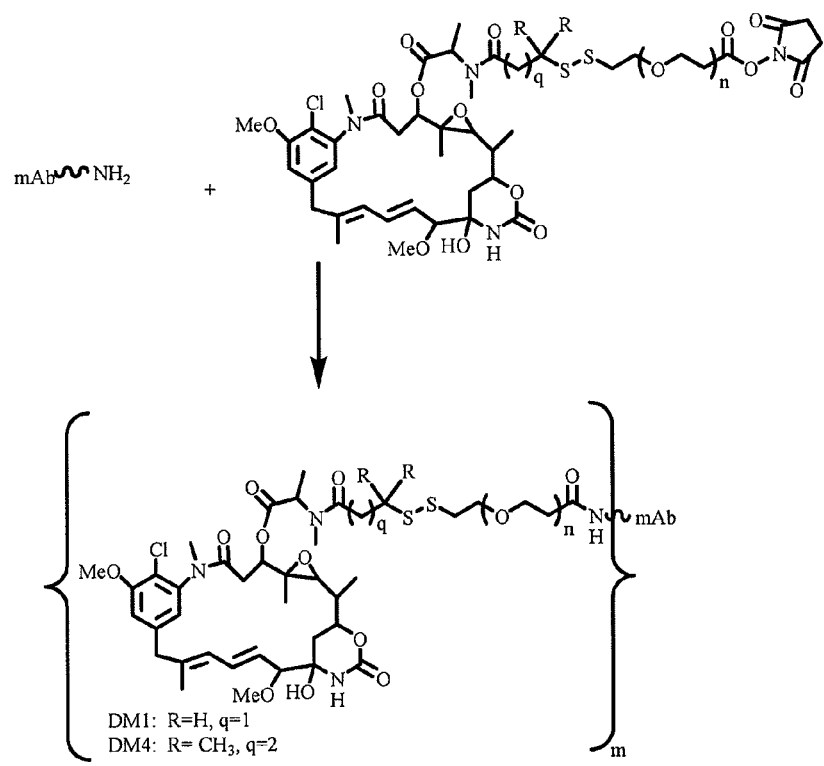
FIG. 11 shows a conjugation procedure for PEG-containing disulfide linked conjugate of the present invention (1-step conjugation; n=1-14; m=3-8).

One-Step Conjugation of Antibody to Link a High Number of Maytansinoid Molecules Per Antibody Molecule Using Disulfide Linkers Containing Hydrophilic Polyethylene Oxide Spacers (PEG$_n$, or (—CH$_2$—CH$_2$—O)$_{n=1-14}$):

In a one-step conjugation approach, antibody-maytansinoid conjugates with disulfide linkers containing hydrophilic polyethyleneoxide spacers (PEG$_n$, or (—CH$_2$—CH$_2$—O)$_{n=1-14}$) were generated by the conjugation of a humanized antibody at a concentration of 4 mg/ml with 10-20 fold molar excess of DM4-SPEG$_4$-NHS reagent in pH 8 buffer for 2 h at 30° C. followed by purification by gel filtration to obtain an antibody-maytansinoid conjugate at a concentration of 1.4 mg/ml with 6.6 conjugated maytansinoid per antibody molecule (82% monomer) (FIG. 11). Therefore, both 2-step and 1-step approaches were used to obtain high number of linked maytansinoids per antibody molecule with disulfide linkers containing hydrophilic polyethyleneoxide spacers (PEG$_n$, or (—CH$_2$—CH$_2$—O)$_{n=1-14}$).

Example III

Conjugation of Antibody with Several Maytansinoid Molecules Linked Per Antibody Molecule by Thioether Linkers Containing Hydrophilic Polyethylene Oxide Spacers (PEG$_n$, or (—CH$_2$—CH$_2$—O)$_n$)

Figure 7:
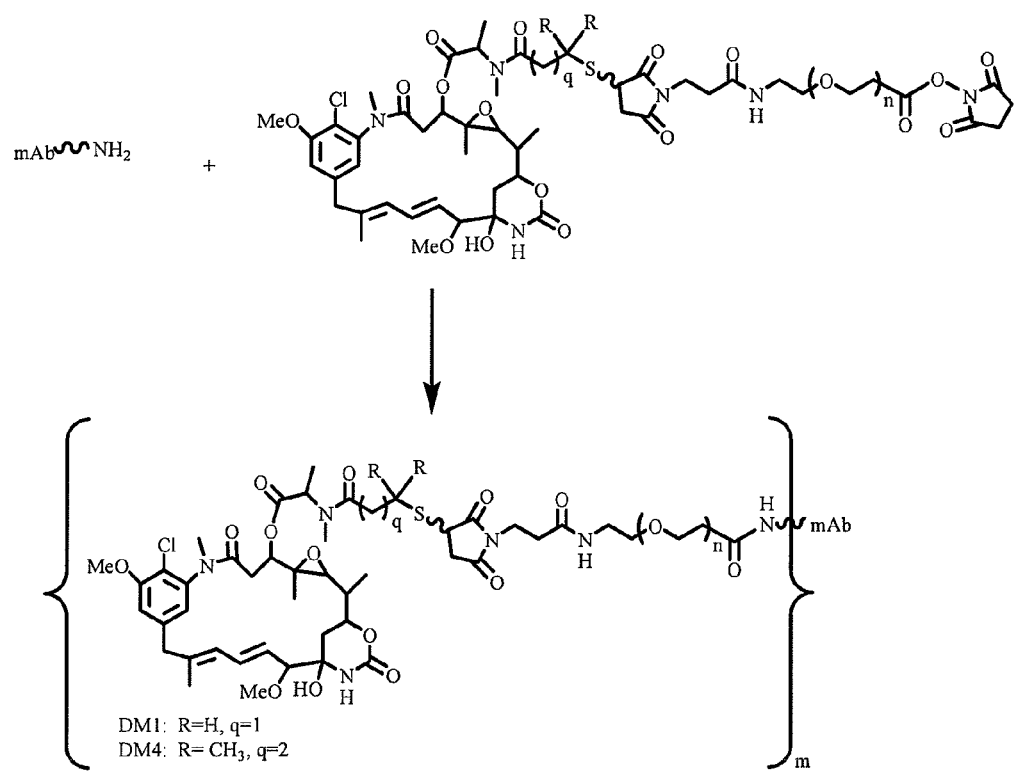
FIG. 7 shows a conjugation procedure for PEG-containing thiosuccinimidyl-linked conjugates of the present invention (one-step conjugation; n=1-2000; m=2-15).
Figure 8:
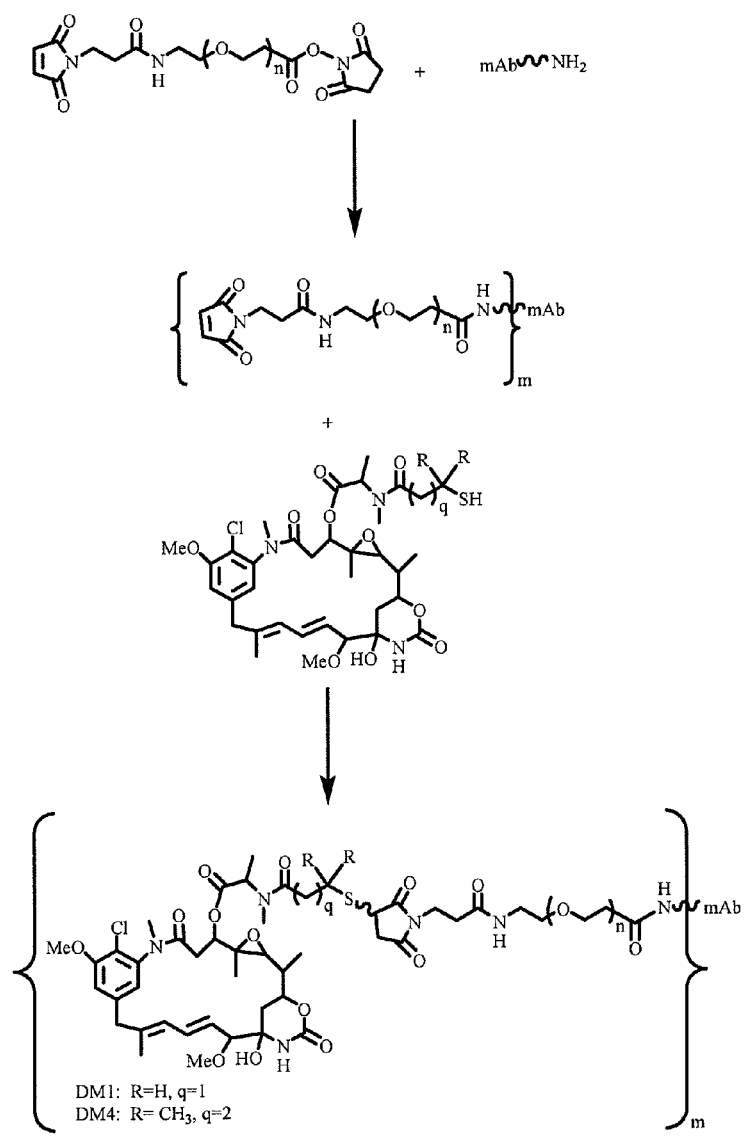
FIG. 8 shows a conjugation procedure for PEG-containing thiosuccinimidyl-linked conjugate of the present invention (2-step conjugation; n=1-2000; m=2-15).
Figure 9:
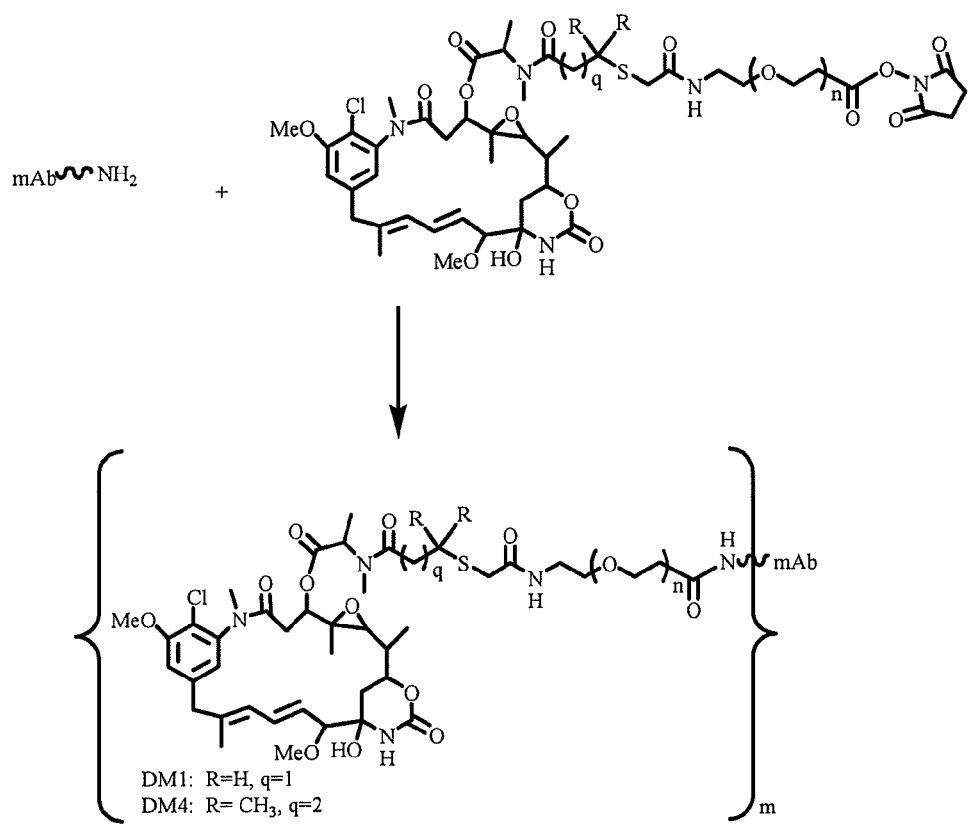
FIG. 9 shows a conjugation procedure for PEG-containing thioether-linked (thioacetamidyl-linked) conjugate of the present invention (1-step conjugation; n=1-2000; m=2-15).
Figure 10:
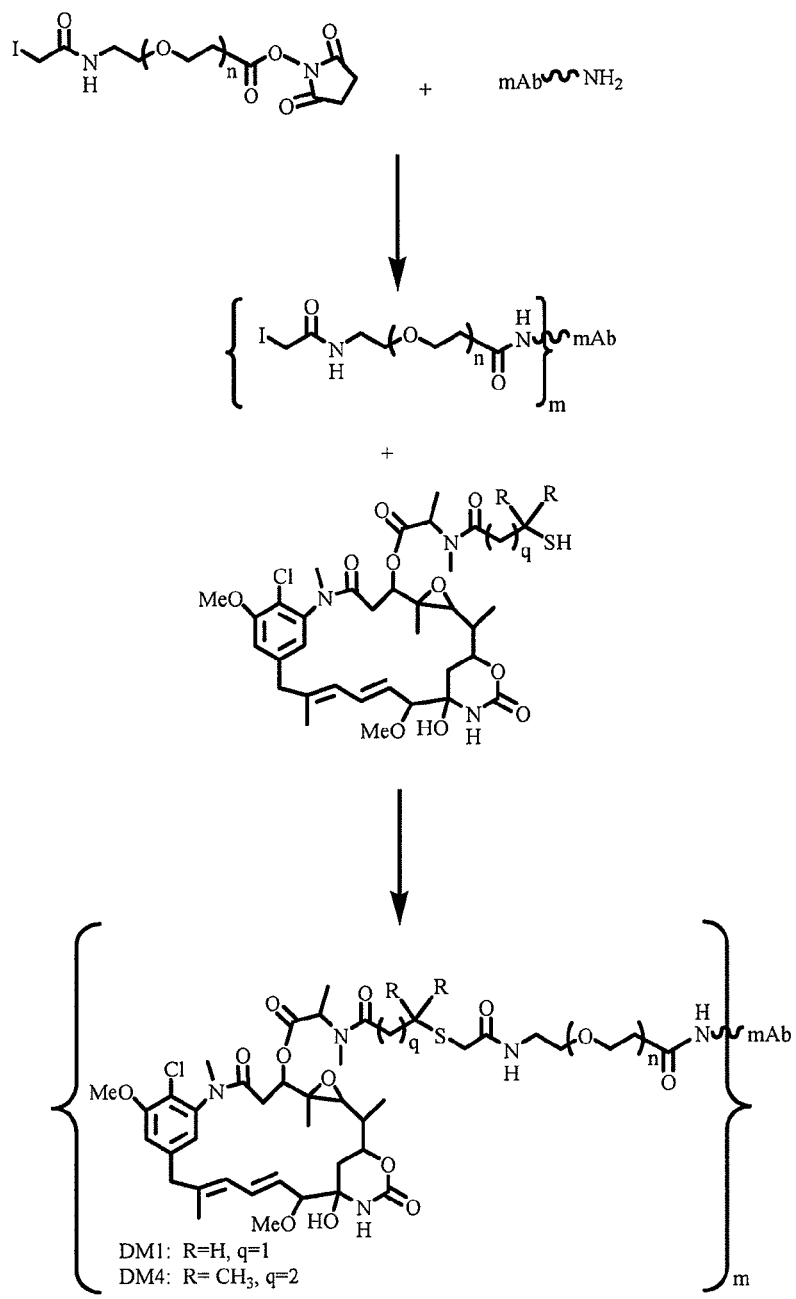
FIG. 10 shows a conjugation procedure for PEG-containing thioether-linked (thioacetamidyl-linked) conjugate of the present invention (2-step conjugation; n=1-2000; m=2-15).

To directly modify the lysine residues of antibody, N-hydroxysuccinimide esters of maytansinoids with traditional aliphatic linkers such as alkyl linkers derived from SPP (described in W. C. Widdison et al., *J. Med. Chem.*, 2006, 49, 4392-4408) were used initially to conjugate antibodies in a 1-step method. Attempts to conjugate a humanized antibody with a 8-fold molar excess of DM1-SPP-NHS reagent as a test reagent at 5 mg/ml in pH 8 buffer at 30° C. for 2 h (followed by gel filtration and dialysis) resulted in significant precipitation and aggregation, such that the final conjugate was only 61% monomer with about 3.3 linked maytansinoids per antibody. In contrast, the use of DM1-Mal-PEG$_4$-NHS reagent under similar conditions resulted in a conjugate with 5.4 linked maytansinoid molecules per antibody at 1.1 mg/ml with no precipitation in the final conjugate (FIG. 7 or 9). Similarly DM1-Mal-PEG$_2$-NHS reagent was used to obtain high numbers of conjugated maytansinoids linked per antibody molecule via thioether bonds. In another example, a murine IgG$_1$ antibody was conjugated at 4 mg/ml with 10- and 20-fold molar excess of DM1-Mal-PEG$_4$-NHS reagent in pH 8 buffer for 2 h at 30° C. followed by gel filtration to obtain antibody-maytansinoid conjugates at ~1 mg/ml concentration with 4.1 and 7.8 covalently conjugated maytansinoid molecules per antibody molecule (98% monomer) with undetectable levels of unconjugated drug (HiSep HPLC assay). In another example, a humanized antibody was conjugated with excess DM1-Mal-PEG$_4$-NHS reagent to obtain average 10.7 linked maytansinoid molecules per antibody (99% monomer; 1.1 mg/ml concentration). The PEG$_4$-linked thioether conjugates were also prepared from antibodies using a two-step conjugation procedure outlined in FIG. 8 and FIG. 10. Therefore large number of maytansinoid molecules can be introduced per antibody molecule by the use of hydrophilic linkers such as PEG$_n$ or (—CH$_2$—CH$_2$—O)$_n$ (see, for example, FIGS. 1, 2, 4, 5, 7, 8, 9, 10, 13, 14, 15, 16, 17, 18, 19, 20, and 21).

Synthesis of DM1-Mal-PEG$_2$-NHS

Figure 4:
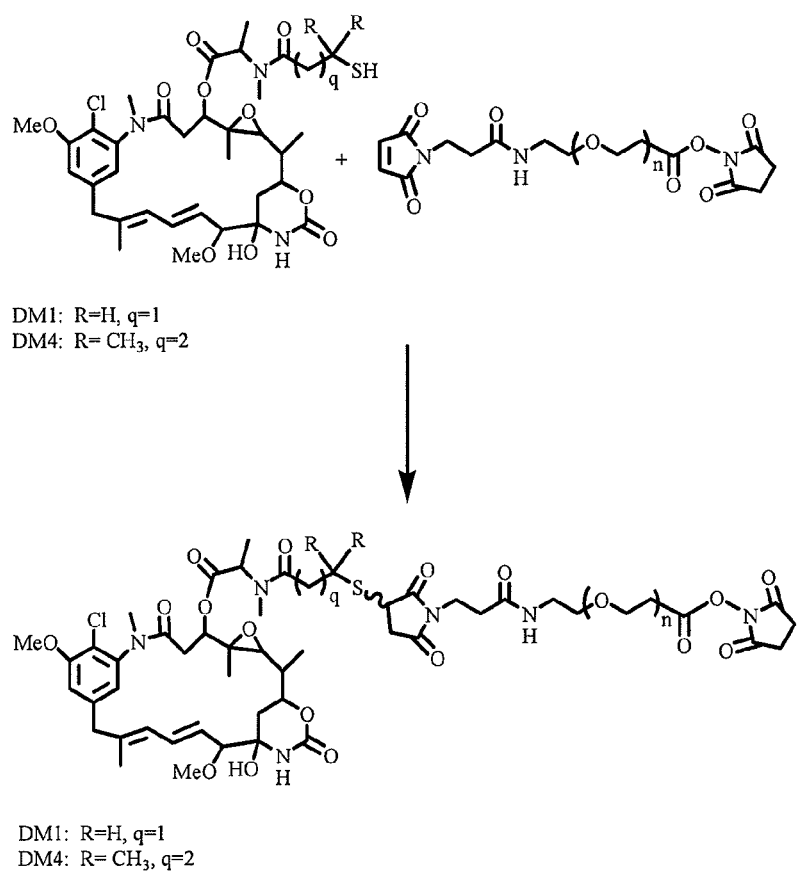
FIG. 4 shows synthetic schemes for PEG-containing conjugates (non-cleavable thiosuccinimidyl-linked) of the present invention (n=1-2000).

A solution of N$^{2'}$-Deacetyl-N$^{2'}$-(3-mercapto-1-oxopropyl)-maytansine (DM1, 13.4 mg, 0.0182 mmol) was prepared in 0.70 mL of THF and succinimidyl-[(N-maleimidopropionamido)-diethyleneglycol]ester (NHS-PEG$_2$-Maleimide, Quanta Biodesign, 11.6 mg, 0.0273 mmol) was added in 1.5 mL of 2:1 (v/v) mixture of aqueous potassium phosphate buffer (50 mM, pH 6) and THF. The reaction proceeded for 1 hour with stirring at room temperature and TLC analysis indicated that the reaction was complete. The crude reaction mixture was purified by silica chromatography eluting with 8% ethanol in methylene chloride; the solvent was removed under vacuum to give 6.0 mg (28% yield) of the desired product. MS: m/z found: 1185.3 (M+Na)$^+$, calculated: 1184.4 (FIG. 4).

Synthesis of DM1-Mal-PEG$_4$-NHS

A solution of N$^{2'}$-Deacetyl-N$^{2'}$-(3-mercapto-1-oxopropyl)-maytansine (DM1, 28.1 mg, 0.0381 mmol) was prepared in 0.50 mL of THF and succinimidyl-[(N-maleimidopropionamido)-tetraethyleneglycol]ester (NHS-PEG$_4$-Maleimide, Quanta Biodesign, 39.1 mg, 0.0762 mmol) was added in 1.5 mL of 2:1 (v/v) mixture of aqueous potassium phosphate buffer (50 mM, pH 6) and THF. The reaction proceeded for 1 hour with stirring at room temperature and TLC analysis indicated that the reaction was complete. The crude reaction mixture was purified by silica chromatography eluting with 6% ethanol in methylene chloride; the solvent was removed under vacuum to give 9.6 mg (20% yield) of the desired product. MS: m/z. found: 1273.5 (M+Na)$^+$, calculated: 1273.5 (FIG. 4).

Example IV

Mass Spectrometric Analysis of High Maytansinoid Bearing Antibody Species

Figure 22:
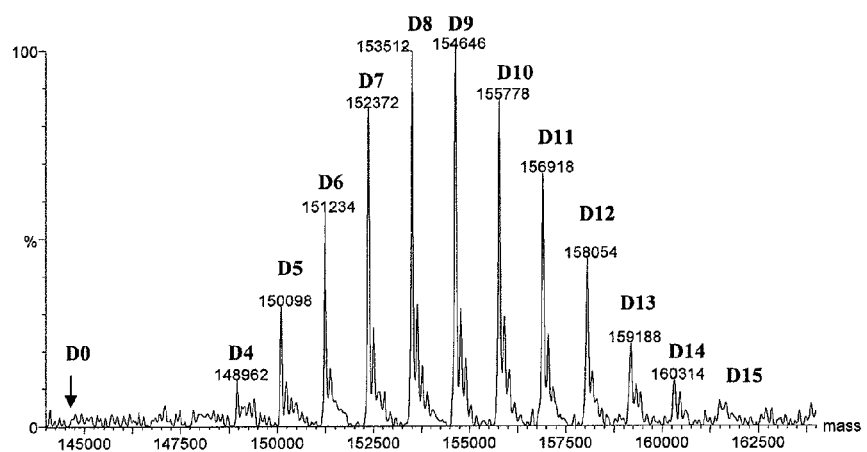
FIG. 22 shows a mass spectrum (MS) of deglycosylated HuAb-PEG$_4$Mal-DM1 conjugate (10.7 DM1/Ab, average).
Figure 23:
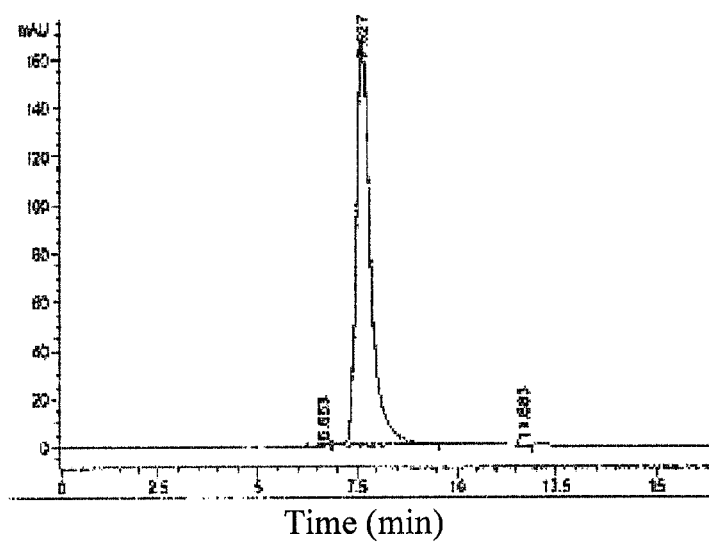
FIG. 23 shows size exclusion chromatography (SEC) of HuAb-PEG$_4$Mal-DM1 conjugate (10.7 DM1/Ab, average).

To analyze the high maytansinoid bearing antibody species with the hydrophilic PEG linkers, a very high maytansinoid bearing Ab-PEG$_4$-Mal-DM1 conjugate with average 10.7 DM1 per antibody was selected. The conjugate was deglycosylated and then analyzed by ESI-TOF MS (FIG. 22). The mass spectrum shows various species of antibody labeled with different numbers of linked maytansinoid ranging from 4-15 drugs per antibody with the maxima at around 8-9 drugs per antibody. This distribution is normal suggesting that no selective disappearance was seen for the high drug bearing species, which is consistent with the high solubility of the final conjugate. The size exclusion chromatography HPLC of the high maytansinoid bearing Ab-PEG$_4$-Mal-DM1 conjugate with average 10.7 DM1 per antibody showed a surprisingly high >99% amount of monomer (FIG. 23).

Example V

Figure 24:
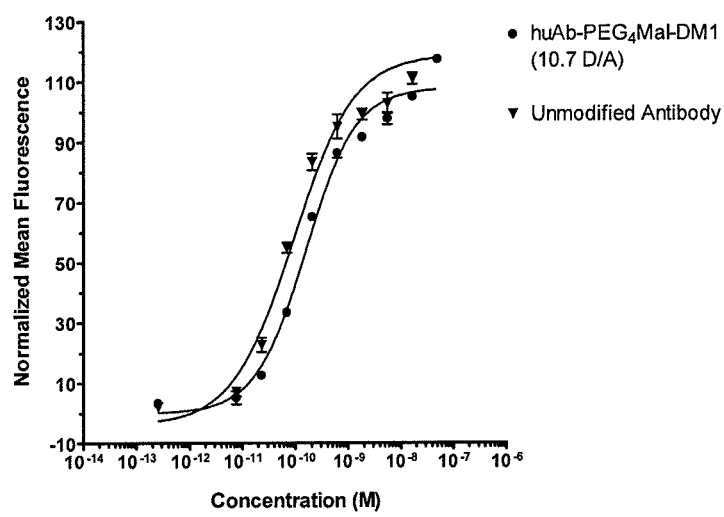
FIG. 24 shows FACS binding of HuAb-PEG4Mal-DM1 conjugate (10.7 maytansinoid/antibody) is similar to that of unmodified antibody.

FACS Binding of High Maytansinoid Bearing Antibody Species is Similar to that of Unmodified Antibody The binding of the high maytansinoid bearing conjugates of several antibodies were compared with unmodified antibodies against different targets such as EpCAM, CanAg, and CD56 by flow cytometry. Briefly, the antigen-positive cells were incubated with conjugates or unmodified antibodies at 4° C., then with a secondary antibody-FITC conjugate at 4° C., fixed with formaldehyde (1% in PBS) and analyzed by flow cytometry. No significant difference was observed between the binding of the conjugate versus that of the unmodified antibody for all the conjugates evaluated. An example is shown in FIG. 24, where a 10.7 maytansinoid bearing Ab-PEG$_4$-Mal-DM1 conjugate bound to antigen-positive cells with a high affinity similar to that of the unmodified antibody.

Example VI

In vitro Cytotoxicity Evaluation of Maytansinoid Conjugates of Antibodies with Thioether and Disulfide Linkers Containing Polyethyleneoxide Spacers (PEG$_n$, or (—CH$_2$—CH$_2$—O)$_n$)

The cytotoxic effects of the antibody-maytansinoid conjugates with thioether and disulfide linkers containing PEG$_n$ spacers were typically evaluated using a WST-8 cell-viability assay after a 4-5 day continuous incubation of the cancer cells with the conjugates. The antigen-expressing cancer cells (1000-5000 cells per well) were incubated in 96-well plates in regular growth medium containing fetal bovine serum with various concentrations of the antibody-maytansinoid conjugates for about 5 days. The WST-8 reagent was then added and the plate absorbance was measured at 450 nm after ~2-5 h. The survival fraction was plotted versus conjugate concentration to determine the IC$_{50}$ value (50% cell killing concentration) of the conjugate.

Figure 25:
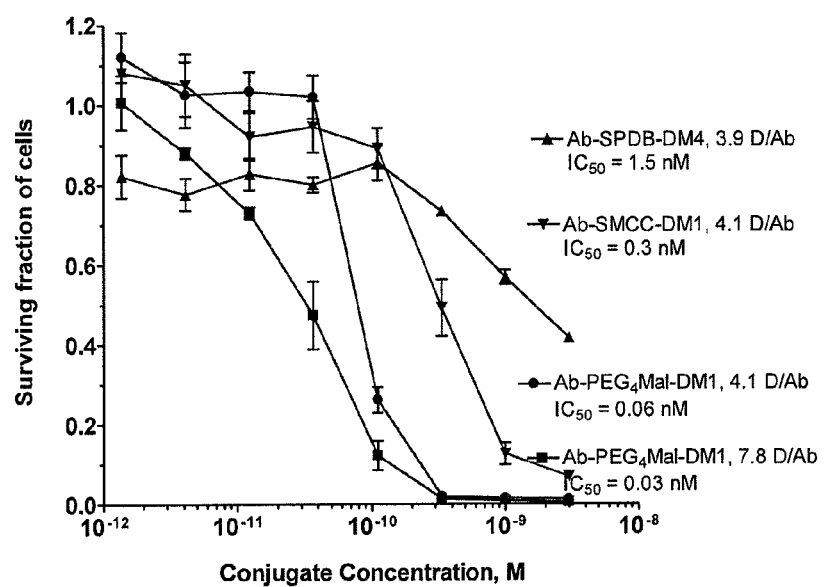
FIG. 25 shows cytotoxicity of anti-EpCAM antibody-maytansinoid conjugates on multi-drug resistant COLO205-MDR cells.

FIG. 25 shows the enhancement in potency of anti-EpCAM Ab-maytansinoid conjugates with increased drug load for the PEG$_4$ linked thioether conjugate (Ab-PEG$_4$-Mal-DM1), which also shows greater potency than the thioether-linked SMCC-DM1 and disulfide-linked SPDB-DM4 conjugates at similar drug loads of about 4 maytansinoid per antibody toward EpCAM antigen-positive COLO205-multi drug resistant cells (COLO205-MDR cells). The potency of the thioether-linked anti-EpCAM Ab-PEG$_4$-Mal-DM1 conjugate at maytansinoid loads of 4.1 and 7.8 is novel and potentially very promising for therapeutic applications.

Figure 26:
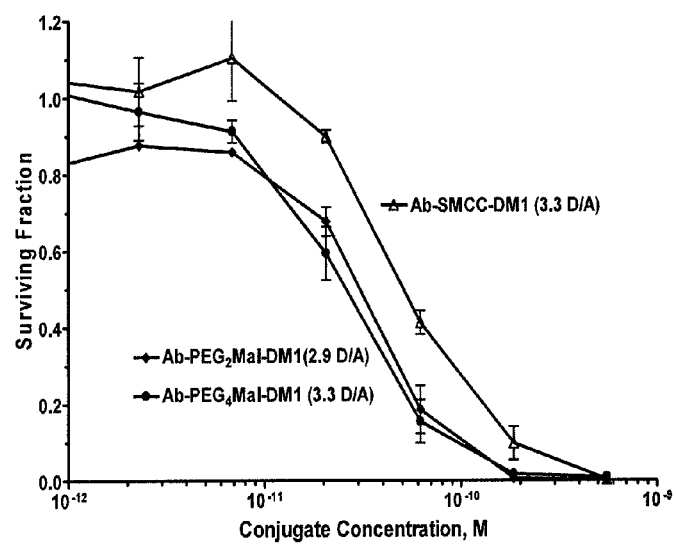
FIG. 26 shows cytotoxicity of anti-CanAg antibody-maytansinoid conjugates on multi-drug resistant COLO205-MDR cells.

FIG. 26 shows the cytotoxic activities of anti-CanAg Ab-maytansinoid conjugates against CanAg antigen-positive COLO205-MDR cells. Again, the thioether-linked Ab-PEG$_4$-Mal-DM1 and Ab-PEG$_2$-Mal-DM1 conjugates showed greater potency compared to the thioether-linked Ab-SMCC-DM1 conjugate with similar maytansinoid loads.

Figure 27:
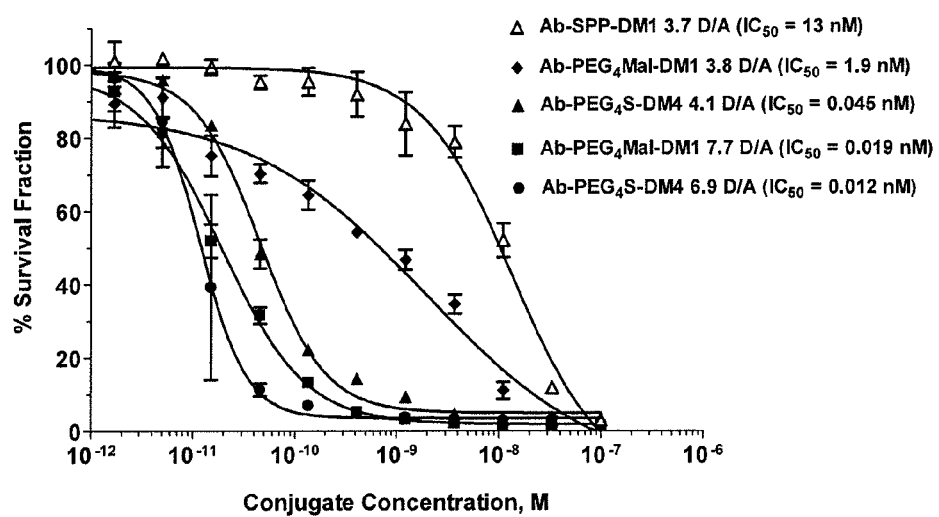
FIG. 27 shows cytotoxicity of anti-CD56 antibody-maytansinoid conjugates on Molp-8 multiple myeloma cells.

FIG. 27 shows the cytotoxic activities of the anti-CD56 antibody-maytansinoid conjugates with PEG-containing thioether and disulfide linkers on CD56-expressing Molp-8 multiple myeloma cells. The thioether-linked PEG4 conjugates with 7.7 drugs per antibody (Ab-PEG$_4$Mal-DM1) showed an unexpected 100-fold increase in cytotoxic potency (IC$_{50}$ value of 0.019 nM) compared to the conjugate bearing 3.8 drugs (IC$_{50}$=1.9 nM).

Figure 28:
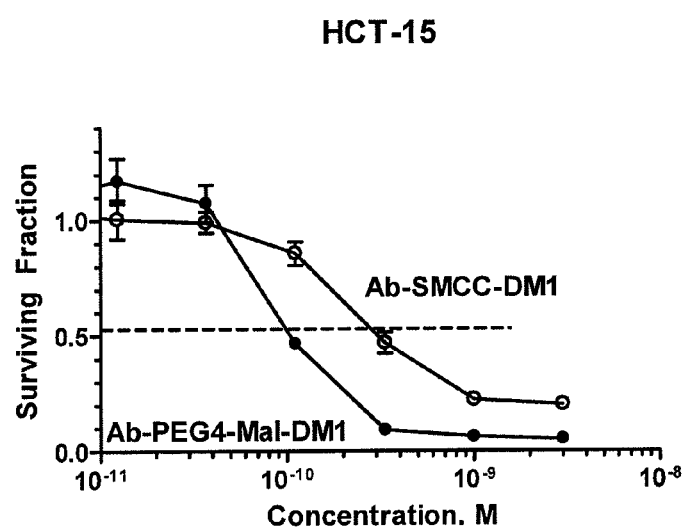
FIG. 28 shows cytotoxicity of anti-EpCAM antibody-maytansinoid conjugates on HCT15 cells.
Figure 29:
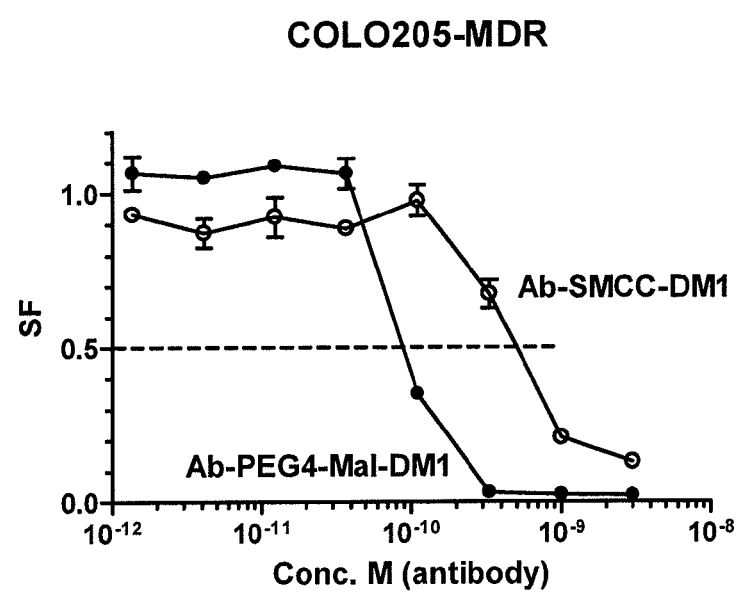
FIG. 29 shows cytotoxicity of anti-EpCAM antibody-maytansinoid conjugates on COLO 205 mdr cells.
Figure 37:
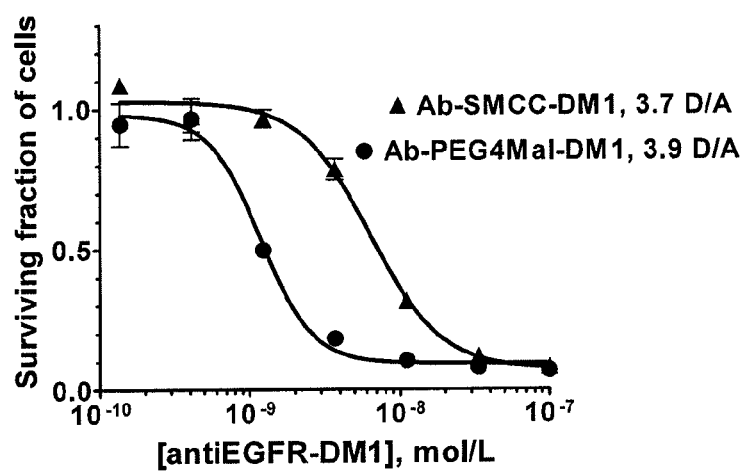
FIG. 37 shows cytotoxicity of Anti-EGFR Antibody-Maytansinoid conjugates on UO-31 Cells.

FIG. 28 shows the enhancement in potency of anti-EpCAM Ab-maytansinoid conjugates bearing a PEG$_4$ linked thioether conjugate (Ab-PEG$_4$-Mal-DM1), over the conventional thioether-linked SMCC-DM1 at similar drug loads of about 4 maytansinoid per antibody toward EpCAM-positive multi drug resistant HCT15 cells. The high potency of the thioether-linked anti-EpCAM Ab-PEG$_4$-Mal-DM1 conjugate is a novel finding and potentially very promising for therapeutic applications. FIG. 29 shows the enhancement in potency of anti-EpCAM Ab-maytansinoid conjugates bearing a PEG$_4$ linked thioether conjugate (Ab-PEG$_4$-Mal-DM1), over the conventional thioether-linked SMCC-DM1 at similar drug loads of about 4 maytansinoid per antibody toward EpCAM-positive multi drug resistant COLO 205 cells. The enhanced potency of the thioether-linked anti-EpCAM Ab-PEG$_4$-Mal-DM1 conjugate is a novel finding and potentially very promising for therapeutic applications. FIG. 37 shows the potent enhancement in cytotoxicity of anti-EGFR Ab-Maytansinoid conjugate with the hydrophilic thioether-bonded PEG$_4$ linker (Ab-PEG$_4$-Mal-DM1) compared to the non-hydrophilic SMCC-DM1 conjugate with 3.7 maytansinoid/Ab toward EGFR-positive UO-31 human renal carcinoma cells. The potency of the PEG$_4$-Mal-DM1 was about 10-fold greater than that of the SMCC-DM1 conjugate with the traditional linker.

Example VII

In Vivo Pharmacokinetics

The plasma pharmacokinetics of a humanized anti-CD56 antibody (Ab)-PEG$_4$-Mal-DM1 conjugate containing the hydrophilic PEG$_4$ linker and bearing 6.7 D/A (maytansinoid/antibody) was compared with that of an Ab-SMCC-DM1 conjugate containing a traditional aliphatic carbon chain linker and bearing 4 D/A (FIG. 38 A). CD1 mice were injected intravenously, by a single bolus, of 5 mg/kg conjugates (antibody-based dose; 3 mice per group). Plasma samples were collected at several time points up to 4 weeks. The plasma samples were analyzed for antibody concentration and for conjugate concentration using ELISA. For antibody ELISA, the plasma samples were added to microtiter plates containing coated, immobilized goat-anti-human IgG (H+L) antibody, washed, and detected using horseradish peroxidase-conjugated goat-anti-human IgG (Fe) antibody. For conjugate concentration, the plasma samples were added to microtiter plates containing coated, immobilized goat-anti-human IgG (H+L) antibody, washed, and detected using biotinylated anti-maytansine antibody and alkaline phosphatase-conjugated streptavidin. Both antibody concentration and conjugate concentration ELISA results demonstrated that the Ab-PEG$_4$-Mal-DM1 conjugate with hydrophilic PEG$_4$ linker bearing the high 6.7 DM1/Ab load was well retained in plasma over the 4 week study period.

FIG. 38 A shows the in vivo pharmacokinetics of an Anti-body-Maytansinoid conjugate using the PEG$_4$ linker with a high maytansinoid load (6.7 DM1/Ab) compared to the standard linker conjugate bearing 4 DM1/Ab. Even with the high maytansinoid load, the PEG$_4$ linked thioether conjugate (Ab-PEG$_4$-Mal-DM1) with 6.7 maytansinoid/Ab has a longer half life than the standard conjugate. In another example, the plasma pharmacokinetics of a humanized C242 Ab-PEG$_4$-Mal-3H-DM1 conjugate with $^3$H-labeled DM1 (at 3.3 maytansinoid/Ab) was compared with unconjugated antibody and with Ab-SMCC-3H-DM1 conjugate containing a traditional aliphatic carbon chain linker and bearing a similar 4.2 D/A load, in CD-1 mice at 10-12 mg/kg i.v. dose (FIG. 38 B). The Ab-PEG$_4$-Mal-3H-DM1 conjugate showed higher plasma concentrations over 4 weeks compared to the traditional SMCC-linker conjugate with a similar maytansinoid load, as measured by both antibody concentrations (ELISA; FIG. 38 B) and conjugate concentrations (3H-label counts). The half life of the PEG$_4$-Mal linked conjugate was 16 days compared to 12.6 days for the SMCC-linked conjugate and thus much improved over the SMCC conjugate (FIG. 38 B). Importantly, the area under the curve (AUC) of the Ab-PEG$_4$-Mal-DM1 conjugate with 3.3 D/A at 10 mg/kg i.v. dosage (AUC=38790 h·μg/mL) was similar to that of the unconjugated antibody at a similar dosage of 12 mg/kg i.v. (AUC=38798 h·μg/mL) and much better than that of the Ab-SMCC-DM1 conjugate with 4.2 D/A at 10 mg/kg i.v. dosage (AUC=25910 h·μg/mL) in CD-1 mice (FIG. 38 B).

Example VIII

Comparison of In Vivo Anti-Tumor Activity of the Anti-EpCAM-maytansinoid Conjugates, muB38.1-MCC-DM1 and muB38.1-PEG4-mal-DM1 Conjugates Towards Resistant Colon Cancer (HCT15) Xenografts The anti-tumor effect of muB38.1-MCC-DM1 and muB38.1-PEG4-mal-DM1 conjugates was evaluated in a xenograft model of human colon carcinoma, HCT15, which is shown to overexpress P-glycoprotein and be resistant to various drugs. HCT15 cells were injected subcutaneously in the area under the right shoulder of SCID mice (1×10$^7$ cells per animal). When the tumor volumes reached approximately 140 mm$^3$ in size (9 days post tumor cell inoculation), the mice were randomized by tumor volume and divided into three groups (5 animals per group), each group was treated with a single i.v. bolus of either, muB38.1-MCC-DM1 (20 mg conjugate protein/kg), muB38.1-PEG4-mal-DM1 (20 mg conjugate protein/kg) or phosphate-buffered saline (vehicle control). Tumor growth was monitored by measuring tumor size twice per week. Tumor size was calculated with the formula: length×width×height×½.

Figure 30:
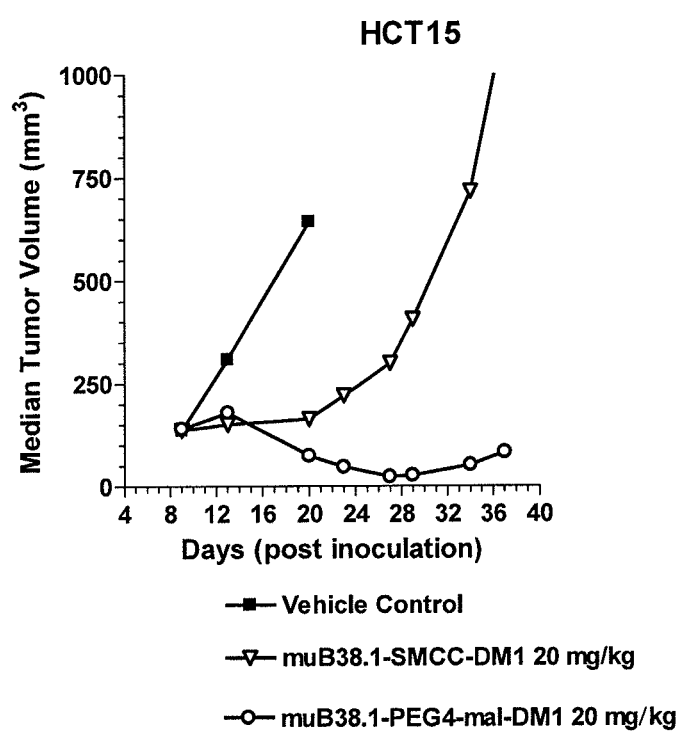
FIG. 30 shows in vivo anti-tumor activity of anti-EpCAM antibody-maytansinoid conjugates on HCT15 xenografts.

The mean change in tumor volumes is shown for example in FIG. 30. In the PBS control group, tumors reached a tumor volume of 600 mm$^3$ by day 20, post cell inoculation. Treatment with muB38.1-MCC-DM1, resulted in tumor growth delay of 15 days. Treatment with muB38.1-PEG4-mal-DM1 showed more anti-tumor effect with two of five animals having complete tumor regressions, lasting 44 days and three animals with a tumor growth delay of 32 days.

Thus, the conjugate of the present invention, muB38.1-PEG4-mal-DM1 is significantly more efficacious than muB38.1-MCC-DM1 in this human colon cancer xenograft model.

Example IX

Comparison of the In Vivo Anti-Tumor Activity of the Anti-EpCAM-Maytansinoid Conjugates (muB38.1-MCC-DM1 and muB38.1-PEG4-mal-DM1) Towards Xenografts of Resistant Colon Cancer (COLO205-MDR)

The anti-tumor effect of muB38.1-MCC-DM1 and muB38.1-PEG4-mal-DM1 conjugates was evaluated in a xenograft model of human colon carcinoma, COLO205-MDR, which was engineered to overexpress P-glycoprotein. COLO205-MDR cells were injected subcutaneously in the area under the right shoulder of SCID mice (1×10$^7$ cells per animal). When the tumor volumes reached approximately 170 mm$^3$ in size (8 days post cell inoculation), the mice were randomized into three groups (6 animals per group), each group was treated with a single i.v. bolus of either muB38.1-MCC-DM1 (20 mg conjugate protein/kg), muB38.1-PEG4-mal-DM1 (antibody dose 20 mg/kg) or phosphate-buffered saline (vehicle control). Tumor growth was monitored by measuring tumor size twice per week. Tumor size was calculated with the formula: length×width×height×¼.

Figure 31:
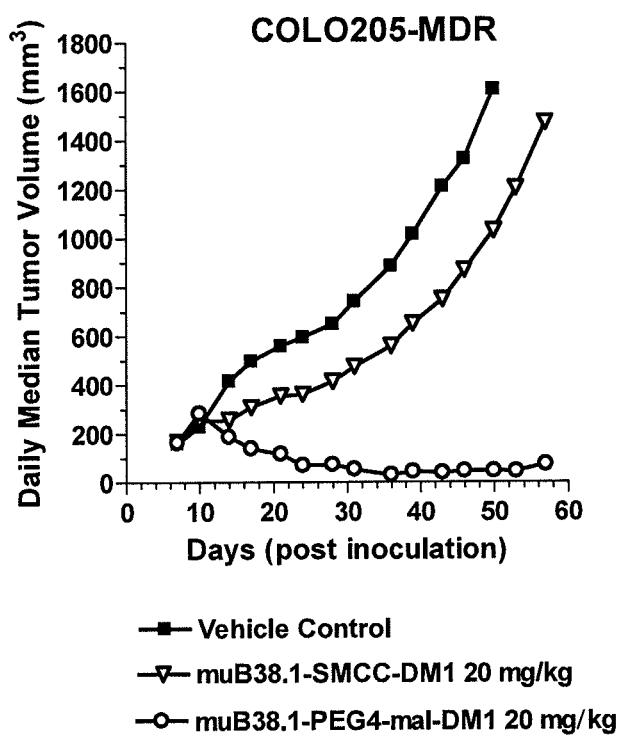
FIG. 31 shows in vivo anti-tumor activity of anti-EpCAM antibody-maytansinoid conjugates on COLO205 mdr xenografts.

The mean change in tumor volume is shown for example in FIG. 31. In the PBS control group, tumors grew to about 1000 mm$^3$ in 38 days. Treatment with muB38.1-MCC-DM1 resulted in tumor growth delay of 14 days. Treatment with muB38.1-PEG4-mal-DM1 had a remarkable anti-tumor effect resulting in complete tumor regressions in all six animals (FIG. 31).

Figure 32:
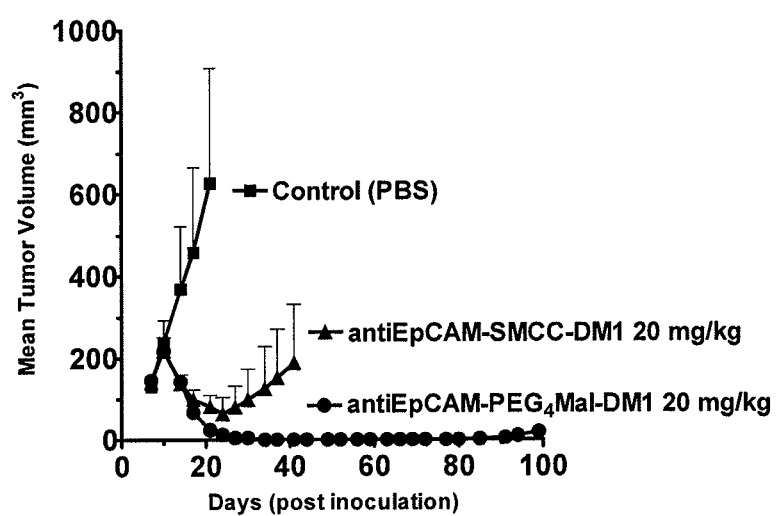
FIG. 32 shows in vivo anti-tumor activity of anti-EpCAM antibody-maytansinoid conjugates on COLO 205 xenografts.

A similar experiment was also conducted against COLO 205 xenografts. Again treatment with B38.1-PEG4-mal-DM1 is more efficacious resulting in complete tumor regression, while the standard SMCC conjugate only shows a modest tumor growth delay (FIG. 32).

Figure 33:
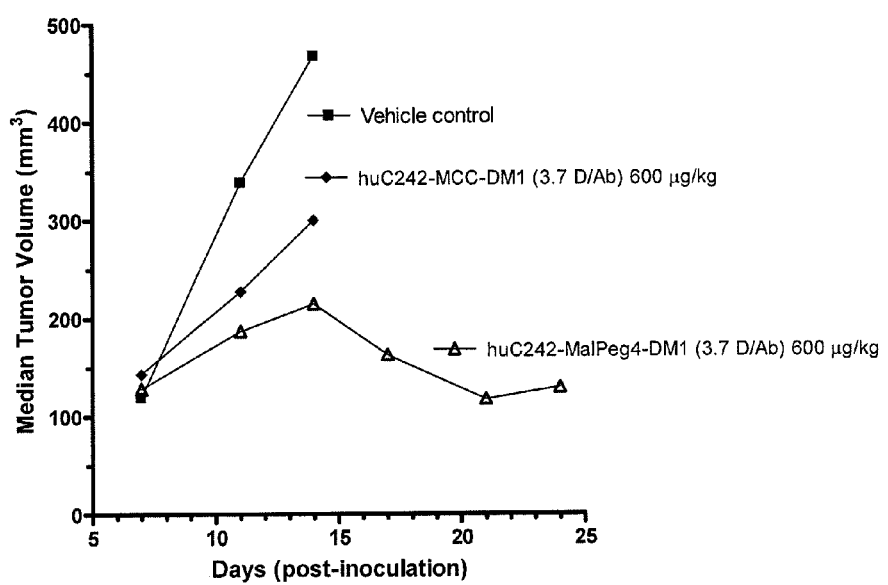
FIG. 33 shows in vivo anti-tumor activity of anti-CanAg antibody-maytansinoid conjugates on COLO 205 mdr xenografts.

Similar results were obtained with conjugates of a humanized anti-CanAg antibody (FIG. 33).

Thus, the conjugate of the present invention, muB38.1-PEG4-mal-DM1 is significantly more efficacious than the conjugate muB38.1-MCC-DM1, prepared with the previously described linker, in this human colon cancer xenograft model.

Example X

Evaluation of PEG Length

Figure 34:
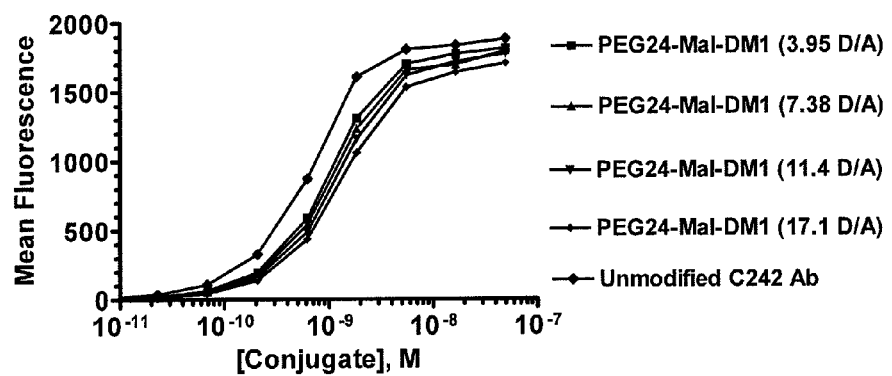
FIG. 34 shows the binding of anti-CanAg antibody (huC242)-PEG24-Mal-DM1 conjugate with up to 17 D/A.
Figure 35:
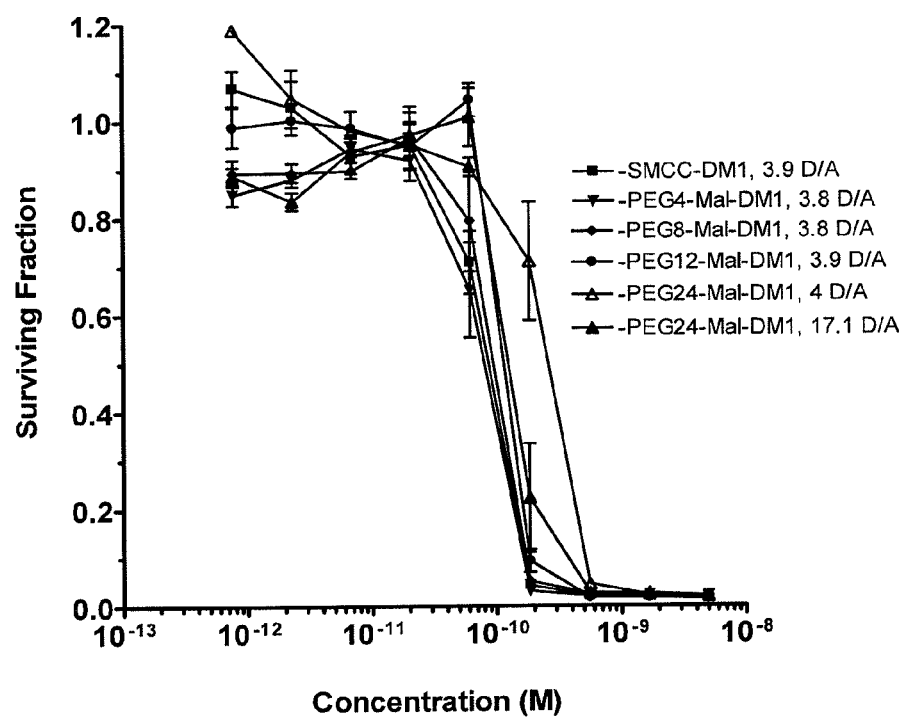
FIG. 35 shows in vitro potency of Anti-CanAg antibody (huC242)-PEG24-Mal-DM1 conjugates with 4 to 17 D/A toward COLO 205 cells.
Figure 36:
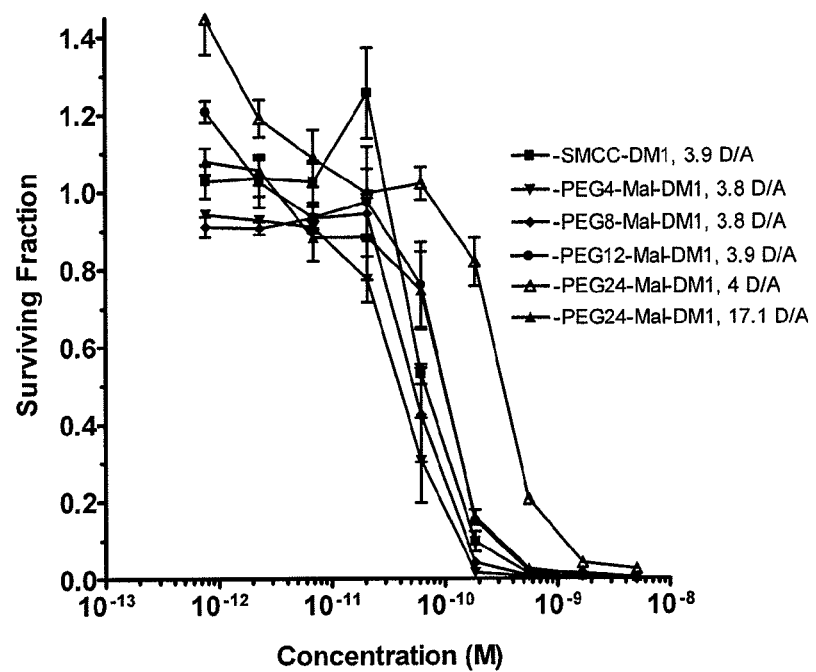
FIG. 36 shows in vitro potency of anti-CanAg antibody (huC242)-PEG24-Mal-DM1 conjugates with 4 to 17 D/A toward multi-drug resistant (pgp+) COLO205-MDR cells.

Several Ab-PEG$_n$-Mal-DMx conjugates were prepared with PEG$_4$, PEG$_8$, PEG$_{12}$, PEG$_{24}$ linkers and with various numbers of DMx incorporated per antibody. FIG. 34 demonstrates that an Ab-PEG$_{24}$-Mal-DM1 conjugate with a very high 17.1 D/A load shows a similar binding to antigen-expressing cancer cells as the unmodified antibody (binding measured in relative mean fluorescence RMF units by flow cytometry). Also, Ab-PEG$_8$-Mal-DM1 and Ab-PEG$_{12}$-Mal-DM1 conjugates bearing 4 to 8 D/A show binding similar to unmodified antibody by cell-binding flow cytometry. The Ab-PEG$_n$-Mal-DMx conjugates prepared with PEG$_4$, PEG$_8$, PEG$_{12}$, PEG$_{24}$ linkers were potent in cytotoxicity toward antigen-positive cells. FIG. 35 demonstrates that the anti-CanAg antibody (huC242)-PEG$_n$-Mal-DM1 conjugates with 4 to 17 D/A killed the CanAg antigen-positive COLO205 cells with potent IC$_{50}$ of about 0.1-0.5 nM upon incubation for 5 days. The pgp-expressing multi-drug resistant COLO205-MDR cells were killed by the huC242-PEG$_n$-Mal-DM1 conjugates bearing 4 to 17 D/A in a potent manner with IC$_{50}$ of about 0.05 to 0.5 nM (FIG. 36). The PEG$_{24}$-Mal-DM1 conjugate with high, 17.1 D/A was more potent in cytotoxicity than the PEG$_{24}$-Mal-DM1 conjugate with 4 D/A (FIGS. 34, 36).

Example XI

Figure 39:
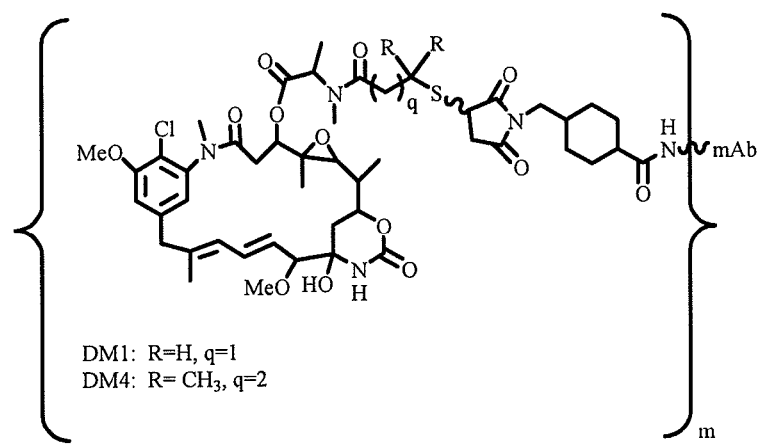
FIG. 39 shows a structural representation of a thiosuccinimidyl-linked conjugate of the present invention (mAb=antibody, m=2-8).
Figure 41:
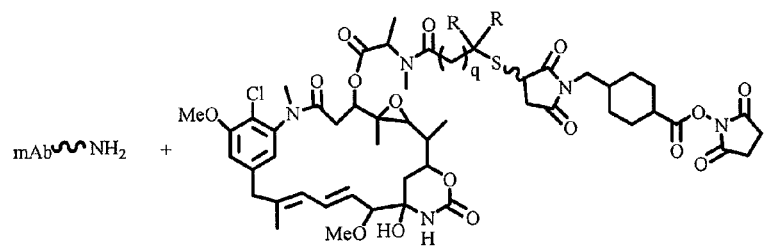
FIG. 41 shows a conjugation procedure for a thiosuccinimidyl-linked conjugate prepared with compounds of the present invention (mAb=antibody, m=2-8).
Figure 41:
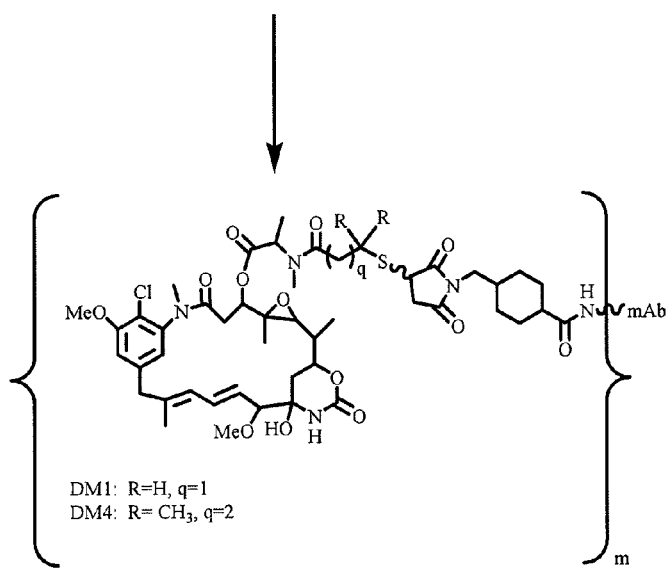
Figure 43:
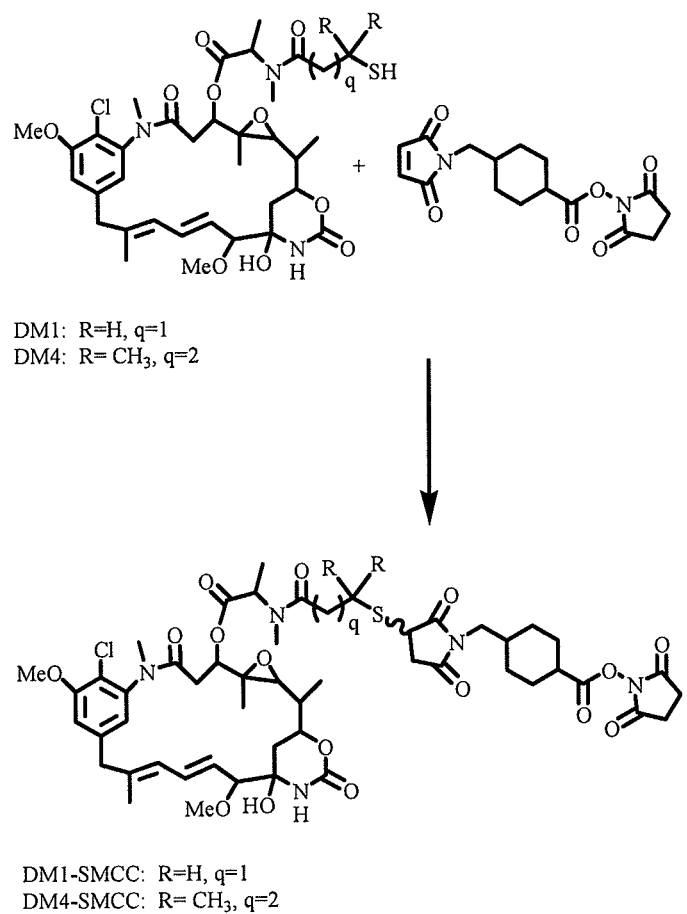
FIG. 43 shows a synthetic scheme for amine-reactive non-cleavable thiosuccinimidyl-linked compounds of the present invention, which contain a ring between the maleimide and NHS ester.
Figure 44:
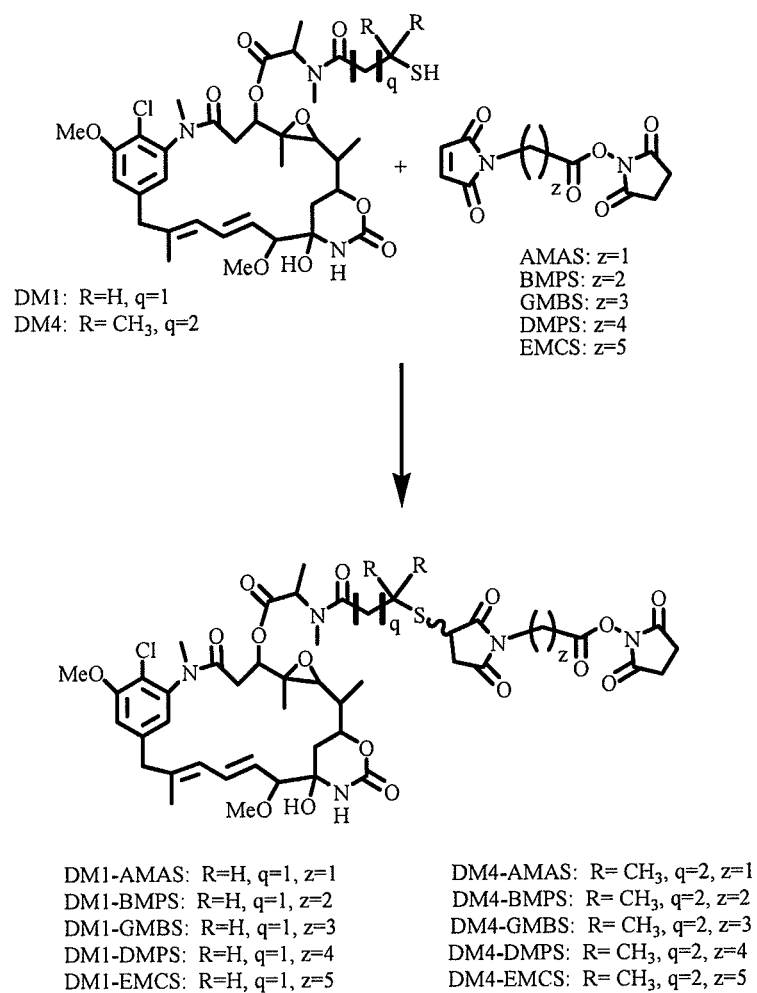
FIG. 44 Shows a synthetic scheme for the preparation of the amine-reactive non-cleavable thiosuccinimidyl-linked compounds which contain a straight chain hydrocarbon between the maleimide and NHS ester.

Conjugation of Maytansinoids Bearing a Non-Cleavable Thiosuccinimidyl Moiety that Contains an Amine Reactive Group to an Antibody The N-hydroxysuccinimide ester of a maytansinoid bearing a non-cleavable thiosuccinimidyl group was used to conjugate antibody using a one-step method (FIG. 41). The sulfhydryl-bearing maytansinoid was modified with a heterobifunctional, maleimide-bearing crosslinker and isolated (FIG. 43), prior to conjugation with antibody to give a non-cleavable thiosuccinimidyl-linked antibody maytansinoids conjugate (FIG. 39). The reaction was done with the SMCC reagent, which contains a hydrocarbon ring between the maleimide and the NHS ester, a similar method could be used to react a sulfhydryl-bearing maytansinoid to a heterobifunctional linker that contains a straight chain hydrocarbon between the maleimide and the NHS ester (FIG. 44).

Synthesis of DM1-SMCC

A round bottom flask was charged with N$^{2'}$-Deacetyl-N$^{2'}$-(3-mercapto-1-oxopropyl)-maytansine (DM1, 67.9 mg, 0.092 mmol), Succinimidyl-4-(N-maleimidomethyl)cyclohexane-1-carboxylate (SMCC, 32.1 mg, 0.096 mmol, 1.05 equivalents) and THF (4 mL). The solution stirred as the reagents were dissolved in the solvent to yield a clear, colorless solution. Phosphate buffer, pH 6, (4 mL, 100 mM Potassium Phosphate, 2 mM EDTA) was then added. The reaction flask was equipped with a septum and stir bar and the reaction proceeded at room temperature with vigorous stirring. The reaction appeared complete within 30 minutes as indicated by reverse-phase HPLC. Following reaction completion, the reaction volume was reduced in vacuo to give a white solid/residue. The product was isolated by silica gel chromatography, eluting with a mixture of 3% methanol in methylene chloride. Product containing fractions were combined and concentrated to dryness in vacuo to give 63 mg (63.9% yield) DM1-SMCC as a white solid. Mass spectral analysis of the isolated product gave the expected m+Na$^+$ (m/z 1094.4) and m+Cl$^-$ (m/z 1106.2) major molecular ions (FIG. 43).

One-Step Conjugation of Antibody with DM1-SMCC

A 10 mM stock (w/v) of DM1-SMCC reagent was prepared in DMA (10.7 mg/mL). The stock solution was diluted in EtOH and the absorbance was measured at 280 nm against a reagent blank of EtOH and DMA. The concentration of stock DM1-SMCC reagent was calculated by using an extinction coefficient of 5700 M$^{-1}$ at 280 nm which is the extinction coefficient of DM1 at this wavelength. Since the real extinction coefficient of DM1-SMCC has not been determined this is only an estimate of concentration.

The antibody was conjugated with DM1-SMCC at 5 mg/mL using a 7-fold molar excess of the reagent. A titration of antibody with several excesses of DM1-SMCC was performed initially to determine the desired DM1:Ab ratio, typically this range is 6-10-fold molar excess for human antibodies. The reaction was carried out in pH 7.5 buffer with DMA (5% v/v) for 90 minutes at room temperature. The reaction mixture was then kept at 4° C. for 12-36 hours. The conjugate was then purified over a NAP-5 (Sephadex G25) column equilibrated in pH 5.5 citrate buffer, filtered and dialyzed against the pH 5.5 citrate buffer to remove any unreacted free drug. Following dialysis, the conjugate had 3.1 DM1 molecules linked per mole of antibody and no detectable free drug present in the conjugate (FIG. 39, m=3.1). The number of DM1 molecules per Ab antibody molecule (average) in the final conjugate was measured by determining absorbance of the conjugate at 252 and 280 nm and using known extinction coefficients for DM1 and antibody at these two wavelengths.

SEC HPLC was performed on the conjugate to show that it was 96.8% monomeric following conjugation.

The final conjugate was also analyzed by size exclusion LC/MS. The conjugate made via the method described in this invention shows the desired MS spectrum of deglycoslyated conjugate containing only the expected distribution of peaks, FIG. 45.

Synthesis of DM4-SMCC

A round bottom flask was charged with N$^{2'}$-deacetyl-N$^{2'}$-(4-mercapto-4-methyl-1-oxopentyl)maytansine (DM4, 22.0 mg, 0.0282 mmol) and Succinimidyl-4-(N-maleimidomethyl)cyclohexane-1-carboxylate (SMCC, 24.2 mg, 0.0723 mmol, 2.50 equivalents) and glass distilled THF (1 mL). The solution stirred as the reagents were dissolved in the solvent to yield a clear, colorless solution. Phosphate buffer pH 6 (1 mL, 100 mM Potassium Phosphate, 2 mM EDTA) was then added. The reaction flask was equipped with a septum and stir bar and the reaction proceeded at room temperature with vigorous stirring. The reaction appeared complete after 7 hours, as indicated by reverse-phase HPLC. Following reaction completion the product was extracted into ethyl acetate (3×25 mL), washed with brine (5 mL) and dried in vacuo. The product was isolated by silica gel chromatography, eluting with a mixture of 3% ethanol in methylene chloride. Product containing fractions were combined and concentrated in vacuo to give 19.74 mg (62.8% yield) of DM4-SMCC. Mass spectral analysis of the isolated product gave the expected m+Na$^+$ (m/z 1136.4) and m+Cl$^-$ (m/z 1148.4) major molecular ions.

One-Step Conjugation of Antibody with DM4-SMCC

A solution of humanized antibody (2.5 mg/mL) in aqueous buffer (100 mM sodium phosphate), pH 8.0, was incubated with a 10-fold molar excess of DM4-SMCC in dimethyl sulfoxide (DMSO) to give a final DMSO concentration of 20%. The conjugation proceeded for one hour at ambient temperature. The conjugate was purified by passage over a Sephadex G25 gel filtration column equilibrated in pH 5.5 buffer (10 mM histidine, 130 mM glycine, 5% (w/v) sucrose, pH 5.5). The number of DM4 molecules linked per antibody molecule (average) in the final conjugate was measured by determining absorbance of the conjugate at 252 and 280 nm and using known extinction coefficients for DM4 and antibody at these two wavelengths.

Following purification, the conjugate had 3.7 DM4 molecules linked per molecule of antibody. SEC analysis was performed on the final conjugate to show that it was >95% monomeric however >5% free drug species was present on the final conjugate. Dialysis of the conjugate may have reduced the presence of undesired free drug species.

Example XII

Figure 40:
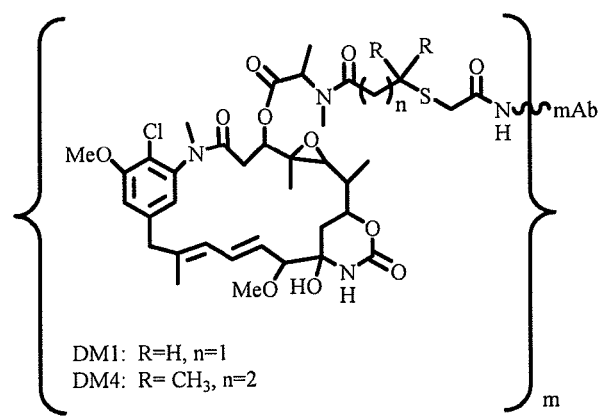
FIG. 40 shows a structural representation of a thioacetamidyl-linked conjugate of the present invention (mAb=antibody, m=2-8).
Figure 42:
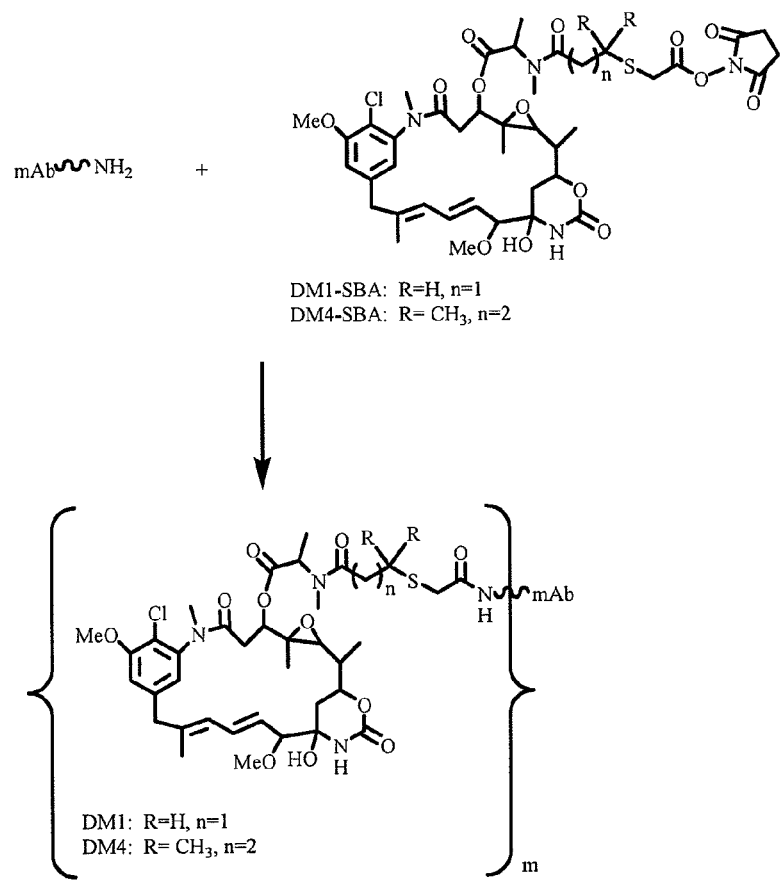
FIG. 42 shows a conjugation procedure for a thioacetamidyl-linked conjugate prepared with compounds of the present invention (mAb=antibody, m=2-8).
Figure 48:
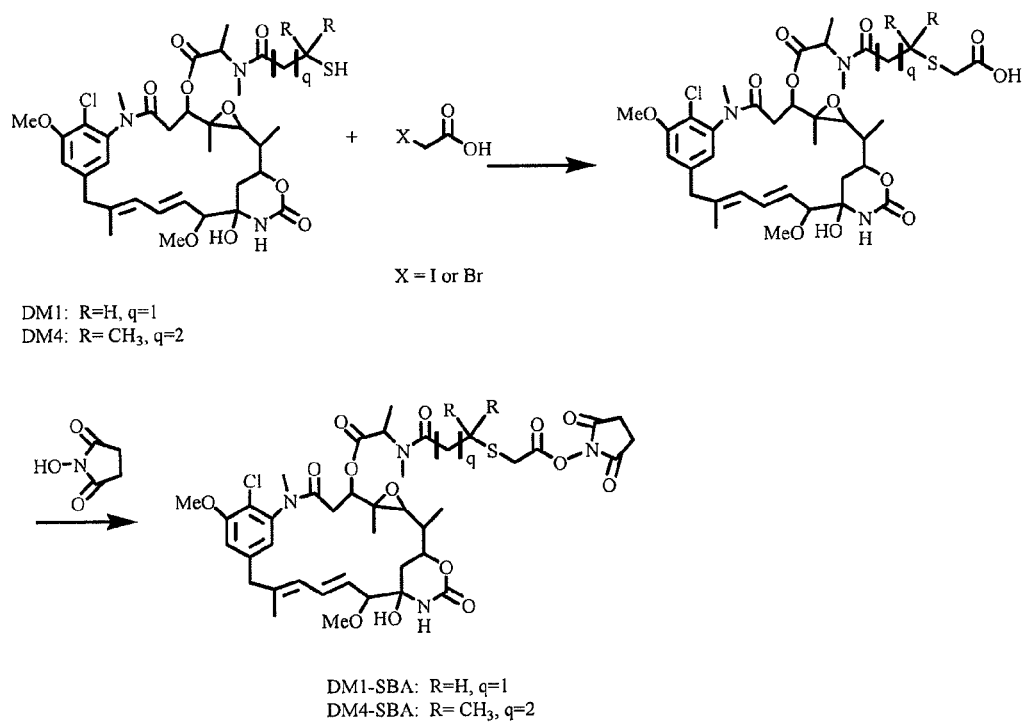
FIG. 48. Shows a synthetic scheme for two step preparation of non-cleavable thioacetamidyl-linked compounds of the present invention.

Conjugation of Maytansinoids Bearing a Non-Cleavable Thioacetamidyl Moiety that Contains an Amine Reactive Group to an Antibody The sulfhydryl bearing maytansiniod DM1 was reacted with bromoacetic acid to give the thioacetamidyl-linked carboxylic acid derivative. Esterification with N-hydroxysuccinimide gave the amine reactive non-cleavable, thioacetamidyl-linked maytansinoid (FIG. 48). One-step conjugation of the isolated compound with antibody (FIG. 42) gave a non-cleavable antibody maytansinoid conjugate (FIG. 40).

Figure 49:
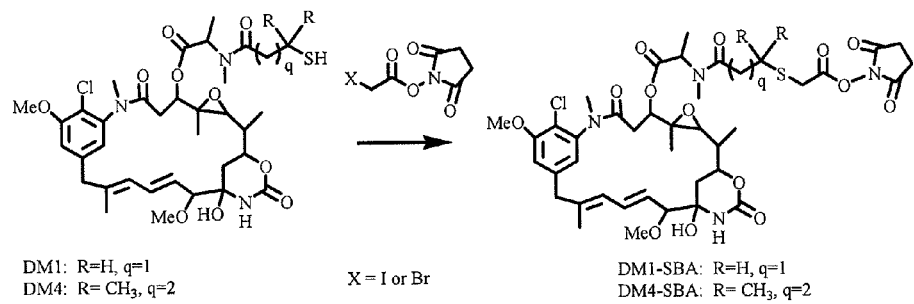
FIG. 49. Shows a synthetic scheme for the two step preparation of non-cleavable thioacetamidyl-linked compounds of the present invention.

Alternatively, the sulfhydryl-bearing maytansinoid DM4 was modified with a heterobifunctional, haloacetamide-bearing crosslinker to give an amine reactive maytansinoid bearing a thioacetamidyl moiety (FIG. 49). One-step conjugation of the isolated compound with antibody (FIG. 42) gave a non-cleavable thioacetamidyl-linked antibody maytansinoid conjugate (FIG. 40).

Synthesis of DM1-SBA

A round bottom flask was charged with $N^{2'}$-Deacetyl-$N^{2'}$-(3-mercapto-1-oxopropyl)-maytansine (DM1, 183.4 mg, 0.248 mmol) and anhydrous N,N-dimethylformamide (DMF, 3 mL). The reaction solution was stirred as bromoacetic acid (37.9 mg, 0.273 mmol, 1.1 equivalents) and 1,8-Diazabicyclo [5.4.0]undec-7-ene (DBU, 75.6 mg, 0.497 mmol) were sequentially added. The flask was equipped with a septum and a stir bar and the reaction proceeded at room temperature with vigorous stirring for 1 hour. Following reaction completion the reaction volume was reduced to a crude oil in vacuo. The crude product was dissolved in a minimal volume of methylene chloride and the product was isolated by silica gel chromatography, eluting with a mixture of 5% ethanol, 0.5% acetic acid and 94.5% methylene chloride. Product containing fractions were combined and the volume was reduced in vacuo to give 158.8 mg (80.4% yield) of the thioacetamidyl-linked DM1 carboxylic acid derivative with 94.6% purity by HPLC.

A round bottom flask was charged with the product of the previous reaction (158.8 mg, 0.199 mmol) and methylene chloride (15 mL). N-hydroxysuccinimide (NHS, 25.2 mg, 0.219 mmol, 1.1 equivalents) and 1-Ethyl-3-(3-dimethylaminopropyl)-carbodiimide (EDC, 57.2 mg, 0.298 mmol) were then added. The reaction proceeded with stirring at room temperature until completion. Following reaction completion (~45 min.), the reaction mixture was diluted with ethyl acetate (20 mL), transferred to a separatory funnel, washed with phosphate buffer pH 6 (15 mL, 100 mM potassium phosphate, 2 mM EDTA) and brine (7 mL), dried over anhydrous $Na_2SO_4$ and concentrated in vacuo to give a crude off-white solid. The product was isolated by silica gel chromatography eluting with a mixture of 10% 1,2-dimethoxyethane in ethyl acetate. Product containing fractions were combined and concentrated in vacuo to give 34.5 mg (19.4% yield) of DM1-SBA with 96.0% purity by reverse phase HPLC. Mass spectral analysis of the isolated product gave the expected m+Na$^+$ (m/z 915.2) and m+Cl$^-$ (m/z 927.0) major molecular ions.

One-Step Conjugation of Antibody with DM1-SBA

A 10.8 mM stock (w/v) of DM1-SBA reagent was prepared in DMA. The antibody was conjugated with DM1-SBA at 2.5 mg/mL using a 10.2-fold molar excess of the reagent. The reaction was carried out in pH 7.5 buffer (100 mM potassium phosphate) with DMA (10% v/v) for 90 minutes at room temperature. The conjugate was then purified over a 5300 gel filtration (Sephadex 5300) column eluting with pH 6.5 buffer (10 mM potassium phosphate, 140 mM sodium chloride). Following purification, the conjugate had 3.7 DM1 molecules linked per mole of antibody and ~0.18% free drug (FIG. 40, m=3.7).

SEC HPLC was performed on the conjugate to show that it was 99.6% monomeric following conjugation.

Synthesis of N-Succinimidyl Bromoacetate

Also Commercially Available

A 100 mL round bottom flask was charged with 2-bromoacetic acid (2.79 g, 20.08 mmol), N-hydroxysuccinimide (2.54 g, 22.12 mmol) and methylene chloride (30 mL). The solution stirred in an ice bath as N—N-dicyclohexylcarbodiimide (DCC, 4.46 g, 22.14 mmol) was added. The reaction stirred in the ice bath for one hour and an additional hour at room temperature.

The reaction mixture was filtered through a sintered glass funnel and concentrated in vacuo to give a crude white solid. The solid was dissolved in warm methylene chloride (30 mL) and recrystallized with hexanes (25 mL). The solid was collected by filtration, washed with hexanes and dried in vacuo to give 3.99 g (84% yield) of N-succinimidyl bromoacetate as a white solid. $^1$H NMR (CDCl$_3$) δ 2.864 (s, 4H) and 4.100 (s, 2H) ppm.

Synthesis of DM4-SBA

A round bottom flask was charged with $N^{2'}$-deacetyl-$N^{2'}$-(4-mercapto-4-methyl-1-oxopentyl)maytansine (DM4, 71.9 mg, 0.092 mmol) and anhydrous N,N-dimethylformamide (DMF, 2.5 mL). The reaction was placed under an argon atmosphere and N-succinimidyl bromoacetate (SBA, 23.9 mg, 0.101 mmol, 1.1 equivalents) and 1,8-Diazabicyclo [5.4.0]undec-7-ene (DBU, 14.7 mg, 0.097 mmol, 1.05 equivalents) were sequentially added. The flask was equipped with a septum and a stir bar and the reaction proceeded at room temperature with vigorous stirring until completion. The product was isolated by preparative cyano HPLC in a single injection, eluting with a gradient of 15-65% ethyl acetate in hexanes over 30 minutes followed by an increase of 65-95% ethyl acetate over 10 minutes. Under these conditions DM4-SBA eluted between 22-24 minutes. The product was collected and concentrated in vacuo to give 50.1 mg (55.2% yield) of the desired DM4-SBA (95% purity) product. Mass spectral analysis of the isolated product gave the expected m+Na$^+$ (m/z 957.4) and m+Cl$^-$ (m/z 969.2) major molecular ions.

Example XIII

Figure 45:
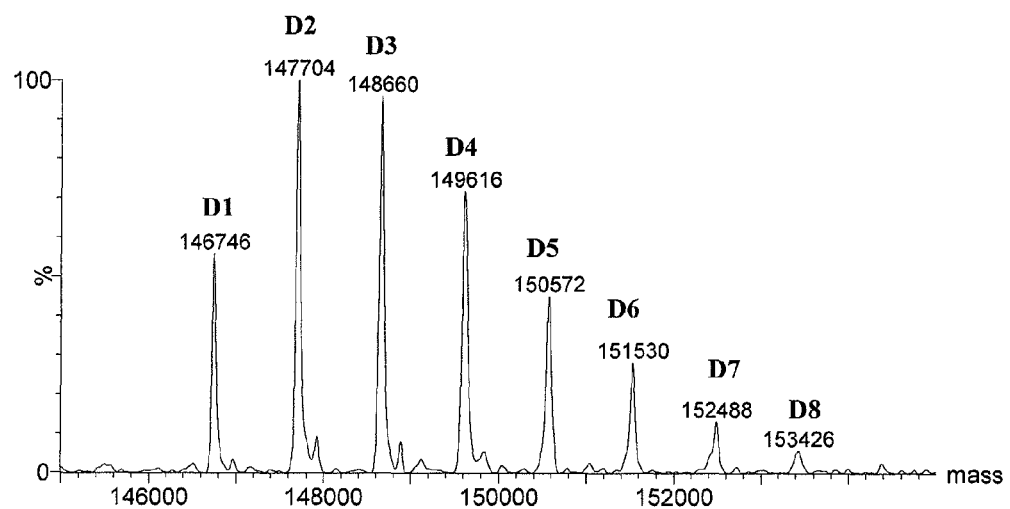
FIG. 45. Shows mass spectrum (MS) of deglycosylated mAb-SMCC-DM1 conjugate prepared with compounds of the present invention (3.42 DM1/mAb, average).
Figure 46:
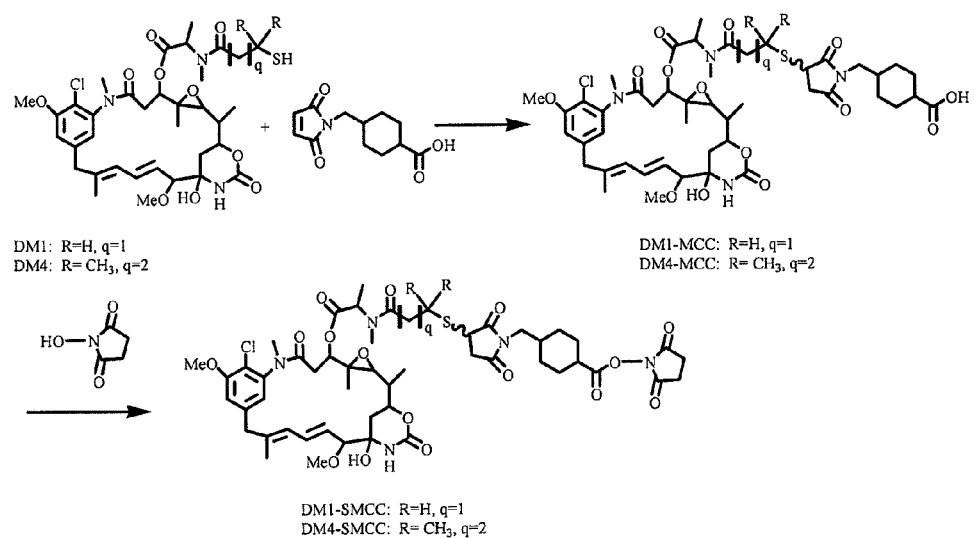
FIG. 46. shows a synthetic scheme for the two step preparation of the amine-reactive thiosuccinimidyl-linked compounds which contain a cyclolkyl group between the maleimide and NHS ester.
Figure 47:
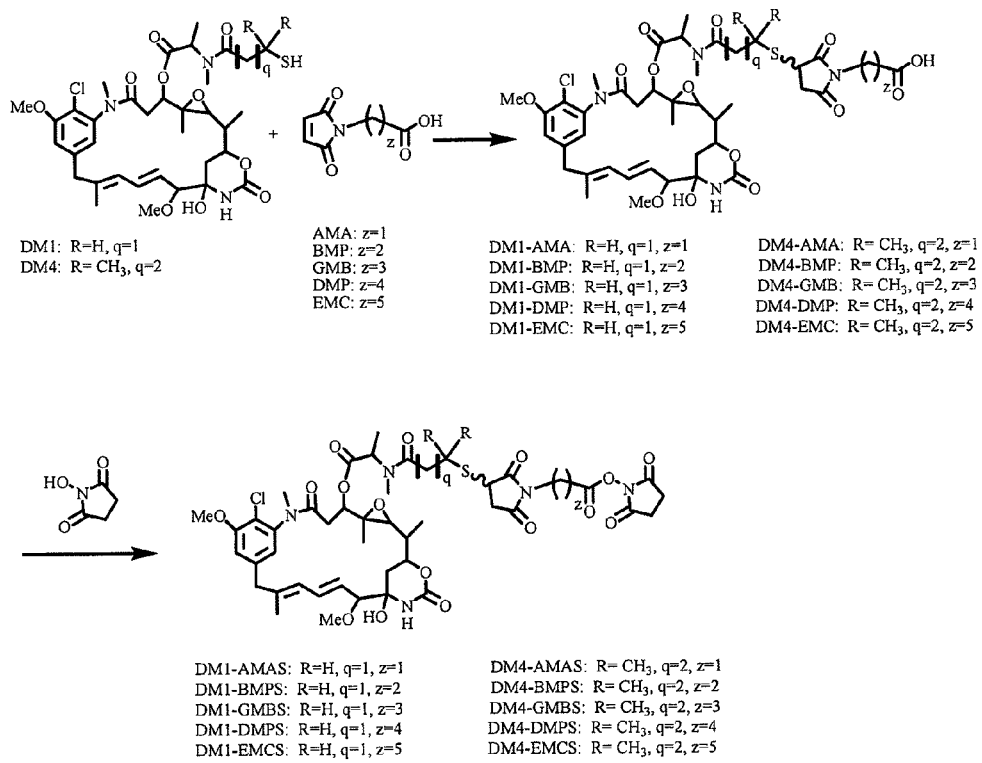
FIG. 47. shows a representative synthetic scheme for the two step preparation of the amine-reactive non-cleavable thiosuccinimidyl-linked compounds containing a ring (E.G. a cycloakyl group) between the maleimide and NHS ester.
Figure 50:
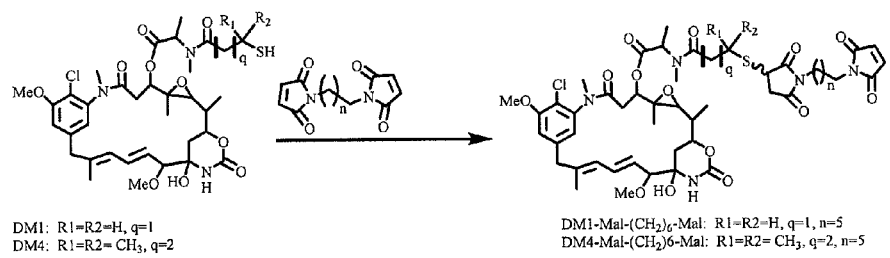
FIG. 50. Shows structures for non-cleavable thiosuccinimidyl-linked conjugates of the present invention (mAb=antibody, m=2-8).

Preparation of Non-Cleavable Thiosuccinimdyl-Linked Maytansinoid Derivatives Bearing a Carboxyl Moiety Sulfhydryl-bearing maytansinoids, such as DM1 and DM4, may be modified to give non-cleavable thiosuccinimidyl-bearing carboxylic acid derivatives (FIGS. 45, 46 and 48). These derivatives would be useful in the preparation of amine-reactive non-cleavable thiosuccinimidyl-linked maytansinoids described herein. FIGS. 45,46 and 48 show the formation of N-hydroxysuccinimide activated esters however it is obvious to one skilled in the art that several other activated esters could be formed, these include but are not limited to N-sulfosuccinimidyl esters, pentafluorophenol ester, tetrafluorosulfophenol, and nitrophenol ester. Sulfhydryl-bearing maytansinoids, such as DM1 and DM4, can be modified with homobifunctional maleimide reagents to give maytansinoids bearing a maleimide group as shown in FIG. 50.

Preparation of DM1-MCC

A 10 mL round bottom flask was charged with DM1 (44.6 mg, 0.0571 mmol), 1,2-dimethoxyethane (2.5 mL) and equipped with a stir bar. A solution of N-[4-(Carboxycyclohexylmethyl)]maleimide (Toronto Research Chemicals, Inc., MCC, 20.3 mg, 0.08430 mmol) in 1,2-dimethoxyethane (0.5 mL) was added to the reaction flask followed by the addition of pH 7.5 buffer (2.5 mL, 50 mM potassium phosphate, 2 mM EDTA). Several drops of an aqueous saturated sodium bicarbonate solution was added to the reaction solution to maintain the reaction pH. The reaction proceeded at room temperature and was complete after 2 hours. The reaction volume was reduced by half in vacuo, acidified to pH 3 and the product was extracted into ethyl acetate (3×10 mL). The extracts were combined, washed with brine (5 mL) and concentrated in vacuo to yield the crude product. The product was isolated by silica gel chromatography eluting with a 93:7 mixture of methylene chloride and ethanol. Product containing fractions were combined and concentrated to give 46.5 mg (83.5% yield) of DM1-MCC (99.3% purity) as a white solid. Mass spectral analysis of the isolated product gave the expected m+Na$^+$ major molecular ion (m/z 997.3).

Preparation of DM4-SMCC

A 3 mL glass vial was charged with DM4 (24.3 mg, 0.0311 mmol), N-[4-(Carboxycyclohexylmethyl)]maleimide (MCC, Toronto Research Chemicals, Inc. 8.1 mg, 0.0342 mmol) and 1,2-dimethoxyethane (1 mL). The solution stirred as buffer pH 7.5 (1 mL, 50 mM potassium phosphate, 2 mM EDTA) was added to the reaction. The reaction proceeded at room temperature and was complete within two hours. The reaction volume was reduced by half in vacuo, acidified to pH 3 and the product was extracted into ethyl acetate (3×10 mL). The extracts were combined, washed with brine (5 mL) and concentrated in vacuo to yield the crude product. The product was isolated by silica gel chromatography eluting with a 9:1 mixture of methylene chloride and ethanol. Product containing fractions were combined and concentrated to give 14.8 mg (46.9% yield) of DM4-MCC (96.7% purity) as a white solid. Mass spectral analysis of the isolated product gave the expected m+Na$^+$ major molecular ion (m/z 1039.5).

Example XIV

Figure 51:
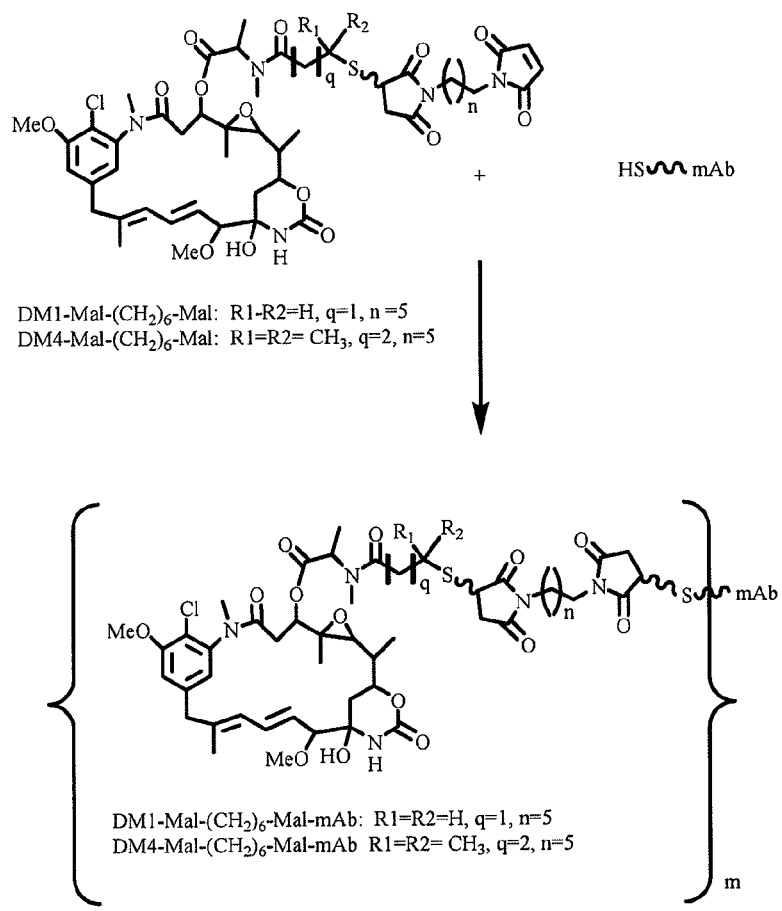
FIG. 51. Conjugation procedure for a non-cleavable thiosuccinimidyl-linked conjugate prepared with compounds of the present invention (mAb=antibody, m=2-8).
Figure 52:
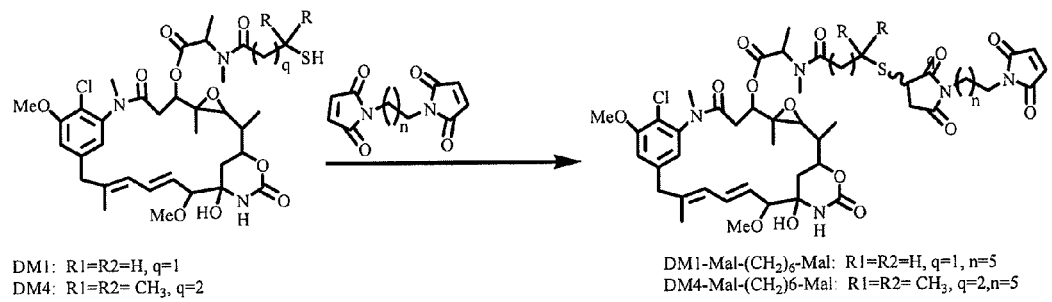
FIG. 52. Synthetic scheme for the preparation of the sulfhydryl-reactive non-cleavable thiosuccinimidyl-linked compounds of the present invention.

Preparation of Non-Cleavable Thiosuccinimdyl-Linked Maytansinoid Derivatives Bearing a Thiol Reactive Moiety The maleimide bearing maytansinoid containing a non-cleavable thiosuccinimidyl group was conjugated to a thiol containing antibody (FIG. 51). The maleimide bearing maytansinoid containing a non-cleavable thiosuccinimidyl group was prepared by coupling a thiol containing maytansinoid to a, bis-maleimide crosslinker (FIG. 52). The reaction conducted herein was done with the Mal-$(CH_2)_6$-Mal reagent, however it is apparent to one skilled in the art that a sulfhydryl-bearing maytansinoid can be to bis-maleimide reagents that contain different spacer units between the maleimide moieties.

Preparation of DM1-Mal-$(CH_2)_6$-Mal

A solution of bis(maleimide)hexanoate (17.9 mg, 0.0648 mmol, 3 equivalents) in THF (0.75 mL) was prepared in a reaction vial. The solution was stirred as DM1 (15.9 mg, 0.0216 mmol) was added in THF (0.75 mL). N,N-diisopropylethylamine (3.3 mg, 0.0259 mmol, 1, 2 equivalents) was then added and the reaction proceeded with stirring at room temperature. Following reaction completion, the reaction volume was reduced in vacuo to give a crude oil. The crude product was redissolved in a minimal volume of $CH_2Cl_2$ and purified by preparative thin-layer chromatography on a 20 cm×20 cm 1000 micron glass plate, eluting with 7% methanol in $CH_2Cl_2$. The product containing band was scraped from the plate, extracted with 20% MeOH in $CH_2Cl_2$, filtered through a sintered glass funnel and concentrated in vacuo to give 10 mg (45.9% yield) of DM1-Mal-$(CH_2)_3$-Mal (95.8% purity). Mass spectral analysis of the isolated product gave the expected m+Na$^+$ (m/z 1036.4) and m+Cl$^-$ (m/z 1048.3) major molecular ions.

Preparation of DM4-Mal-$(CH_2)_6$-Mal

A round bottom flask was charged with bis(maleimide)hexanoate (25.0 mg, 0.090 mmol, 3 equivalents) and THF (1 mL). Once fully dissolved, a solution of N$^{2'}$-deacetyl-N$^{2'}$-(4-mercapto-4-methyl-1-oxopentyl)maytansine (DM4, 23.5 mg, 0.030 mmol) in THF (1 mL) was added to the reaction flask. Phosphate buffer pH 6 (2 mL, 100 mM potassium phosphate, 2 mM EDTA) was then added to the reaction flask. The reaction flask was equipped with a stir bar and a septum and the reaction proceeded at room temperature with stirring. Following reaction completion (~8 hr) the reaction volume was reduced to dryness in vacuo. The crude product was redissolved in a minimal volume of acetonitrile and the product was isolated by semi-preparative C18 HPLC. Product containing fractions were combined and concentrated in vacuo to give 10.6 mg (33.3% yield) of DM4-Mal-$(CH_2)_6$-Mal (99.9% purity). Mass spectral analysis of the isolated product gave the expected m+Na$^+$ (m/z 1078.4) and m+Cl$^-$ (m/z 1090.3) major molecular ions.

Preparation of huC242-Mal-$(CH_2)_6$-Mal-DM1 huC242 (8 mg/mL) in 150 mM HEPES buffer, pH 8.0 containing 5% dimethyl acetamide was modified with 9 equivalents of SPDB for 1 hr at 30'C then eluted through a NAPS sizing column using 50 mM phosphate, 50 mM NaCl, pH 7.5 buffer. To the recovered modified antibody was added 2 µL of 1 M dithiothreitol at 30'C. After 10 min the reaction was purified on a NAP10 column eluting with 50 mM phosphate, 50 mM NaCl, pH 6.5 buffer. DM1-mal-$(CH_2)_6$-mal (1.7 mole equivalents) in dimethyl formamide was added to the fraction containing desired product to obtain 10% v/v dimethyl formamide/buffer. After 1 Hr the crude conjugate was purified on a NAP 25 column eluting with 10 mM citrate, 135 mM NaCl pH 5.5 buffer.

Figure 53:
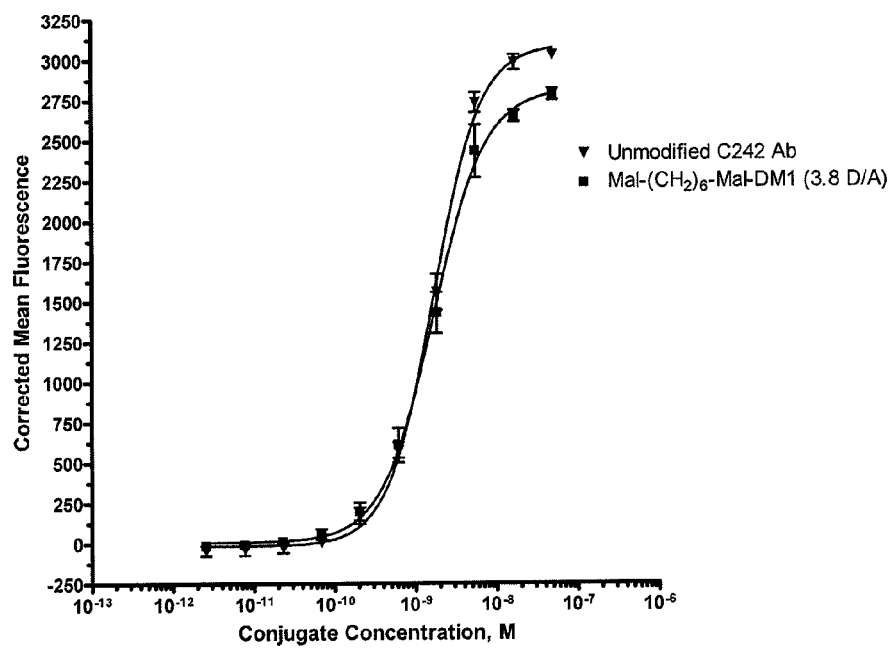
FIG. 53. Shows the binding of anti-CanAg (huC242)-Mal-$(CH_2)_6$-Mal-DM1 conjugate with 3.8 or D/A binds to antigen-positive COL205 cells.
Figure 54:
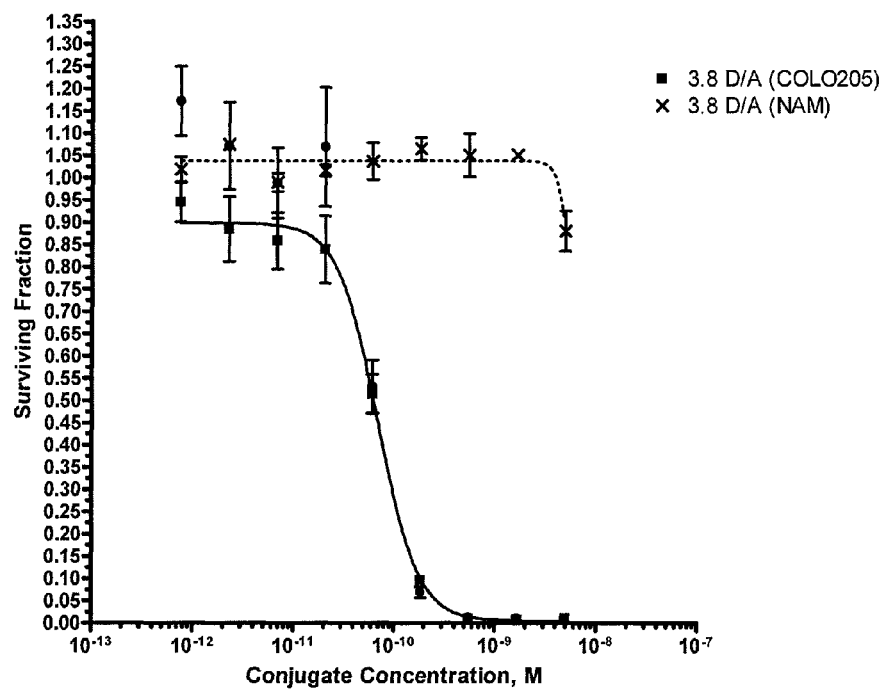
FIG. 54. Shows that the in vitro potency of Anti-CanAg antibody (huC242)-Mal-$(CH_2)_6$-Mal-DM1 conjugate with 3.8 D/A toward antigen-positive COL0205 cells and against antigen-negative Namalwa cells.

Using the previously described binding assay, huC242-Mal-$(CH_2)_6$-Mal-DM1 was shown to bind to antigen-positive COLO205 cells to the same extent as the naked huC242 antibody (FIG. 53). The huC242-Mal-(CH$_2$)$_6$-Mal-DM1 conjugate was shown to be much more cytotoxic to antigen positive COLO205 cells than antigen negative Namalwa cells (FIG. 54).
The invention claimed is:
1. A compound represented by a formula selected from the following:
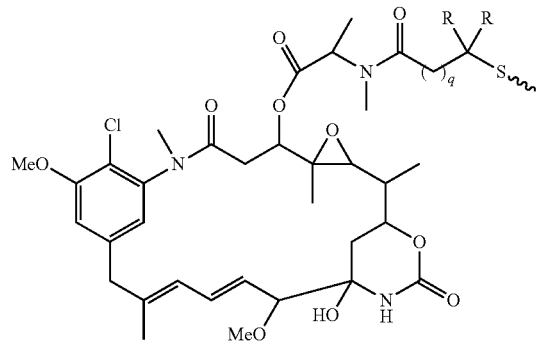
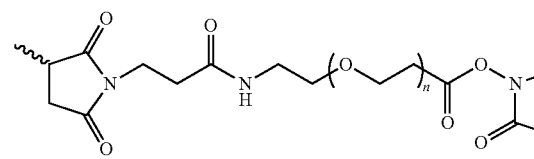
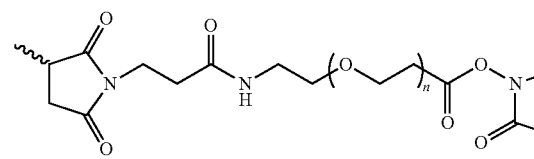
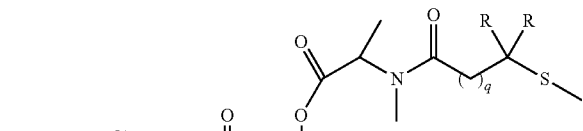
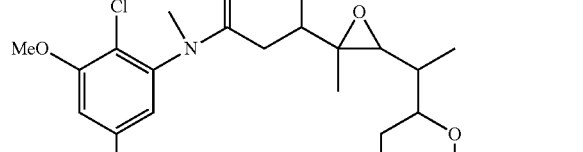
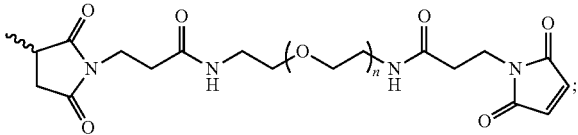
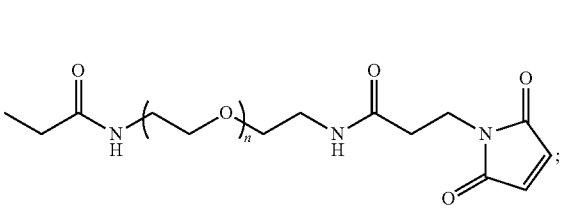
and
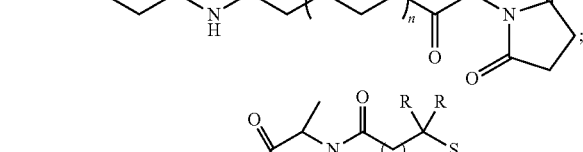
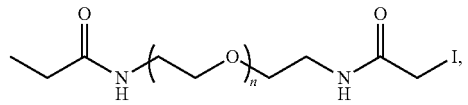
wherein n is an integer from 1 to 2000; R is H and q is 1, or R is CH$_3$ and q is 2.

2. A conjugate represented by a formula selected from:
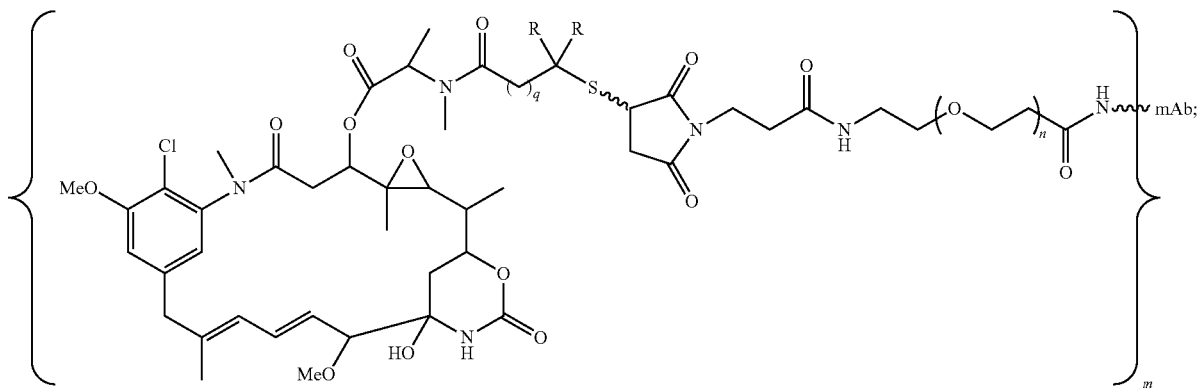
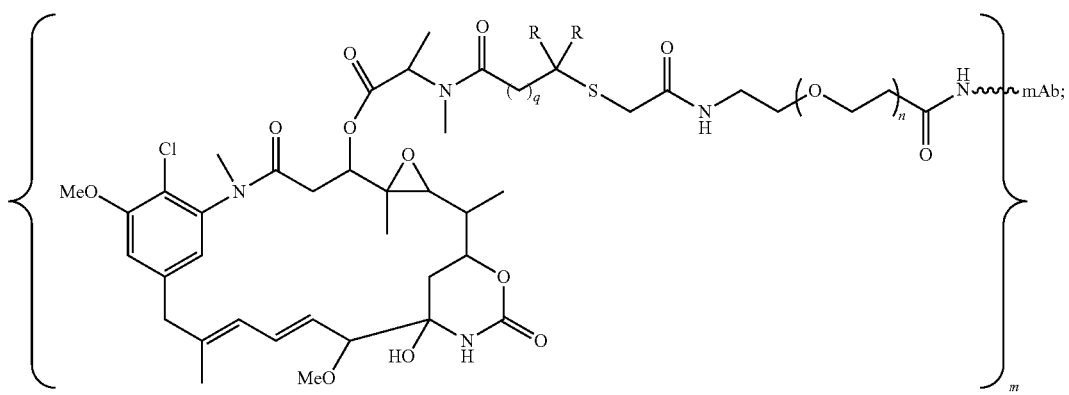
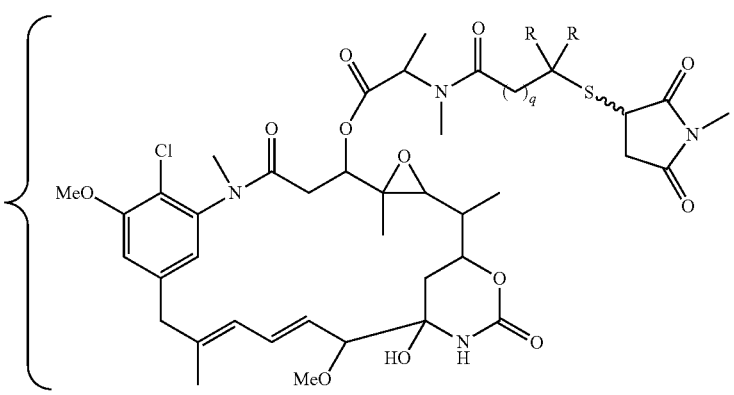
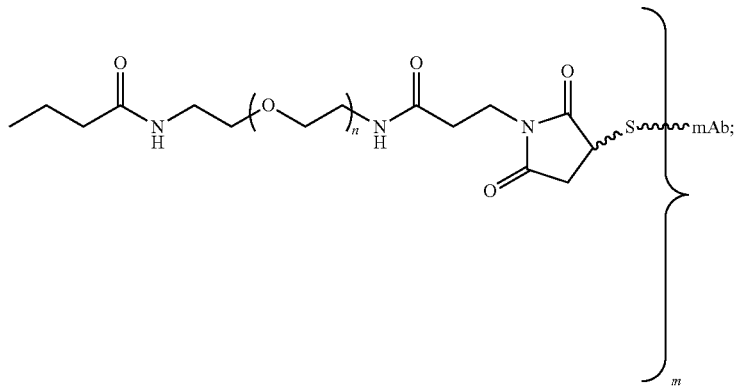

-continued
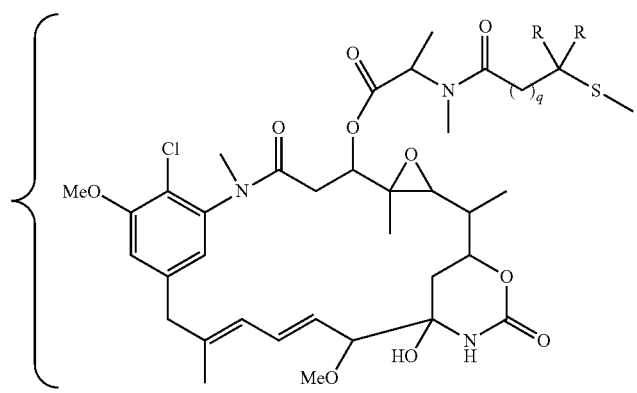
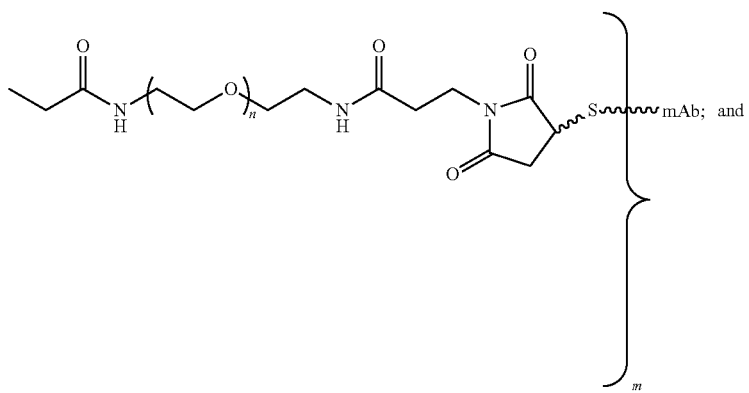
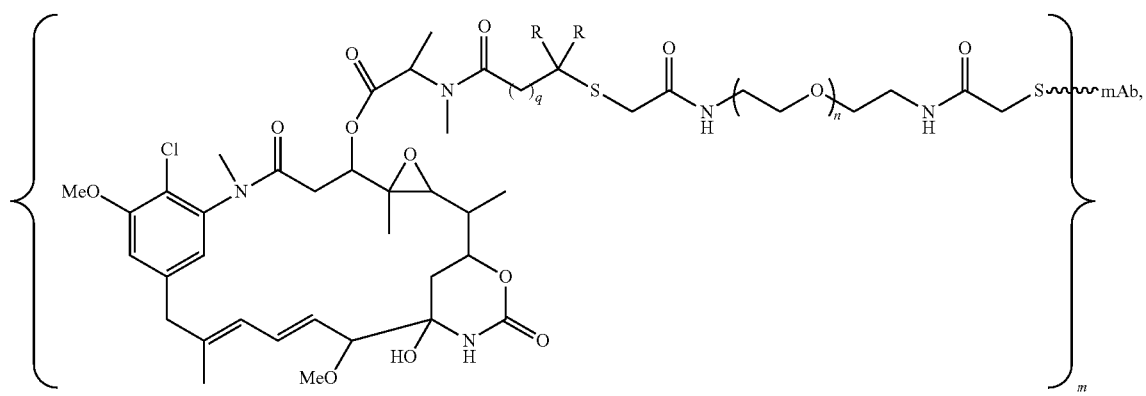

wherein mAb is a monoclonal antibody; n is an integer from 1 to 2000; m is an integer from 2 to 15; R is H and q is 1 or R is $CH_3$ and q is 2, wherein the monoclonal antibody binds to an antigen selected from the group consisting of: EpCAM, CA6, CD2, CD3, CD4, CD5, CD6, CD11, CD11a, CD18, CD19, CD20, CD22, CD26, CD30, CD33, CD37, CD38, CD40, CD44, CD56, CD70, CD79, CD105, CD138, EphA receptor, EphB receptor, epidermal growth factor receptor (EGFR), EGFRvIII, HER2, HER3, insulin-like growth factor I receptor (IGF-IR), CanAg, MUC1, MUC16, vascular endothelial growth factor (VEGF), tissue factor (TF), mesotheliri, cripto, Apo2, alpha$_v$beta$_3$ integrin, alpha$_v$beta$_5$ integrin, alpha$_v$beta$_6$ integrin, and folate receptor.

3. The compound of claim 1, wherein the compound is represented by the following formula:

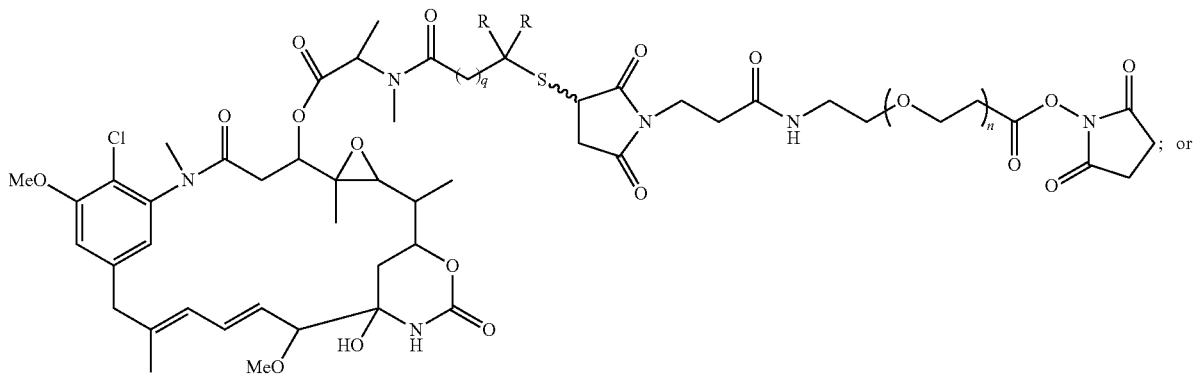

; or

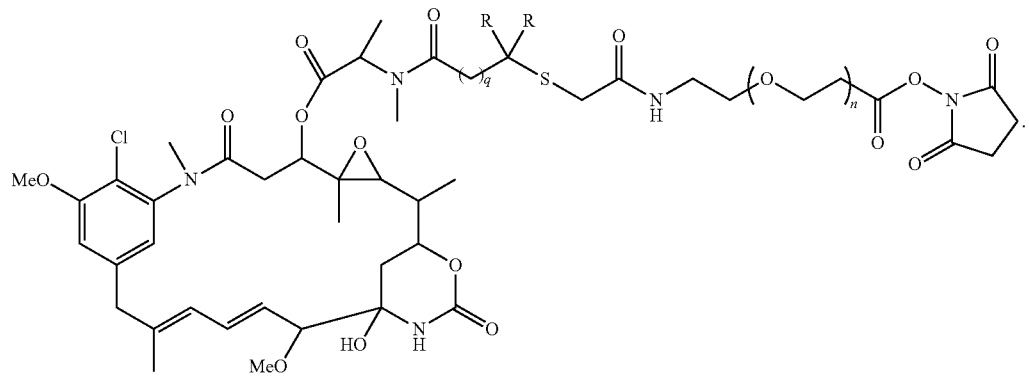

;

4. The conjugate of claim 2, wherein the conjugate is represented by the following formula:

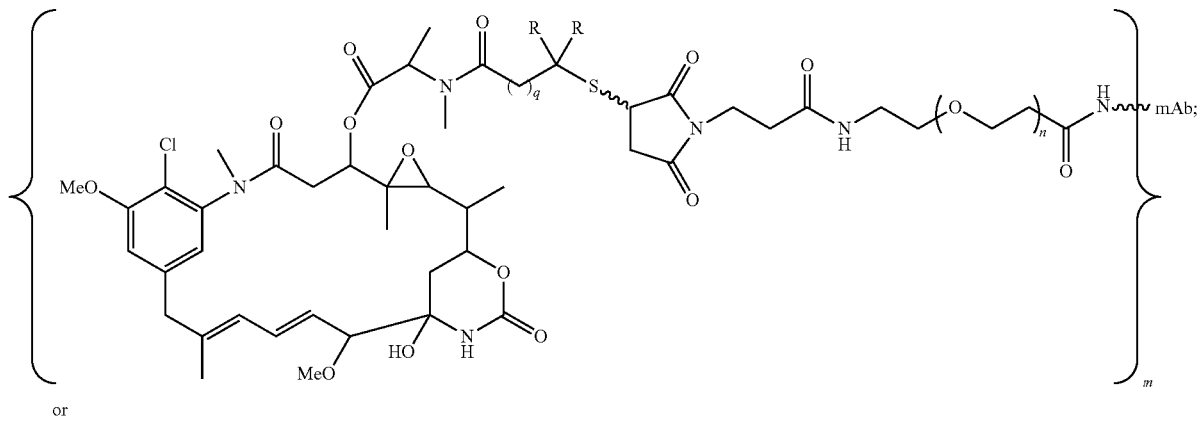

or

-continued

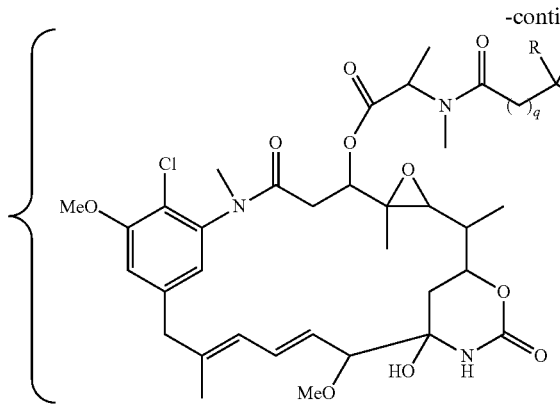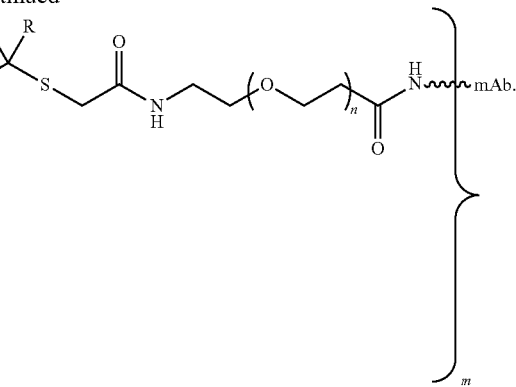

5. The compound of claim 1, wherein n is 1 to 14.
6. The compound of claim 1, wherein n is 1 to 4.
7. The conjugate of claim 2, wherein n is 1 to 14.
8. The conjugate of claim 2, wherein n is 1 to 4.
9. The compound of claim 3, wherein n is 1 to 14.
10. The compound of claim 3, wherein n is 1 to 4.
11. The conjugate of claim 4, wherein n is 1 to 14.
12. The conjugate of claim 4, wherein n is 1 to 4.
13. A composition comprising any one of the conjugates of claim 2, a pharmaceutically acceptable salt or solvate thereof, and a pharmaceutically acceptable carrier, diluent or excipient.
14. The composition of claim 13, wherein n is 1 to 14.
15. The composition of claim 13, wherein n is 1 to 4.
16. The conjugate of claim 2, wherein the monoclonal antibody is a resurfaced monoclonal antibody or an antigen-binding fragment thereof, or a resurfaced single chain monoclonal antibody or an antigen-binding fragment thereof.
17. The conjugate of claim 2, wherein the monoclonal antibody is a humanized monoclonal antibody or an antigen-binding fragment thereof, or a humanized single chain monoclonal antibody or an antigen-binding fragment thereof.
18. The conjugate of claim 2, wherein the monoclonal antibody is a chimeric antibody or an antigen-binding fragment thereof, a domain antibody, or an antigen-binding fragment thereof.
19. The conjugate of claim 2, wherein the monoclonal antibody is MY9 antibody that binds to CD33, anti-B4 antibody that binds to CD19, C242 antibody that binds to CanAg, or a monoclonal antibody that binds to an antigen selected from the group consisting of EpCAM, CD2, CD3, CD4, CD5, CD6, CD11, CD19, CD20, CD22, CD26, CD30, CD33, CD37, CD38, CD40, CD44, CD56, CD79, CD105, CD138, EphA receptor, EphB receptor, EGFR, EGFRvIII, HER2, HER3, mesothelin, cripto, alpha$_v$beta$_3$ integrin, alpha$_v$beta$_5$ integrin, and alpha$_v$beta$_6$ integrin.

20. The conjugate of claim 2, wherein the monoclonal antibody is selected from the group consisting of: My9-6 antibody that binds to CD33, or a humanized monoclonal antibody, a human monoclonal antibody, or a resurfaced monoclonal antibody thereof; anti-B4 antibody that binds to CD19, or a humanized monoclonal antibody, a human monoclonal antibody, or a resurfaced monoclonal antibody thereof; C242 antibody that binds to CanAg, a humanized monoclonal antibody, a human monoclonal antibody, or a resurfaced monoclonal antibody thereof; N901 antibody that binds to CD56, or a humanized monoclonal antibody, a human monoclonal antibody, or a resurfaced monoclonal antibody thereof; DS6 antibody that binds to CA6, or a humanized monoclonal antibody, a human monoclonal antibody, or a resurfaced monoclonal antibody thereof; CNTO 95 antibody that binds to alpha$_v$beta$_3$, alpha$_v$beta$_5$ or alpha$_v$beta$_6$ integrin, or a humanized monoclonal antibody, a human monoclonal antibody, or a resurfaced monoclonal antibody thereof; B-B4 antibody that binds to CD138, or a humanized monoclonal antibody, a human monoclonal antibody, or a resurfaced monoclonal antibody thereof, trastuzumab, pertuzumab, bivatuzumab, rituximab, and a monoclonal antibody that binds to EphA2 receptor, CD38 or IGF-IR.

* * * * *